United States Patent
Chen et al.

(10) Patent No.: US 10,722,431 B2
(45) Date of Patent: Jul. 28, 2020

(54) DISPENSER SYSTEM AND METHODS FOR MEDICATION COMPLIANCE

(71) Applicants: Changhai Chen, Bloomfield Hills, MI (US); Daniel Chen, Bloomfield Hills, MI (US); Michael Chen, Bloomfield Hills, MI (US)

(72) Inventors: Changhai Chen, Bloomfield Hills, MI (US); Daniel Chen, Bloomfield Hills, MI (US); Michael Chen, Bloomfield Hills, MI (US)

(*) Notice: Subject to any disclaimer, the term of this patent is extended or adjusted under 35 U.S.C. 154(b) by 60 days.

(21) Appl. No.: 15/896,141

(22) Filed: Feb. 14, 2018

(65) Prior Publication Data

US 2018/0168935 A1 Jun. 21, 2018

Related U.S. Application Data

(63) Continuation-in-part of application No. 15/687,437, filed on Aug. 25, 2017, now Pat. No. 10,073,954, (Continued)

(51) Int. Cl.
*B65B 5/10* (2006.01)
*B65B 1/32* (2006.01)
(Continued)

(52) U.S. Cl.
CPC .......... *A61J 7/0436* (2015.05); *A61J 7/0418* (2015.05); *B65B 1/32* (2013.01); *B65B 1/46* (2013.01);
(Continued)

(58) Field of Classification Search
CPC ......... A61J 7/0436; A61J 7/0418; B65B 1/32; B65B 1/46; B65B 5/103
(Continued)

(56) References Cited

U.S. PATENT DOCUMENTS

| 3,837,139 A | 9/1974 | Roseberg |
| 3,911,856 A | 10/1975 | Ewing |

(Continued)

FOREIGN PATENT DOCUMENTS

| WO | WO-2013127564 A1 | 9/2013 |
| WO | WO-2015021543 A1 | 2/2015 |

(Continued)

OTHER PUBLICATIONS

U.S. Appl. No. 15/395,076, filed Dec. 30, 2016, Changhai Chen et al.

(Continued)

*Primary Examiner* — Rakesh Kumar

(57) ABSTRACT

A medication dispensing system is provided and includes a medicine transfer device (MTD) and a controller. The MTD transfers medicine between first and second containers. The first container initially stores medicine. The controller: determines a first predetermined amount of medicine to be dispensed from the medicine dispensing system; causes the MTD to discharge a second predetermined amount of the medicine from the first container onto the MTD, and transfer a third predetermined amount of the medicine from the MTD to the second container; subsequent to the transfer of the third predetermined amount, determine whether the second container has greater than or equal to the first predetermined amount; and if the second container has less than the first predetermined amount, cause the MTD to transfer a portion of the medicine on the MTD into the second container or discharge a portion of the medicine in the first container onto the MTD.

9 Claims, 48 Drawing Sheets

Related U.S. Application Data which is a continuation of application No. 15/687,428, filed on Aug. 25, 2017, which is a continuation of application No. PCT/US2017/048643, filed on Aug. 25, 2017.

(60) Provisional application No. 62/584,041, filed on Nov. 9, 2017, provisional application No. 62/590,305, filed on Nov. 23, 2017, provisional application No. 62/416,251, filed on Nov. 2, 2016, provisional application No. 62/379,866, filed on Aug. 26, 2016.

(51) Int. Cl.
  *B65B 1/46* (2006.01)
  *B65B 57/14* (2006.01)
  *A61J 7/04* (2006.01)
  *G16H 20/13* (2018.01)
  *A61J 7/02* (2006.01)

(52) U.S. Cl.
  CPC ............. *B65B 5/103* (2013.01); *B65B 57/14* (2013.01); *G16H 20/13* (2018.01); *A61J 7/02* (2013.01); *A61J 2200/30* (2013.01); *A61J 2200/74* (2013.01); *A61J 2205/10* (2013.01); *A61J 2205/30* (2013.01); *A61J 2205/60* (2013.01)

(58) Field of Classification Search
  USPC ........................................................ 700/240
  See application file for complete search history.

(56) References Cited

U.S. PATENT DOCUMENTS

| | | |
|---|---|---|
| 4,530,447 A | 7/1985 | Greenspan |
| 4,725,999 A | 2/1988 | Tate |
| 4,899,839 A | 2/1990 | Dessertine et al. |
| 5,014,798 A | 5/1991 | Glynn |
| 5,226,539 A | 7/1993 | Cheng |
| 5,337,919 A | 8/1994 | Spaulding et al. |
| 5,348,061 A | 9/1994 | Riley et al. |
| 5,597,995 A | 1/1997 | Williams et al. |
| 5,823,346 A | 10/1998 | Weiner |
| 5,971,594 A | 10/1999 | Sahai et al. |
| 6,032,609 A | 3/2000 | Luoma |
| 6,036,812 A * | 3/2000 | Williams ............... B65G 1/045 156/277 |
| 6,075,755 A | 6/2000 | Zarchan |
| 6,152,067 A | 11/2000 | Mathison |
| 6,169,707 B1 | 1/2001 | Newland |
| 6,286,714 B1 | 9/2001 | Pearson et al. |
| 6,294,999 B1 | 9/2001 | Yarin et al. |
| 6,380,858 B1 | 4/2002 | Yarin et al. |
| 6,588,548 B1 | 7/2003 | Dewitt |
| 6,592,005 B1 | 7/2003 | Coughlin et al. |
| 6,604,650 B2 | 8/2003 | Sagar |
| 6,636,780 B1 | 10/2003 | Haitin et al. |
| 6,702,146 B2 | 3/2004 | Varis |
| 6,771,174 B2 | 8/2004 | Broas |
| 6,909,359 B1 | 6/2005 | McGovern |
| 6,996,455 B2 | 2/2006 | Eggenberger et al. |
| 7,002,476 B2 | 2/2006 | Rapchak |
| 7,006,893 B2 | 2/2006 | Hart et al. |
| 7,028,723 B1 * | 4/2006 | Alouani ................. B65B 5/101 141/83 |
| 7,048,141 B2 | 5/2006 | Abdulhay et al. |
| 7,061,831 B2 | 6/2006 | De La Huerga |
| 7,081,807 B2 | 7/2006 | Lai |
| 7,198,172 B2 | 4/2007 | Harvey et al. |
| 7,213,721 B2 | 5/2007 | Abdulhay et al. |
| 7,269,476 B2 | 9/2007 | Ratnakar |
| 7,302,311 B2 | 11/2007 | Varis |
| 7,322,355 B2 | 1/2008 | Jones et al. |
| 7,334,047 B1 | 2/2008 | Pillay-Esnault |
| 7,347,341 B2 | 3/2008 | Burggraf |
| 7,359,765 B2 | 4/2008 | Varvarelis et al. |
| 7,424,888 B2 | 9/2008 | Harvey et al. |
| 7,440,817 B2 | 10/2008 | Fu |
| 7,496,521 B1 | 2/2009 | Louie et al. |
| 7,534,230 B2 | 5/2009 | Follman et al. |
| 7,542,379 B2 | 6/2009 | Kimel et al. |
| 7,555,362 B2 | 6/2009 | Broussard et al. |
| 7,602,275 B2 | 10/2009 | Dishongh et al. |
| 7,711,449 B2 | 5/2010 | Abdulhay et al. |
| 7,712,288 B2 | 5/2010 | Ramasubramanian et al. |
| 7,715,277 B2 | 5/2010 | de la Huerga |
| 7,735,684 B2 | 6/2010 | Coe et al. |
| 7,801,745 B2 | 9/2010 | Walker et al. |
| 7,844,361 B2 | 11/2010 | Jean-Pierre |
| 7,861,848 B2 | 1/2011 | Monti |
| 7,886,931 B2 | 2/2011 | Handfield et al. |
| 7,896,192 B2 | 3/2011 | Conley et al. |
| 7,928,835 B1 | 4/2011 | Jovanov et al. |
| 7,930,064 B2 | 4/2011 | Popovich, Jr. et al. |
| 7,957,984 B1 | 6/2011 | Vallone |
| 7,963,201 B2 | 6/2011 | Willoughby et al. |
| 7,978,564 B2 | 7/2011 | De La Huerga |
| 8,005,689 B2 | 8/2011 | Palazzolo et al. |
| 8,009,040 B2 | 8/2011 | Kennedy |
| 8,027,748 B2 | 9/2011 | Handfield et al. |
| 8,055,509 B1 | 11/2011 | Walker et al. |
| 8,061,351 B2 | 11/2011 | Dave |
| 8,068,931 B2 | 11/2011 | Tran et al. |
| 8,069,056 B2 | 11/2011 | Walker et al. |
| 8,085,135 B2 | 12/2011 | Cohen Alloro et al. |
| 8,108,068 B1 | 1/2012 | Boucher et al. |
| 8,109,066 B2 | 2/2012 | Leu et al. |
| 8,154,390 B2 | 4/2012 | Heath et al. |
| 8,175,746 B2 | 5/2012 | Godlewski |
| 8,201,691 B1 | 6/2012 | Chowdhury |
| 8,212,677 B2 | 7/2012 | Ferguson |
| 8,251,629 B2 | 8/2012 | Schifman et al. |
| 8,284,386 B2 | 10/2012 | Young et al. |
| 8,319,613 B2 | 11/2012 | Lazar |
| 8,348,093 B2 | 1/2013 | Jeyarajan |
| 8,360,274 B2 | 1/2013 | Shen et al. |
| 8,386,275 B2 | 2/2013 | Chambers |
| 8,391,104 B2 * | 3/2013 | de la Huerga .......... A61J 1/035 368/10 |
| 8,408,208 B2 | 4/2013 | Bacon |
| 8,417,381 B2 | 4/2013 | Vonk et al. |
| 8,452,446 B1 | 5/2013 | Madris et al. |
| 8,483,872 B2 | 7/2013 | Ratnakar |
| 8,502,671 B2 | 8/2013 | Marcovici |
| 8,508,346 B2 | 8/2013 | Heath et al. |
| 8,511,304 B2 | 8/2013 | Anderson et al. |
| 8,556,120 B2 | 10/2013 | Ando et al. |
| 8,560,117 B2 | 10/2013 | Handfield et al. |
| 8,606,595 B2 | 12/2013 | Udani |
| 8,622,241 B2 | 1/2014 | Geboers et al. |
| 8,648,716 B2 | 2/2014 | Steinmetz |
| 8,666,543 B2 | 3/2014 | MacVittie et al. |
| 8,712,587 B2 | 4/2014 | Handfield et al. |
| 8,727,180 B2 | 5/2014 | Zonana et al. |
| 8,744,620 B2 | 6/2014 | Shavelsky et al. |
| 8,752,728 B2 | 6/2014 | Tignanelli et al. |
| 8,754,769 B2 | 6/2014 | Stein et al. |
| 8,781,856 B2 | 7/2014 | Hanina et al. |
| 8,798,789 B2 | 8/2014 | Horev et al. |
| 8,807,389 B2 | 8/2014 | Meyer et al. |
| 8,825,511 B2 | 9/2014 | Hamilton et al. |
| 8,849,449 B2 | 9/2014 | Waugh et al. |
| 8,857,617 B2 | 10/2014 | Balakier et al. |
| 8,862,266 B2 * | 10/2014 | van Ooyen ............. G07F 11/44 221/241 |
| 8,874,260 B2 | 10/2014 | Saltsov |
| 8,877,336 B2 | 11/2014 | Bromley-Davenport et al. |
| 8,878,654 B2 | 11/2014 | Cohen-Alloro et al. |
| 8,884,752 B2 | 11/2014 | Tai et al. |
| 8,896,428 B2 | 11/2014 | Shalala |
| 8,905,964 B2 | 12/2014 | Poutiatine et al. |
| 8,908,163 B2 | 12/2014 | Young et al. |
| 8,919,561 B2 | 12/2014 | Boisseau |

(56) References Cited

U.S. PATENT DOCUMENTS

| | | | |
|---|---|---|---|
| 8,928,467 B2 | 1/2015 | Jacobs et al. | |
| 8,960,075 B2 | 2/2015 | Traitler et al. | |
| 8,963,710 B2 | 2/2015 | Huang et al. | |
| 8,970,380 B2 | 3/2015 | Buco et al. | |
| 8,977,390 B2 | 3/2015 | Jefferies et al. | |
| 8,985,388 B2 * | 3/2015 | Ratnakar | A61J 7/0481 177/25.18 |
| 9,007,875 B2 | 4/2015 | Nurse et al. | |
| 9,014,427 B2 | 4/2015 | Bear et al. | |
| 9,031,689 B1 | 5/2015 | Fink et al. | |
| 9,043,015 B2 | 5/2015 | Ratnakar | |
| 9,066,849 B2 * | 6/2015 | Fung | A61J 1/03 |
| 9,069,887 B2 | 6/2015 | Gupta et al. | |
| 9,081,886 B2 | 7/2015 | Schifman et al. | |
| 9,081,887 B2 | 7/2015 | Olson et al. | |
| 9,103,307 B2 | 8/2015 | Lingener | |
| 9,123,077 B2 | 9/2015 | Silkaitis et al. | |
| 9,125,797 B2 | 9/2015 | Khasnis | |
| 9,125,798 B2 | 9/2015 | Stein et al. | |
| 9,135,482 B2 | 9/2015 | Caputo et al. | |
| 9,139,316 B2 * | 9/2015 | Husnu | B65B 3/003 |
| 9,147,044 B2 | 9/2015 | Shows et al. | |
| 9,150,119 B2 | 10/2015 | Henderson et al. | |
| 9,171,415 B2 | 10/2015 | Adams et al. | |
| 9,189,601 B2 | 11/2015 | Simmons et al. | |
| 9,202,165 B2 * | 12/2015 | Heinz | G06M 3/02 |
| 9,202,253 B2 | 12/2015 | Macoviak et al. | |
| 9,218,454 B2 | 12/2015 | Kiani et al. | |
| 9,218,458 B2 | 12/2015 | Baarman et al. | |
| 9,223,934 B2 | 12/2015 | Hussain et al. | |
| 9,224,124 B2 | 12/2015 | Rahim et al. | |
| 9,235,683 B2 | 1/2016 | Robertson et al. | |
| 9,251,493 B2 * | 2/2016 | Jacobs | H04N 7/18 |
| 9,268,913 B2 | 2/2016 | Johnson et al. | |
| 9,268,978 B2 | 2/2016 | Hussain et al. | |
| 9,280,863 B2 | 3/2016 | Spignesi, Jr. et al. | |
| 9,289,584 B2 | 3/2016 | Chiao et al. | |
| 9,298,887 B2 | 3/2016 | Clark et al. | |
| 9,308,151 B2 | 4/2016 | Chaturvedi et al. | |
| 9,321,568 B2 | 4/2016 | Gelardi et al. | |
| 9,492,355 B2 | 11/2016 | Ratnakar | |
| 10,073,954 B2 * | 9/2018 | Chen | B65B 5/103 |
| 2002/0073560 A1 | 6/2002 | LoRocco | |
| 2002/0103573 A1 | 8/2002 | Fellows et al. | |
| 2002/0153411 A1 | 10/2002 | Wan et al. | |
| 2002/0179619 A1 | 12/2002 | Geltser et al. | |
| 2003/0111484 A1 * | 6/2003 | Pearson | A61J 7/02 221/211 |
| 2004/0030285 A1 | 2/2004 | Lavi et al. | |
| 2006/0213921 A1 | 9/2006 | Abdulhay et al. | |
| 2007/0073560 A1 * | 3/2007 | Walker et al. | B65B 57/20 |
| 2007/0093932 A1 | 4/2007 | Abdulhay et al. | |
| 2008/0109510 A1 | 5/2008 | Gerlt et al. | |
| 2008/0172253 A1 | 7/2008 | Chung et al. | |
| 2008/0275738 A1 | 11/2008 | Shillingburg | |
| 2008/0293392 A1 | 11/2008 | Strother | |
| 2009/0057328 A1 | 3/2009 | Ratnakar | |
| 2009/0259336 A1 | 10/2009 | Ratnakar | |
| 2009/0294521 A1 | 12/2009 | de la Huerga | |
| 2010/0049363 A1 | 2/2010 | Ratnakar | |
| 2010/0076595 A1 * | 3/2010 | Nguyen | A61J 7/0084 700/232 |
| 2010/0100237 A1 | 4/2010 | Ratnakar | |
| 2010/0205002 A1 | 8/2010 | Chambers | |
| 2011/0298587 A1 | 12/2011 | Walz | |
| 2012/0118165 A1 | 5/2012 | Van Os et al. | |
| 2012/0199650 A1 | 8/2012 | Horst et al. | |
| 2013/0042943 A1 | 2/2013 | Bassani | |
| 2013/0054017 A1 | 2/2013 | Horev et al. | |
| 2013/0141236 A1 | 6/2013 | Chu | |
| 2013/0144431 A1 | 6/2013 | Tidhar et al. | |
| 2014/0025199 A1 | 1/2014 | Berg et al. | |
| 2014/0074283 A1 | 3/2014 | Blackburn | |
| 2014/0098645 A1 | 4/2014 | Mularczyk | |
| 2014/0116571 A1 | 5/2014 | Bassani | |
| 2014/0207278 A1 | 7/2014 | Czaja et al. | |
| 2014/0231446 A1 | 8/2014 | Kim | |
| 2014/0251850 A1 | 9/2014 | Huang et al. | |
| 2014/0262918 A1 | 9/2014 | Chu | |
| 2014/0263425 A1 | 9/2014 | Akdogan et al. | |
| 2014/0266760 A1 | 9/2014 | Burke, Jr. et al. | |
| 2014/0267719 A1 | 9/2014 | Akdogan et al. | |
| 2014/0277707 A1 | 9/2014 | Akdogan et al. | |
| 2014/0326744 A1 * | 11/2014 | Ratnakar | A61J 7/02 221/1 |
| 2014/0346186 A1 | 11/2014 | Reddy et al. | |
| 2014/0350720 A1 | 11/2014 | Lehmann et al. | |
| 2014/0358278 A1 * | 12/2014 | Zhang | G07F 17/0092 700/240 |
| 2015/0027286 A1 | 1/2015 | Yuyama et al. | |
| 2015/0048010 A1 | 2/2015 | Joplin et al. | |
| 2015/0048100 A1 | 2/2015 | Dickie et al. | |
| 2015/0048102 A1 | 2/2015 | Dickie et al. | |
| 2015/0066206 A1 * | 3/2015 | Patel | G06F 19/00 700/235 |
| 2015/0090733 A1 | 4/2015 | Park | |
| 2015/0122688 A1 | 5/2015 | Dias et al. | |
| 2015/0145672 A1 | 5/2015 | Chu | |
| 2015/0205934 A1 | 7/2015 | Jefferies et al. | |
| 2015/0228180 A1 | 8/2015 | Tai et al. | |
| 2015/0254427 A1 | 9/2015 | Burrows et al. | |
| 2015/0257980 A1 | 9/2015 | Fung et al. | |
| 2015/0257981 A1 | 9/2015 | Arad et al. | |
| 2015/0266654 A1 | 9/2015 | Baarman et al. | |
| 2015/0291344 A1 | 10/2015 | MacVittie et al. | |
| 2015/0317455 A1 | 11/2015 | Lehmann et al. | |
| 2015/0342830 A1 | 12/2015 | Bujalski et al. | |
| 2015/0363570 A1 | 12/2015 | Hanina et al. | |
| 2016/0001955 A1 | 1/2016 | Wang et al. | |
| 2016/0015602 A1 | 1/2016 | Panzini et al. | |
| 2016/0022541 A1 | 1/2016 | Dalal et al. | |
| 2016/0026773 A1 | 1/2016 | Chu et al. | |
| 2016/0039553 A1 | 2/2016 | Akdogan et al. | |
| 2016/0039621 A1 | 2/2016 | Akdogan et al. | |
| 2016/0055317 A1 * | 2/2016 | Levine | G06F 19/326 705/2 |
| 2016/0075460 A1 | 3/2016 | Despa et al. | |
| 2016/0078708 A1 | 3/2016 | Salem | |
| 2016/0085940 A1 * | 3/2016 | Jacobs | H04N 7/18 705/2 |
| 2016/0089304 A1 | 3/2016 | Niven | |
| 2016/0105522 A1 | 4/2016 | Somani et al. | |
| 2016/0107820 A1 | 4/2016 | MacVittie et al. | |
| 2016/0120758 A1 | 5/2016 | Pi et al. | |
| 2016/0122045 A1 | 5/2016 | Kames et al. | |
| 2016/0128906 A1 | 5/2016 | Baarman et al. | |
| 2016/0136054 A1 | 5/2016 | Bunker et al. | |
| 2016/0143807 A1 | 5/2016 | Ika et al. | |
| 2016/0143808 A1 | 5/2016 | Pattison et al. | |
| 2016/0151246 A1 | 6/2016 | Sotelo | |
| 2016/0158107 A1 | 6/2016 | Dvorak et al. | |
| 2016/0158108 A1 | 6/2016 | Gofer et al. | |
| 2016/0159554 A1 | 6/2016 | Daniels et al. | |
| 2016/0162660 A1 | 6/2016 | Strong | |
| 2016/0162661 A1 | 6/2016 | Herman et al. | |
| 2016/0171176 A1 | 6/2016 | Stephens | |
| 2016/0193113 A1 | 7/2016 | Jacobs et al. | |
| 2016/0196409 A1 | 7/2016 | Paydar et al. | |
| 2016/0199260 A1 | 7/2016 | Andersen, Sr. | |
| 2016/0203292 A1 | 7/2016 | Kamen et al. | |
| 2016/0207691 A1 | 7/2016 | Benouali et al. | |
| 2016/0212389 A1 | 7/2016 | Mehrotra et al. | |
| 2016/0228333 A1 | 8/2016 | Bukstein et al. | |
| 2016/0239635 A1 | 8/2016 | Fateh | |

(56) References Cited

U.S. PATENT DOCUMENTS

2016/0247345 A1    8/2016  Ratnakar
2016/0327427 A1   11/2016  Briones et al.

FOREIGN PATENT DOCUMENTS

WO    WO-2015054345 A1    4/2015
WO    WO-2016023153 A1 *  2/2016  ................ A61J 7/04

OTHER PUBLICATIONS

U.S. Appl. No. 15/613,675, filed Jun. 5, 2017, Changhai Chen et al.
U.S. Appl. No. 15/613,852, filed Jun. 5, 2017, Changhai Chen
U.S. Appl. No. 15/687,428, filed Aug. 25, 2017, Changhai Chen et al.
U.S. Appl. No. 15/687,437, filed Aug. 25, 2017, Changhai Chen et al.
International Search Report from PCT/US17/40863 dated Sep. 28, 2017.
International Search Report from PCT/US17/48643 dated Nov. 7, 2017.

\* cited by examiner

DISPENSER SYSTEM AND METHODS FOR MEDICATION COMPLIANCE

CROSS-REFERENCE TO RELATED APPLICATIONS

This non-provisional application claims the benefit of U.S. Provisional Patent Application No. 62/584,041 filed Nov. 9, 2017 and U.S. Provisional Patent Application No. 62/590,305 filed Nov. 23, 2017. This non-provisional application is a continuation-in-part of U.S. patent application Ser. No. 15/687,437 filed Aug. 25, 2017, which is a continuation of non-provisional U.S. patent application Ser. No. 15/687,428 filed Aug. 25, 2017, which is a continuation of PCT Patent Application No. PCT/US2017/048643 filed Aug. 25, 2017, which claims the benefit of U.S. Provisional Patent Application No. 62/416,251 filed Nov. 2, 2016 and U.S. Provisional Application No. 62/379,866 filed Aug. 26, 2016.

This application is related to PCT Application PCT/US2017/040863 filed Jul. 6, 2017, which is a continuation of non-provisional U.S. patent application Ser. No. 15/613,852 filed Jun. 5, 2017, which is a continuation of non-provisional U.S. patent application Ser. No. 15/613,675 filed Jun. 5, 2017, which claims priority to U.S. Provisional Patent Application No. 62/392,621 filed Jun. 6, 2016. This application is also related to U.S. patent application Ser. No. 15/395,076 filed Dec. 30, 2016 and U.S. patent application Ser. No. 15/202,778 filed Jul. 6, 2016.

The entire disclosures of the applications referenced above are incorporated herein by reference.

BACKGROUND

Improving medical adherence and compliance is an area of interest for medical practitioners and patients alike, including in pharmacy, facility and home settings. Traditional solutions, like the various types of pill boxes and smart caps, may fail to address the root causes of medical non-adherence completely and effectively.

For instance, in an attempt to improve patient compliance, some systems may include timer-like functions or smart phone applications to remind patients when to take specific medications. However, these solutions may not effectively monitor whether the right dosage has been taken. For instance, tracking each time a bottle has been opened may not account for, for instance, how many pills are taken at a time. Furthermore, pharmacists or clinicians may not properly preprogram a patient's drug routine into a solution (e.g., in the form of programming a traditional RF tag, as an example). Such can limit accessibility of solutions to a minority of the population and may prevent proper usage for many patients and caregivers. For people taking multiple medications, there is always a possibility of mixing-up pills between reminders. For instance, a physical reminder device initially set-up to remind and track pill A may not track a second pill B if misplaced in a bottle.

Pre-sorting pill devices (e.g., pill boxes) may help manage complex medicine regimens. For instance, a user may actively prepare the medications to be taken over a coming week or even a month. However, these solutions may include significant cognitive effort, and pre-sorting the medications can be both cumbersome for the user, and prone to errors in sorting the medications correctly (i.e., the user may not correctly sort out the correct medication, in the right dosage, for the right time, all the time). Other solutions may fail to effectively remind or notify the patient when to take a certain dosage of medication.

There have also been numerous attempts to develop automatic dispensing systems. However, previous medicine-dispensing devices may fail to reliably dispense medications when needed.

Therefore, a need in the field exists for a solution that can not only dispense and remind patients when to take specific medications, but also track that the correct dosages have been taken by the patient at the correct time and ensure that the right medication is taken. A need also exists for a dispensing system to successfully determine whether there has been a mistake in the dispensing process without intervention from the patient; this need exists to increase operational reliability to extremely high levels. A further need exists for a reminder system notifying patients to bring their medications along when they leave their homes. A need also exists for a solution for the above, while still remaining accessible to an average patient (i.e., having only minimal changes to the patient's lifestyle) since some solutions rely on pharmacists or clinicians to program the device, which can limit accessibility of the solution to limited populations with access to the technology.

SUMMARY

A medication dispensing system is provided and includes a medicine transfer device and a controller. The medicine transfer device is configured to transfer medicine between a first container and a second container, where the first container is configured to initially store medicine. The controller is configured to: determine a first predetermined amount of medicine to be dispensed from the medicine dispensing system; cause the medicine transfer device to (i) discharge at least a second predetermined amount of the medicine from the first container onto the medicine transfer device, and (ii) transfer at least a third predetermined amount of the medicine from the medicine transfer device to the second container; subsequent to the transfer of the third predetermined amount of the medicine, determine whether the second container has greater than or equal to the first predetermined amount of the medicine; and if the second container has less than the first predetermined amount of the medicine, cause the medicine transfer device to at least one of (i) transfer at least a portion of the medicine on the medicine transfer device into the second container, or (ii) discharge at least a portion of the medicine in the first container onto the medicine transfer device.

In other features, a medication dispensing system is also provided and includes a container transfer device and a controller. The container transfer device is configured to move a first container and a second container to transfer medicine between the first container and the second container, where the first container is configured to initially store the medicine. The controller is configured to: determine a first predetermined amount of medicine to be dispensed from the medicine dispensing system; cause the container transfer device to discharge at least a second predetermined amount of the medicine from the first container into the second container; subsequent to the discharge of the at least the second predetermined amount of the medicine, determine whether the second container has greater than or equal to the first predetermined amount of the medicine; and if the second container does not have the first predetermined amount of the medicine, cause the container transfer device to discharge a portion of the medicine in the second container into the first container.

In other features, a medication dispensing system is provided and includes a container transfer device and a controller. The container transfer device is configured to move containers to transfer medicine between containers, where the containers include a first container and a second container, and where the first container is configured to initially store the medicine. The controller is configured to: determine a first predetermined amount of the medicine to be dispensed from the medicine dispensing system; cause to discharge at least a second predetermined amount of the medicine from the first container into the second container; subsequent to the discharge of the at least the second predetermined amount of the medicine, determine whether the second container has greater than or equal to the first predetermined amount of the medicine; and if the second container does not have the first predetermined amount of the medicine, at least one of transfer a portion of the medicine in the second container into the first container or a third container.

In other features, a medication dispensing system is provided and includes a medicine transfer device and a controller. The medicine transfer device is configured to transfer medicine between containers, where the containers include a first container and a second container, and wherein the first container is configured to initially store medicine. The controller is configured to: determine a first predetermined amount of medicine to be dispensed from the medicine dispensing system; cause the medicine transfer device to (i) discharge at least a second predetermined amount of the medicine from the first container onto the medicine transfer device, and (ii) transfer at least a third predetermined amount of the medicine from the medicine transfer device to the second container; subsequent to the transfer of the third predetermined amount of the medicine, determine whether the second container has greater than or equal to the first predetermined amount of the medicine; and if the second container has less than the first predetermined amount of the medicine, cause the medicine transfer device to at least one of (i) transfer at least a portion of the medicine on the medicine transfer device into the second container, or (ii) discharge at least a portion of the medicine in the first container onto the medicine transfer device.

BRIEF DESCRIPTION OF THE DRAWINGS

The above, as well as other advantages of the present disclosure will become readily apparent to those skilled in the art from the following detailed description when considered in light of the accompanying drawings, in which.

DETAILED DESCRIPTION

Figure 1:
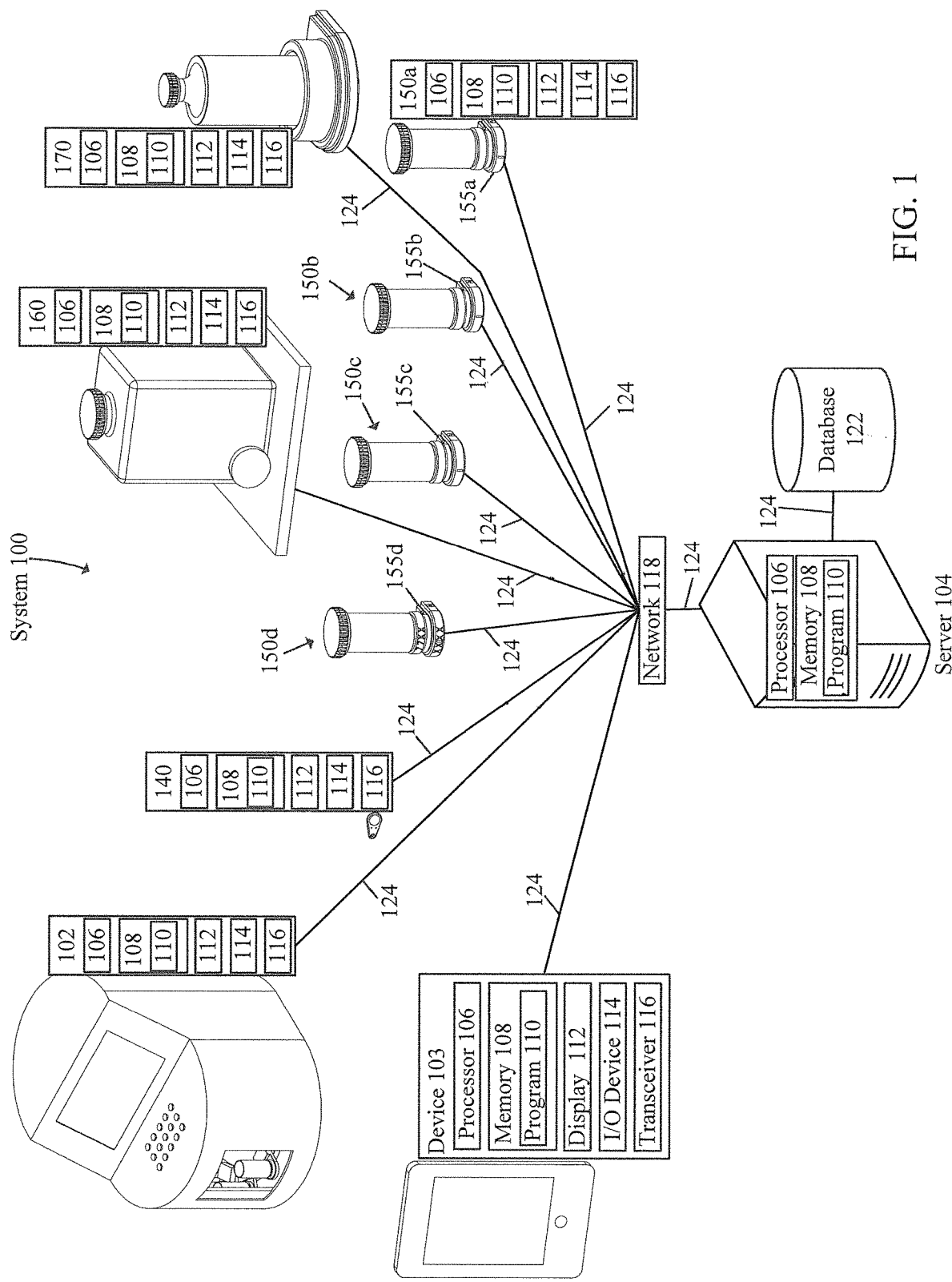
FIG. 1 is a schematic diagram of an exemplary system.

The present disclosure relates to devices supporting medication compliance. The disclosed examples include solid dispensing devices and systems including medication dispensing devices and systems using the same. More specifically, this may include an automatic medicine dispensing system with a portable monitoring device for notifying users when to take their medications and for logging when medications have been taken automatically through a programmable patient apparatus.

The present disclosure includes a system and method and a set of devices which, when used together, assist people in managing either their medications or the medications of somebody they are taking care of. By using the disclosed medicine dispensing method the disclosed device dispenses medications automatically and more accurately than other available dispensing devices, notifying patients when to take specific medications and track the exact dosage taken by a patient at a given time, all while ensuring the notification is for the originally intended medication. For example, by using the prescription data input method of this disclosure, the systems herein may be readily programmable by individual patients. Also, the use of a location tracking method creates a way to remind patients when medications may have been forgotten at home.

Further areas of applicability will become apparent from the description provided herein. It should be understood that the description and specific examples are intended for purposes of illustration only and are not intended to limit the scope of present disclosure.

The following description is merely exemplary in nature and is not intended to limit the present disclosure, application, or uses. It should be understood that throughout the drawings, corresponding reference numerals indicate corresponding parts and features. The terms "device," "unit" and "module" may be used interchangeably. The terms "robot" means a complete robot system and/or different sub-system of the same robot or any type of machines. The term "medicine" means any form of medicine that may include a pill or capsule.

The systems and methods herein may include one or more of a station door or a medicine container loading station door (MCLSD), a storage container or medicine storage container (MSC), a loading station or medicine container loading station (MCLS), a reminder device or medicine reminder unit (MRU), a travel device or medicine travel unit (MTRU), a container transfer device or medicine container transfer unit (MCTU), a storage nest or medicine container storage nest (MCSN), a loading point or medicine container loading point (MCLP), a discharge point or medicine discharge point (MDP), a medicine transfer device or medicine transfer unit (MTU), a medicine container or dispensed medicine container (DMC), a transfer container or medicine transfer container (MTC), an identification device or medicine container identification unit (MCIU), a standard container or original medicine container without cap (OMC), a detecting device or weight detecting device (WDD), an arm tool or end of arm tool (EOAT), an alert device or travel alert unit (TAU), and a checking station or weight checking station (WCS).

Referring now to the figures, FIG. 1 illustrates an exemplary system 100 that is configured to receive, store, monitor, display and transfer medication information. The system 100 may be configured for monitoring the dosage and usage of prescription medication. The system 100 may also be configured to dispense the prescription medication according to required dosages. The system 100 may include a dispensing device 102 and at least one of assemblies 140, 150a-d, 160, and 170. Generally, assembly 140 may be a travel alert device, assemblies 150a-d may be medicine travel devices, and assemblies 160 and 170 may be medicine reminder devices, for example, as described in detail in U.S. patent application Ser. Nos. 15/613,675 and 15/613,852. The dispensing device 102 may include a processor 106, a memory 108 with a program 110 stored thereon, a display 112, at least one input/output (I/O) device 114, and a communication device 116, as described in more detail with respect to FIG. 5.

Medication information may include any information associated with medication or medicine. Medication information may be associated with or include a prescription (e.g., patient name, prescriber name, strength, dosage, quantity, expiration, use directions, or drug or diet interactions), a container type (e.g., shape, size, or color), patient information (e.g., name or history), or a combination thereof. Medication information may include other information associated with a patient or medication.

Prescription information may include medication information associated with a patient or as prescribed or defined by a user such as medical professional or a patient. Container information may include medication information associated with a medication container or according to an identifier on a medication container. As such, the prescription information and container information may or may not match depending on whether the prescription was properly and accurately fulfilled or not. The container information may match the medication information if the content of the medicine container complies with the prescription, and thus the system may generate a notification or alert indicating compliance. The container information may not match the medication information if the contents of the medicine container do not comply with the prescription, and thus the system may generate a notification or alert indicating non-compliance. Accordingly, the systems herein may compare the prescription information and the container information to determine medication compliance or non-compliance.

Embodiments may utilize and compare multiple types of information, e.g., related information received from distinct sources, including, but not limited to, hospitals, pharmacies, doctors' offices, the National Drug Code (NDC), and the like. For example, the system may receive information associated with a prescription (e.g., as defined by a user such as medical professional or patient), a medication or medicine (e.g., as defined by the contents of a medication container or by a manufacturer), and a medication container (e.g., as defined by the size and shape of the container or as labeled on the container). These types of information should be the same if everything was entered and received correctly, but because the information is input separately, the information from various sources may not be the same. For example, errors may be introduced by way of manual inputs, user mismatches, computer transfer, RF reader, OCR, etc. As such, the system herein leverages the information from various sources to increase the accuracy of the medication actually taken by the patient. More specifically, the information is received from distinct sources and compared to determine compliance or non-compliance, thereby reducing the likelihood of error with multiple ways of receiving the same types of information. Depending on whether there is a match or mismatch, the system may alert or notify the user regarding the same to reduce the possibility of the patient taking the wrong medication. Accordingly, the system may be advantageous in increasing the effectiveness of treatment, e.g., by information redundancy and monitoring information with respect to at least two sources.

System 100 may further include at least one of a device 103, a server 104, a network 118, a database 122, and connections 124. An exemplary device 103 may include any computing device including, but not limited to, a mobile device, cellular phone, smart phone, tablet computer, next generation portable device, handheld computer, notebook, or laptop. The device 103 may include a processor 106 that executes program 110 to provide the operations herein. The device 103 may include a memory 108 that stores medication information and program 110. The device 103 may include a communication device 116 that communicates with at least one of the dispensing device 102, the assemblies 150-170, server 104, network 118, and database 122. The device 103 may provide operations to and control the functionality of the dispensing device 102. In addition or alternatively, the dispensing device 102 may be controllable via its own processor 106.

Server 104 may include any computing system. For example, server 104 may include a user profile server for generating and storing a user profile for each user, server 104 may be configured to generate and store medication information. The server 104 may be configured to communicatively connect with and transfer medication information between with respect to any of dispensing device 102 and assemblies 140, 150a-d, 160, and/or 170, network 118, and database 122. Server 104 may be in continuous or periodic communication with dispensing device 102, assemblies 140-170, network 118, and/or database 122. Server 104 may include a local, remote, or cloud-based server or a combination thereof and may be in communication with and provide medication information (e.g., as part of memory 108 or database 122) to any of dispensing device 102, assemblies 102-170, network 118, and/or database 122. The server 104 may further provide a web-based user interface (e.g., an internet portal) to be displayed by display 112. The server 104 may communicate the medication information with dispensing device 102, assemblies 140-170, network 118, and/or database 122 using a notification. In addition, server 104 may be configured to store medication information as part of memory 108 or database 122. Server 104 may include a single or a plurality of centrally or geographically distributed servers 104. Server 104 may be configured to store and coordinate medication information with any portion of the systems herein.

The system 100 may include an overall network infrastructure through which the dispensing device 102, assemblies 140-170, server 104, and database 122 may communicate, for example, to transfer medication information between each other, e.g., using connections 124. In general, a network (e.g., system 100 or network 118) may be a collection of computing devices and other hardware to provide connections and carry communications. As an example, each device may communicate with every other device through the use of a wired or wireless network or a combination thereof, e.g., using any wired or wireless connection including direct wiring, Ethernet wiring, radio frequency (RF), cellular phone service, GPS, Bluetooth, infrared (IR) signals, or any other connection.

The connections 124 may be any wired or wireless connections between two or more endpoints (e.g., devices or systems), for example, to facilitate transfer of medication information. Connections 124 may include a local area network (LAN) connection, for example, to communicatively connect the devices/assemblies 102-170, server 104, and database 122 with network 118. Connections 124 may include a wide area network (WAN) connection, for example, to communicatively connect server 104 with network 118. Connections 124 may include a radiofrequency (RF), near field communication (NFC), Bluetooth®, Wi-Fi, or a wired connection, for example, to communicatively connect assemblies 102-170.

Figure 2:
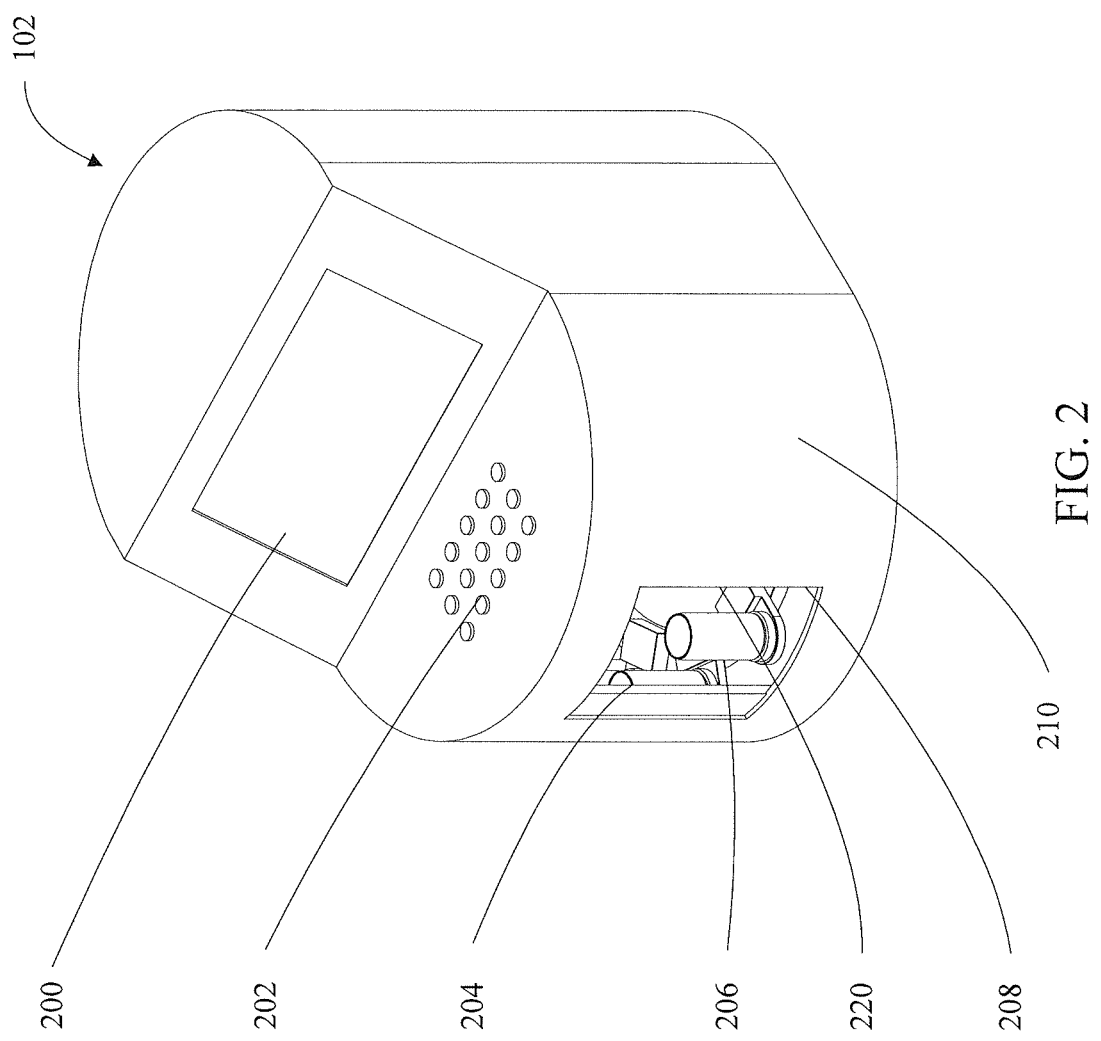
FIG. 2 is a perspective view of an exemplary dispensing unit of the system as shown in FIG. 1.

Referring to FIG. 2, dispenser or dispensing device 102 of FIG. 1 is shown. Dispenser 102 includes a display 200, an input device 202, a loading door or medicine container loading station door (MCLSD) 204, a storage container or medicine storage container (MSC) 206, and a loading station or medicine container loading station (MCLS) 208. Display 200 may be used to present, illustrate or display medication information including, for example, instructions for operation of dispenser 102. The medication information, e.g., on display 200, may include instructions to prepare one or more storage containers 206 having a medical dose for a patient or user. Medicine container loading station 208 may rotate medicine storage container 206 so that a machine vision system or a scanner 220, for instance, to take images (e.g., 360 degree pictures) of medicine storage container 206 to read information from a label on MSC 206. MSC 206 may be operated automatically or manually, may be operated by user inputs to display 200 or a button on a face 210 of dispenser 100, or may be operated via input device 202. Machine vision system 220 may be positioned to view within MCLSD 20.

Figure 3:
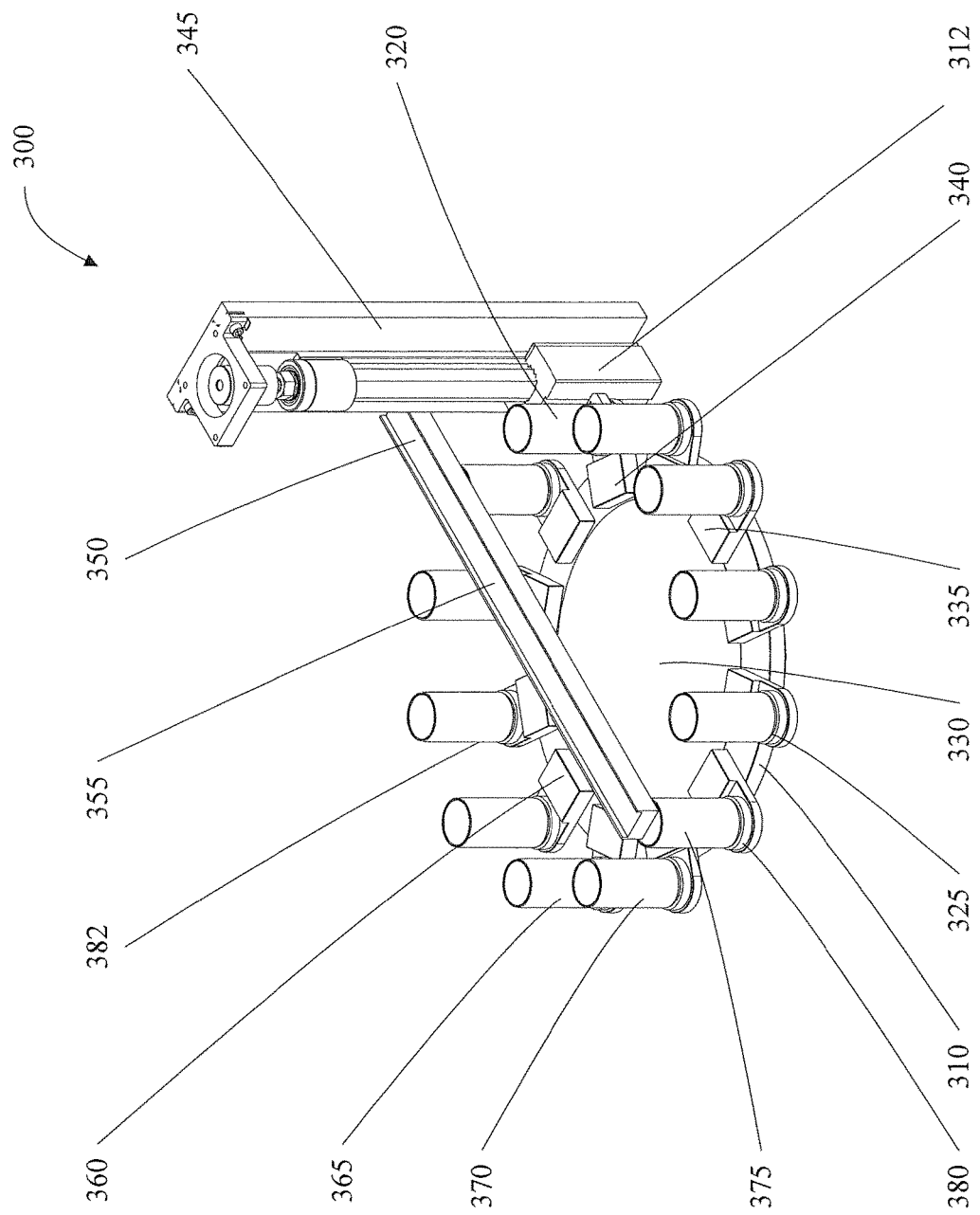
FIG. 3 is a perspective view of an exemplary sub-assembly of the dispensing unit as shown in FIG. 2.
Figure 4B:
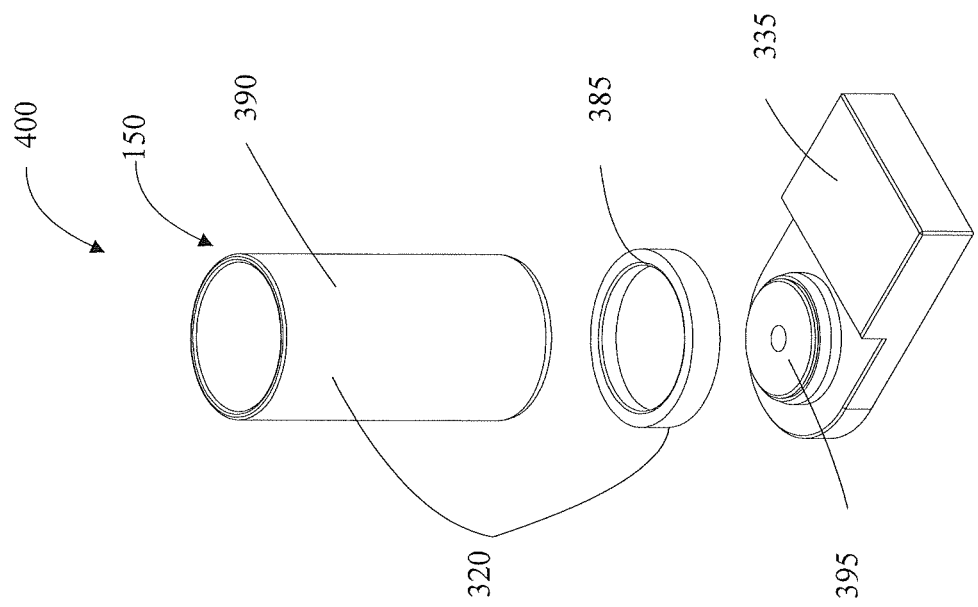
FIG. 4B illustrates the medicine container with storage nest of FIG. 4A in an exploded view.
Figure 4A:
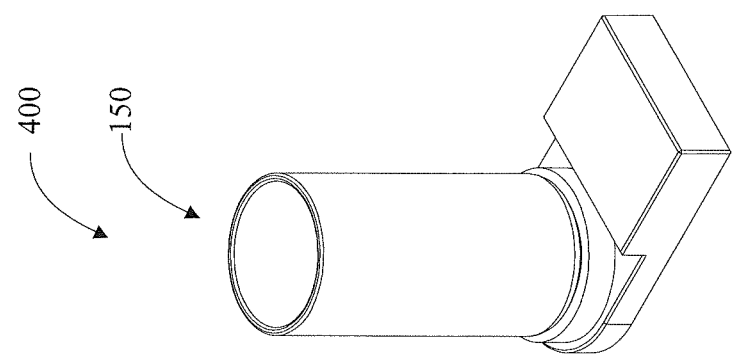
FIG. 4A illustrates a medicine container with a storage nest.

FIG. 3 is a perspective view of an exemplary sub-assembly 300 illustrating the disclosed system or dispenser. Sub-assembly 300 is a view of inside elements of dispenser 102 and includes a carousel 310. Sub-assembly 300 includes a loading station or MCLS 325, a first transfer device or first medicine container transfer unit (MCTU) 330, and a storage device or medicine container storage nest (MCSN) 335. A loading point or medicine container loading point (MCLP) 340 may be proximate a second transfer device or second medicine container transfer unit (MCTU) 345. A first medicine discharge point (MDP) 350 includes, for example, a medicine transfer unit (MTU) 355 that may include a ramp or conveyor for transporting or otherwise conveying medicine from the first medicine discharge point 350 to a second medicine discharge point (MDP) 380. MTU 355 may include one or more devices for measuring a weight or amount of medicine positioned thereon, as will be further described in further examples. Sub-assembly 300 includes weight checking station (WCS) 360, dispensed medicine container (DMC) 365, medicine transfer containers (MTC) 370 and 375. Weight checking station 360 may determine an amount of weight contained thereon. Sub-assembly 300 includes a calibration and verification device 382 to automatically calibrate weight detecting devices. The calibration and verification device 382 may include, but is not limited to, a calibrator, and multiple calibration weights with different masses.

The system may include and utilize one or a plurality of dispensed medicine containers (DMC). For example, a first medicine container may have a final or prescribed dosage for patient to take and a second medicine container may be for system to use to transfer medicine. Medicine transfer unit (MTU), medicine transfer container (MTC), dispensed medicine container (DMC), and medicine storage containers (MSC) may or may not be separated physical devices. The medicine containers may have any shape, size, and may differ from those illustrated. One device or container may have multiple functions. The Medicine Storage Container (MSC) may include an original or standard container received with medicine from pharmacies, hospitals, etc., the medicine storage container may be integrated with or provided with the system, or may be a combination thereof. The medicine transfer unit (MTU) may have different forms and designs, may be a chute, a container of any shape, a plate, a conveyor, a moving surface, a robot, a sub assembly, a machine, although examples of the medicine transfer unit are shown in examples as a linear conveyor and a rotating disc. A medicine quantity sensing unit may include visual sensors, or any monitoring device that may count or otherwise determine a quantity of medicine, and may include scales, load cells, balances, sensors, images, and other means. The medicine container transfer unit (MCTU) moves the medicine containers. The devices herein may have many different forms and designs, including a conveyor, a carousel, a robot, a walking beam, a dial table, a rotary table, a sub assembly, a machine. The systems herein may have multiple layers (such as additional medicine transfer units (MTUs), and may have multiple carousels.

In addition, in one example, containers used are original containers received from, for instance, a pharmacy with the medicine. However, the system may have its own containers and the system transfers medicines from the original containers to the system containers. As such, the system may keep original containers. The disclosed system can transfer medicines back from system containers to original containers if needed, e.g., switch to a different medicine because of, for instance, any allergy to a medicine.

The disclosed system may have a cleaning device to clean the surfaces after dispensing cycle for those surfaces contacted with medicine during the disclosed dispensing processes.

During operation a user may attach medicine container identification unit 385 to original medicine container 390, and together they form medicine storage container 320. Medicine container identification unit 385 may be a physical device, a RF tag, a near field communication (NFC) device, a bar code, a sensor, and the like. Medicine container storage nest 335 is able to communicate wirelessly with medicine container identification unit 385 and can both read and write information. Medicine container storage nest 335 is also able to communicate with the control unit of the dispenser 100, and medicine container storage nest 335 may have, for instance, memory 108.

Referring back to FIG. 3, medicine storage container 320, or original medicine container 390, either of which may have medicine provided from for instance a pharmacy, may be loaded into dispenser 102 from medicine container loading station 325, and medicine storage container 320 is transferred to its storage position by medicine container transfer unit 330. Medicine storage container 320 may include medicine in the form of a pill or a capsule, as examples, and a dose of medicine for a user may include one or more of the pills or capsules. Medicine container transfer unit 330 is illustrated as having carousel 310, but may instead include a conveyor, a robot, or any device that can move medicine storage container 320 from one position to another, and discharge medicine from medicine storage container 320.

Medicine transfer unit 355 moves medicine from one position to another, accepts medicine from medicine storage container 320, and medicine transfer unit 355 also discharges medicine into medicine storage container 320 or any container when positioned at medicine discharge point 380. Medicine transfer unit 355 may have a linear moving surface such as a walking beam, a conveyor, or a rotating surface such as a rotating disc or other shape.

In operation, dispenser 102 moves, via carousel 310, medicine storage container 320 to a loading point 312, and loading point 312 is proximate medicine container transfer unit 345. Medicine container transfer unit 345 engages with medicine storage container 320 by attaching thereto, and moving medicine storage container 320 to first medicine discharge point 350. Medicine storage container 320 is, in one example, a medicine storage container which may have an amount of medicine that is in excess of a dose, or an amount of medicine that is desired to be distributed into dispensed medicine container 365. Medicine container transfer unit 345 turns medicine storage container 320 such that at least a predetermined amount of medicine spills or otherwise pours from medicine storage container 320 onto medicine transfer unit 355. Carousel 310 may rotate to move medicine transfer container 370 to second medicine discharge point 380. When medicine transfer container 370 is positioned at medicine discharge point 380, and when medicine has been discharged onto medicine transfer unit 355, medicine transfer unit 355 thereby conveys the discharged medicine from medicine transfer unit 355 into medicine transfer container 370 until at least a second predetermined amount of medicine is contained in medicine transfer container 370, as determined by weight determining device 395 and medicine container storage nest 335, which weigh and transmit weight information to for instance a controller of dispenser 102. Other methods may be used to determine amount of medicine is contained in medicine transfer container 370, e.g. sensor, and image.

Medicine is transferred from medicine transfer unit 355 into medicine transfer container 370, and a weight of the medicine is determined via weight determining device 395. If the measured weight is less than a given or desired dose, and if medicine is still on medicine transfer unit 355 (i.e., has not been fully discharged), then medicine transfer unit 355 further conveys more medicine into medicine transfer container 370. On the other hand, if no medicine is on medicine transfer unit 355, then additional medicine is discharged to medicine transfer unit 355 from medicine storage container 320. The process of discharging from medicine storage container 320 to medicine transfer unit 355, and from medicine transfer unit 355 to medicine transfer container 370 continues until at least a dose of medicine is contained in medicine transfer container 370. That is, medicine transfer container 370 may include an exact or desired dose, or may include an amount of medicine that is in excess of an exact dose.

If an exact dose is present in medicine transfer container 370, then dispenser 102 operates to convey medicine transfer container 370 to first medicine discharge point 350 via medicine container transfer unit 345, any remaining medicine on medicine transfer unit 355 is discharged back into medicine storage container 320 at second medicine discharge point 380, and the medicine in medicine transfer container 370 is discharged into dispensed medicine container 365 that is positioned at second medicine discharge point 380.

On the other hand, in one example medicine transfer container 370 may include an amount of medicine that is in excess of an exact dose. In such an example, medicine transfer container 370 is thereby conveyed to first medicine discharge point 350 and operations described above are repeated. That is, medicine container transfer unit 345 discharges medicine from medicine transfer container 370 onto medicine transfer unit 355, and medicine transfer container 375 is conveyed via carousel 310 to second medicine discharge point 380. Medicine discharged from medicine transfer container 370 to medicine transfer unit 355 is thereby conveyed to medicine transfer container 375 until at least the exact dose is present in medicine transfer container 375. And, again, if medicine transfer container 375 includes medicine equal to the dose, then the medicine in medicine transfer container 375 is discharged into dispensed medicine container 365, and any excess medicine on medicine transfer unit 355 is returned to medicine storage container 320.

The aforementioned steps continue until a dose of medicine is contained within dispensed medicine container 365, and any additional medicine is returned to medicine storage container 320. In such fashion, dispenser 102 includes a feedback mechanism, ensuring a proper dose, and only a proper dose, is contained in dispensed medicine container 365. That is, feedback is provided in the form of a weight of pills or capsules, corresponding to a dose, measured via weight detecting device 395. The feedback may also be provided in other forms, e.g. pill numbers determined by sensors, images or other check stations. Dispenser 102 is caused to operate using such feedback to ensure that a correct dose is provided in dispensed medicine container 365.

Figure 5:
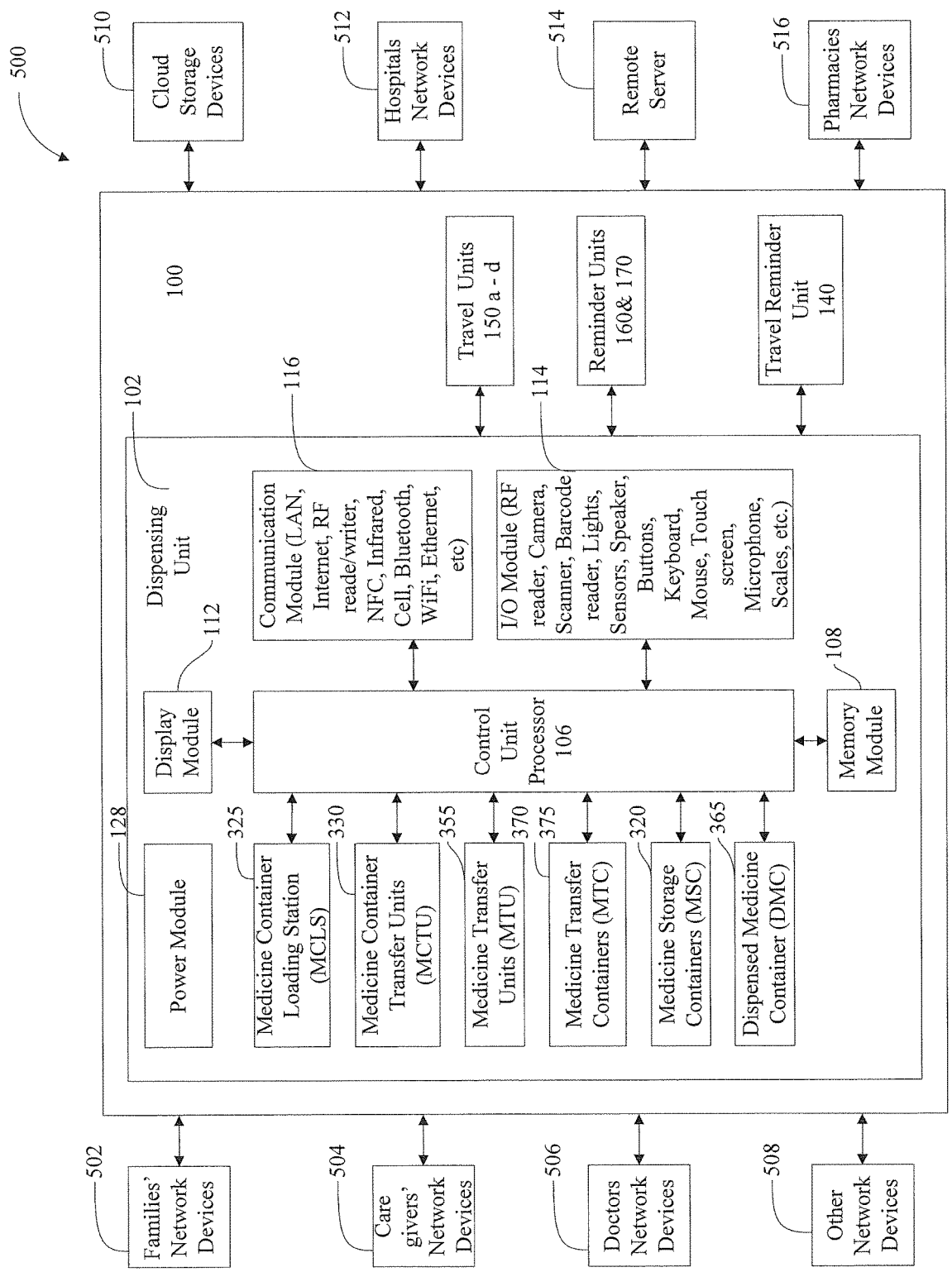
FIG. 5 is a schematic block diagram illustrating an exemplary system.

Referring now to FIG. 5, a schematic diagram of a system 500 of the interaction between system 100, users 502-508, and databases 510-516. The users may include, but are not limited to, family member(s) 502, caregiver(s) 504, doctor(s) 506, and other(s) 508. The databases may include, but are not limited to, cloud storage 510, hospital(s) 512, e.g., hospital servers or databases, remote server(s) 514, which may include, but is not limited to, server 104, National Drug Code (NDC) database(s), and the like, and pharmacy(ies) 516. Information may be retrieved from, stored on, and/or accessed by the databases 510-516.

System 500 may include system 100, including a hardware structure of the dispensing unit 102. The hardware structure may include control unit or processor 106, memory 108, display 112, I/O device(s) 114, communication device 116, and a power device 128. The processor 106 may be any type of general or specific purpose processor, including, but not limited to, a controller. The power device 128 may be configured to either AC and or DC power, such as a lithium ion battery system. If the system 100 uses rechargeable batteries, the power source may monitor the power remaining and give reminder signals to recharge batteries once the batteries are low. The memory 108 may store medication information including prescription information, medicine container identification information and patient's medical history information. The I/O device 114 may include, but is not limited to, an RF reader, one or more cameras, scanner, barcode reader (e.g., 1d or 2d), one or more lights, one or more sensors, one or more speakers, one or more buttons, keyboard, mouse, touch screen, microphone, one or more scales, or a combination thereof.

The communication device 116 may communicatively connect the devices of system 100 or 500, for example, using any type of wired or wireless network connection. The communication device 116 may include a single transceiver or a combination of transmitters and receivers. The wireless network may utilize a wireless transmitter (e.g., cellular, radiofrequency (RF) or Wi-Fi transmitter) of the communication device 116. The communication device 116 may be configured to communicatively connect the dispensing unit 102 with any or all of assemblies 140-170, server 104, and network 118. The communication device 116 may be used for digital or analog signal transfers. For instance, the communication device 116 may include any antenna technology including cellular, V2V communication, radiofrequency (RF), near field communication (NFC), Bluetooth®, Wi-Fi, or the like. The communication device 116 may include any technology that implements a wireless exchange of occupant information by converting propagating electromagnetic waves to and from conducted electrical signals. The communication device 116 may include any technology that is used to exchange medication information wirelessly using radio waves over a radio range or network that enables communication.

Any portion of system 100 or 500, e.g., the dispensing unit 102, assemblies 140-170, server 104, and databases 510-516, may include a computing system and/or device that includes a processor 106, memory 108 and connection 124. Computing systems and/or devices generally include computer-executable instructions, where the instructions may be executable by one or more devices such as those listed below. Computer-executable instructions may be compiled or interpreted from computer programs created using a variety of programming languages and/or technologies, including, without limitation, and either alone or in combination, Java™, C, C++, Visual Basic, Java Script, Perl, SQL, PL/SQL, Shell Scripts, etc. The system 100, e.g., assemblies 102-170 and server 104 may take many different forms and include multiple and/or alternate components and facilities, as illustrated in the Figures further described below. While exemplary systems, devices, and sub-devices are shown in the Figures, the exemplary components illustrated in the Figures are not intended to be limiting. Indeed, additional or alternative components and/or implementations may be used, and thus the above communication operation examples should not be construed as limiting.

In general, computing systems and/or devices (e.g., dispensing unit, assemblies 140-170, server 104, databases 512-516) may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., the BlackBerry OS distributed by Research In Motion of Waterloo, Canada, and the Android operating system developed by the Open Handset Alliance. Examples of computing systems and/or devices such as device 103 and server 104 may include, without limitation, mobile devices, cellular phones, smart-phones, super-phones, tablet computers, next generation portable devices, mobile printers, handheld computers, notebooks, laptops, secure voice communication equipment, networking hardware, computer workstations, or any other computing system and/or device.

Further, processor 106 may include a microprocessor. Processor 106 may receive instructions from memories such as memory 108, database 122, or cloud storage 510 and execute the instructions, thereby performing one or more operations or processes including those described herein. Such instructions and other medication information may be stored and transmitted using a variety of computer-readable mediums (e.g., memory 108, database 122, or cloud storage 510). Processors such as processor 106 may include any computer hardware or combination of computer hardware that is configured to accomplish the purpose of the devices, systems, and processes described herein. For example, the processor 106 may be any one of, but not limited to single, dual, triple, or quad core microprocessors (on one single chip), graphics processing devices, visual processing devices, and virtual processors.

Memories such as memory 108 or database 122 may include, in general, any computer-readable medium (also referred to as a processor-readable medium) that may include any non-transitory (e.g., tangible) medium that participates in providing medication information or instructions that may be read by a computer (e.g., by the processors 106 of the assemblies 102-170 and server 104). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including radio waves, metal wire, fiber optics, and the like, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Further, databases, data repositories or other medication information stores (e.g., memory 108, database 122, or cloud storage 510) described herein may generally include various kinds of mechanisms for storing, providing, accessing, and retrieving various kinds of medication information, including a hierarchical database, a set of files in a file system, an application database in a proprietary format, a relational database management system (RDBMS), etc. Each such medication information store may generally be included within (e.g., memory 108) or external (e.g., database 122 or cloud storage 510) to a computing system and/or device (e.g., dispensing unit 102, assemblies 140-170, server 104, or databases 512-516) employing a computer operating system such as one of those mentioned above, and/or accessed via a network (e.g., system 100 or 500, or network 118) or connection in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above. Memory 108 and database 122 may be connected to or part of any portion of system 100.

Figure 6:
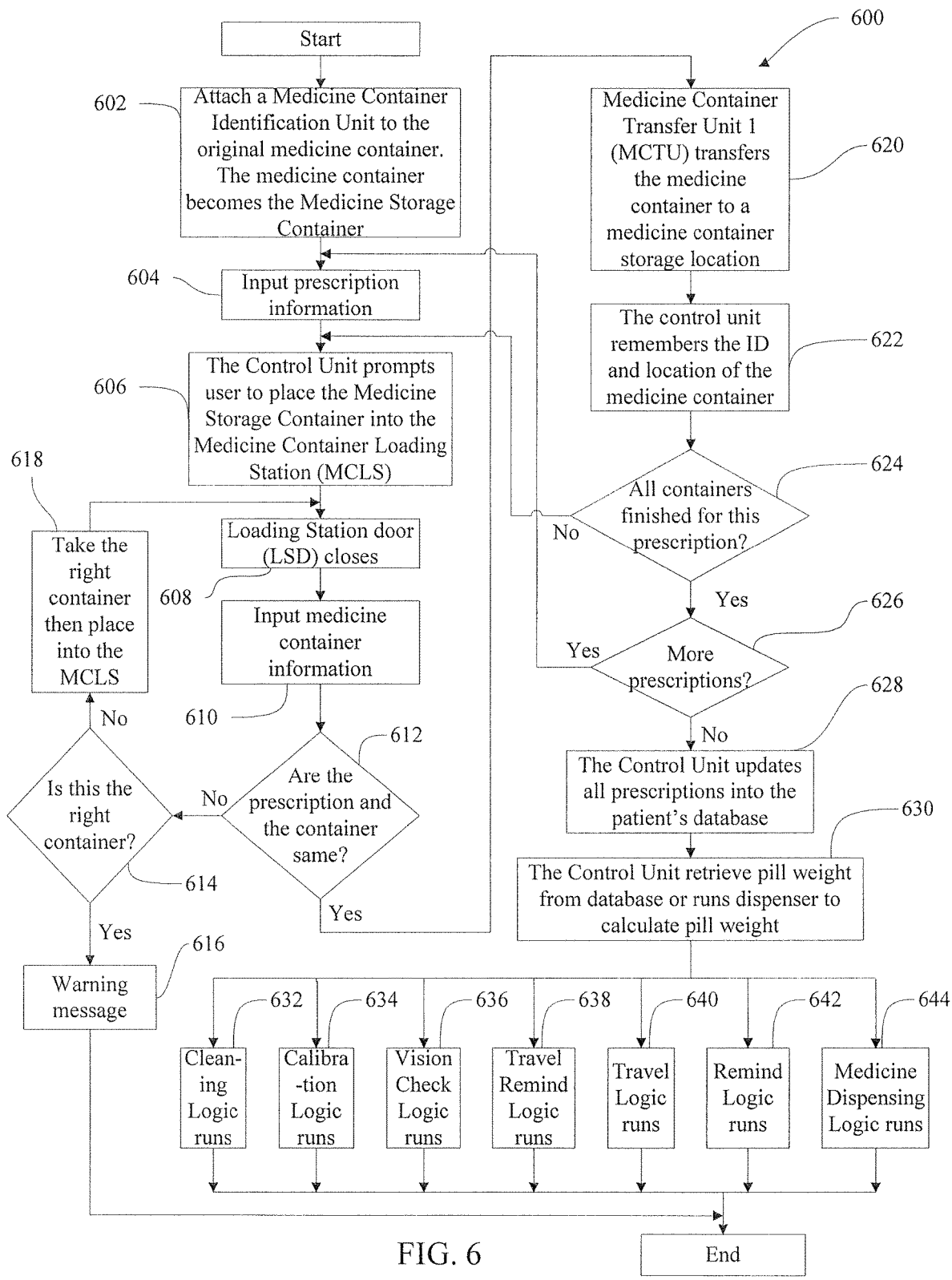
FIG. 6 is a flow diagram illustrating an exemplary process for setting up the system of FIG. 1 for operation.

Referring now to FIG. 6, a flow diagram of an exemplary process 600 for setting up the system 100 is illustrated. Process 600 may include operations that may be part of program 110 stored on memory 108, and/or executed by processor 106. Process 600 may take many different forms and include multiple and/or alternate steps. While an exemplary process is shown, the exemplary steps illustrated are not intended to be limiting. Indeed, additional or alternative steps and/or implementations may be used.

Process 600 may begin at block 602 at which a medicine container identification unit 385 is added to an original medicine container 390. The combination of the medicine container identification unit 385 and the medicine container 390 collectively form the medicine storage container 320. Alternatively, process 600 may implement the original medicine container 390 without the medicine container identification unit 385.

Figure 7:
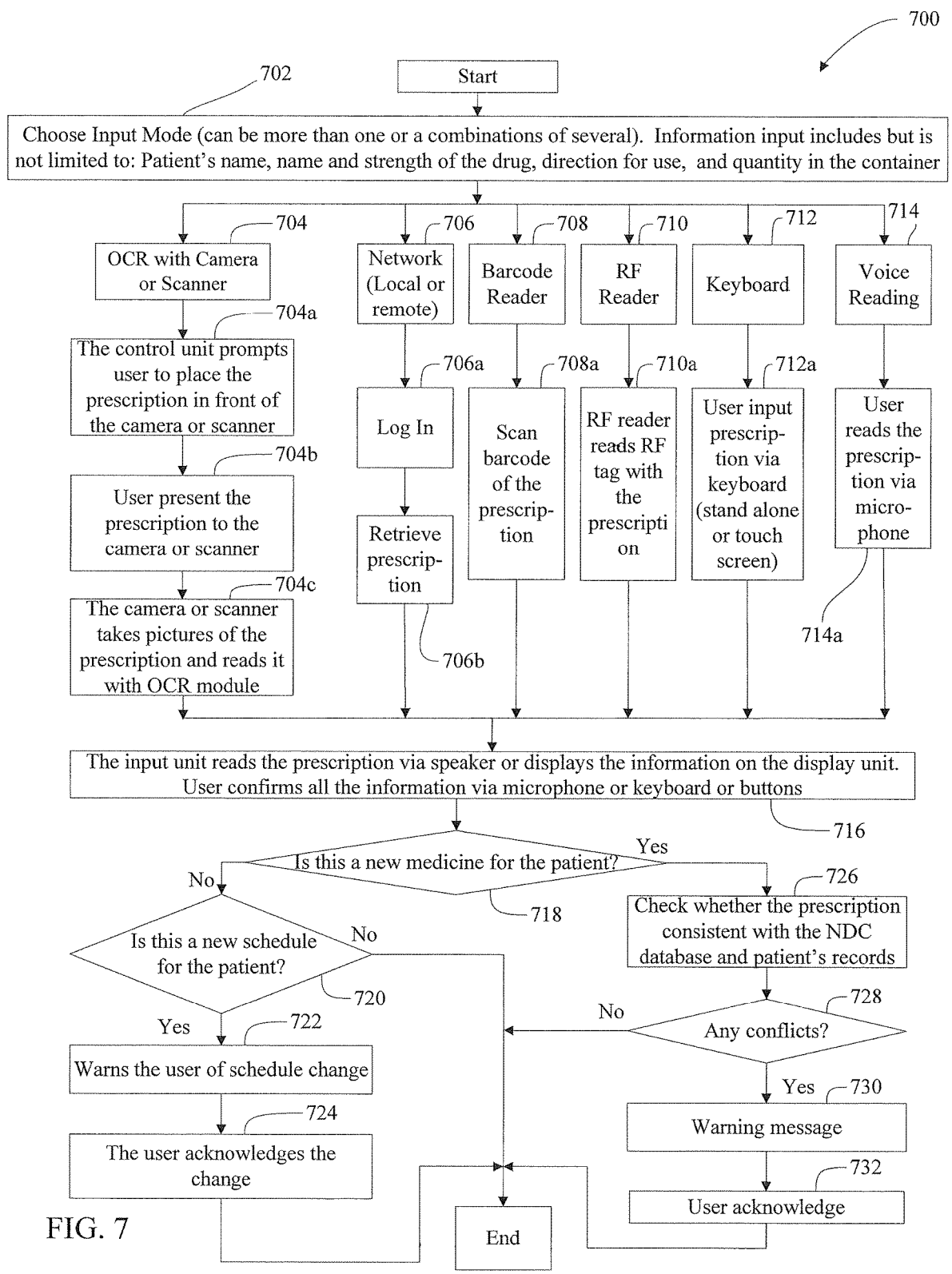
FIG. 7 is a flow diagram illustrating an exemplary process for inputting prescription information.

At block 604, prescription information associated with the patient may be inputted into the device 100. The information may include, but is not limited to, the patient's name, name of the drug, strength of the drug, direction for use, including, but not limited to, a schedule and/or quantity to take, quantity in the medicine container 390, and the like. The information may be inputted via different methods and/or technologies, as illustrated in FIG. 7 and described below.

At block 606, the processor 106 may prompt the user to place the medicine storage container 320 into the loading station 325. The prompt may be verbal, for example, via speaker(s) of the I/O device(s) 114, and/or visual, for example, via the display 112. The user may then place the medicine storage container 320 into the loading station 325.

At block 608, the loading station door 204 may close. This may be done automatically, for example, but not intended to be limiting, after a set amount of time has passed after the prompt to place the medicine storage container 320 into the loading station 325, or upon sensing that the medicine storage container 320 has been placed into the loading station 325. Alternatively, the loading station door 204 may be manually closed by the user, for example, but not intended to be limiting, sliding the door closed or pressing a button designated for closing and/or opening the door.

Figure 8:
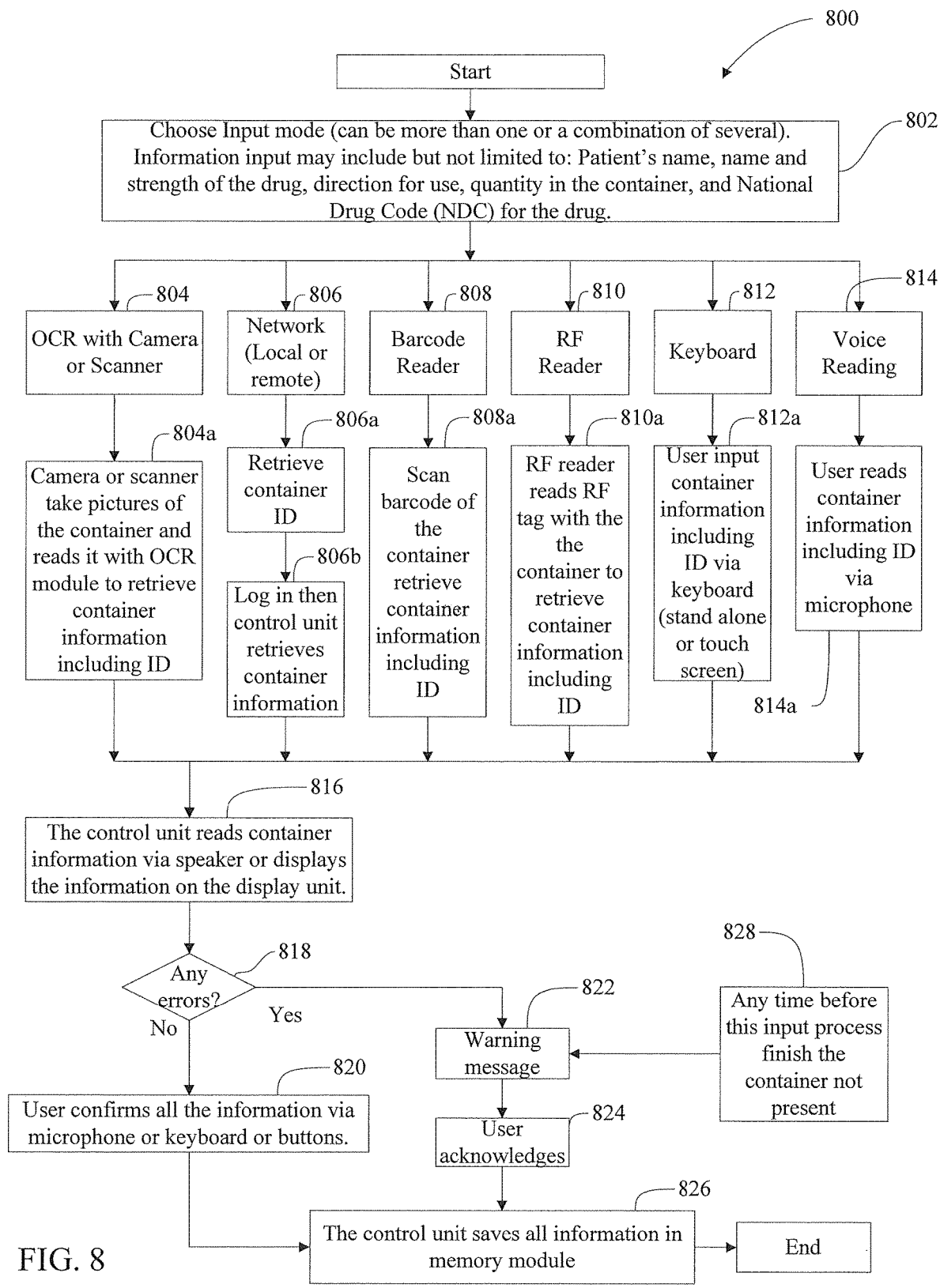
FIG. 8 is a flow diagram illustrating an exemplary process for inputting medicine container information.

At block 610, medicine container information may be inputted. The information may include, but is not limited to, the patient's name, name of the drug, strength of the drug, direction for use, including, but not limited to, a schedule and/or quantity to take, quantity in the medicine container 390, and NDC information for the medicine/drug. The information may be inputted via different methods and/or technologies, as illustrated in FIG. 8 and described below.

At block 612, the processor 106 may determine if the prescription and the medicine storage container 320 match, for example, by comparing the prescription information and the medicine container information. If they do not match, process 600 may proceed to block 614 at which the processor 106 may prompt the user to check if the medicine storage container 320 is correct.

If the medicine storage container 320 is correct, process 600 may proceed to block 616 at which the processor 106 may provide a warning message, verbally and/or visually, for example, of the discrepancy between the prescription and the medicine storage container 320, after which process 600 may end.

If the medicine storage container 320 is not correct, process 600 may proceed to block 618 at which the processor 106 may prompt the user to take the correct medicine storage container 320, which includes the correct medicine container 390, and place it into the loading station 325 after removing the incorrect medicine storage container 320. Process 600 may then proceed back to block 608 at which the loading station door 204 may be closed. Blocks 610 and 612 may be repeated.

Referring back to block 612, if the prescription and the medicine storage container 320 do match, then process 600 may proceed to block 620 at which a first medicine container transfer unit 330 of the dispensing unit 102 may transfer the medicine storage container 320 to a storage location.

At block 622, the processor 106 may remember the container identification and the storage location of the medicine storage container 320, for example, by storing the information in the memory 108.

At block 624, the processor 106 may determine if all medicine storage containers 320 and/or medicine containers 390 for the prescription are finished. This may be determined from the prescription information obtained at block 604. In addition or alternatively, the processor 106 may prompt the user, verbally and/or visually, if all medicine storage containers 320 for the prescription are finished, to which the user may respond tactilely and/or verbally. If the answer is no, process 600 may proceed back to 606 at which the processor 106 may prompt the user to place the next medicine storage container 320 into the loading station 325, after which the subsequent blocks of process 600 may be repeated.

If all the containers are finished for the prescription, process 600 may proceed to block 626 at which the processor 106 may prompt the user, verbally and/or visually, if there are any more prescriptions, to which the user may respond tactilely and/or verbally. If there are more prescriptions, process 600 may proceed back to block 604 at which the prescription information for the new prescription may be inputted into the device 100, after which the subsequent blocks of process 600 may be repeated.

If there are no more prescriptions, process 600 may proceed to block 628 at which the control unit processor may update the prescription(s) into the patient's account, which, again, may be stored locally in the memory 108 and/or remotely at any one of the databases 510-516.

At block 630, the processor 106 may retrieve weight for each pill or capsule from databases 510-516. Alternatively processor may run dispenser unit to calculate the weight. The processor 106 may also check the weight of the medicine in a container to verify the medicine in the container is correct.

At block 632, the processor 106 may run cleaning logic to clean surfaces contact with medicine according predetermined schedules or as required.

At block 634, the processor 106 may run calibration and verification logic to calibrate or verify weight detecting devices according to predetermined schedules as required.

At block 636, the processor 106 may run vision system logic to take images of a medicine and compare them to the image retrieve from databases 510-516 to verify medicine in the container is correct.

At blocks 638-642, any one of the assemblies 140, 150a-d, 160, and 170 and the dispensing unit 102 may now operate according to any one of the processes described in U.S. patent application Ser. Nos. 15/613,675 and 15/613,852.

At block 644, the processor 106 runs dispenser logic as described herein. After block 644, the process may repeat or end.

Referring now to FIG. 7, a flow diagram of an exemplary process 700 for inputting prescription information is illustrated. Process 700 may include operations that may be part of program 110, stored on memory 108, and/or executed by processor 106, Process 700 may take many different forms and include multiple and/or alternate steps. While an exemplary process is shown, the exemplary steps illustrated are not intended to be limiting. Indeed, additional or alternative steps and/or implementations may be used.

Process 700 may begin at block 702 at which the user may choose at least one input mode 704-714 based at least on the I/O device(s) 114 incorporated in the dispensing unit 102.

Input mode 704 may include obtaining the prescription information via OCR, for example, but not intended to be limiting, where the I/O device(s) 114 includes a machine vision system (e.g., at least one camera) and/or a scanner. As merely one exemplary approach, at block 704a, the processor 106 may prompt a user to present the prescription, which may include the prescription information, to the camera(s) or scanner. The prompt may include any auditory and/or visual indicator(s), for example, on the display 112, the indicator(s) including, but not limited to, specific text instructions to present the prescription, text that the camera(s) or scanner are ready, lights, sounds, and the like. At block 704b, the user may present the prescription to the camera(s) or scanner. This may include, but is not limited to, placing the prescription in front of or inside of the camera(s) or scanner, feeding the prescription into the camera(s) or scanner, and the like. At block 704c, the camera(s) or scanner may take pictures of or scan the prescription, and the I/O device(s) 114 may read the text of the picture or scanned image of the prescription via an OCR device. In addition or alternatively, the I/O device(s) 114 may transmit the picture(s) or scanned image to the processor 106, which may in turn read the text via an OCR device.

Input mode 706 may include obtaining the prescription information from a network, either local or remote. At block 706a, the user may log in to an account, which may be associated with the patient and may include the prescription information, via an input device of the I/O device(s) 114, including, but not limited to, a keyboard, a keypad, a touch screen, a microphone, a fingerprint scanner, an eye scanner, a facial recognition camera, and the like. The patient log in information and/or the prescription regiment data may be stored locally on the memory 108 and/or remotely, including, but not limited to, any one of the databases 510-516. At block 706b, the processor 106 may retrieve the prescription information from the account.

Input mode 708 may include obtaining the prescription information via a barcode reader or scanner of the I/O device(s) 114. At block 708a, the barcode reader/scanner may scan a barcode of the prescription.

Input mode 710 may include obtaining the prescription information via an RF reader of the I/O device(s) 114. At block 710a, the RF reader may read an RF tag of the prescription.

Input modes 712 and 714 may include obtaining the prescription information via direct input from the user, for example, tactilely or verbally. With respect to input mode 712, the user may input the prescription information via a keyboard of the I/O device(s) 114, which may be a standalone keyboard or a touch screen keyboard incorporated in the display 112, as illustrated in block 712a. With respect to input mode 714, the user may read the prescription via a microphone of the I/O device(s) 114, as illustrated in block 714a.

At block 716, the processor 106 may present the prescription information back to the user verbally and/or visually. For example, the processor 106 may read the prescription information via speaker(s) of the I/O device(s) 114 and/or display the prescription information on the display 112. The user may then verify the information tactilely, for example, via a keyboard of the I/O device(s) 114, which, again, may be a standalone keyboard or a touch screen keyboard, and/or verbally, for example, via a microphone of the I/O device(s) 114.

At block 718, the processor 106 may determine if the medicine is new for the patient. This may be determined by prompting the user, which, again, may be verbally via speaker(s) of the I/O device(s) 114, or visually on the display 112. In addition or alternatively, the processor 106 may compare the name of the medicine with a list of prior and/or current medicines stored in the patient's account.

If the medicine is not new, process 700 may proceed to block 720 at which the processor 106 may determine if the schedule included with the prescription information is new. This, again, may be determined by prompting the user and/or comparing the schedule to an existing schedule stored in the patient's account. If the schedule is not new, process 700 may end. If the schedule is new, process 700 may proceed to block 722 at which the processor 106 may warn the user of the schedule change, and block 724 at which the user may acknowledge the change, after which process 700 may end.

If the medicine is new, process 700 may proceed to blocks 726 and 728 at which the processor 106 may check whether the prescription information is consistent with the NDC database(s) and/or the patient's records, and determine if there are any conflicts. If there are no conflicts, then process 700 may end. If there are conflicts, process 700 may proceed to blocks 730 and 732 at which the processor 106 may provide a warning message, verbally and/or visually, and the user may acknowledge the warning, tactilely or verbally, after which process 700 may repeat or end.

Referring now to FIG. 8, a flow diagram of an exemplary process 800 for inputting the medicine container information is illustrated. Process 800 may include operations that may be part of program 110, stored on memory 108, and/or executed by processor 106. Process 800 may take many different forms and include multiple and/or alternate steps. While an exemplary process is shown, the exemplary steps illustrated are not intended to be limiting. Indeed, additional or alternative steps and/or implementations may be used.

Process 800 may begin at block 802 at which the user may choose at least one input mode 804-814 based at least on the I/O device(s) 114. Input modes 804-814 may be similar to input modes 704-714 described above.

Input mode 804 may include obtaining the medicine container information via OCR, for example, but not intended to be limiting, where the I/O device(s) 114 includes a machine vision system (e.g., at least one camera) and/or a scanner, which may be the same or different from the camera(s) or scanner used in input mode 704. At block 804a, the camera(s) or scanner may take pictures of or scan the medicine container 390, e.g., a label on the medicine container 390. The I/O device(s) 114 may then read the text of the picture or scanned image of the medicine storage container 320 via an OCR device to retrieve the medicine container information, including, but not limited to, the container ID. In addition or alternatively, the I/O device(s) 114 may transmit the picture(s) or scanned image to the processor 106, which may in turn read the text via an OCR device.

Input mode 806 may include obtaining the medicine container information from a network, either local or remote. At block 806a, the processor 106 may retrieve an ID of the container. At block 806b, the user may log in to an account that may have access to certain databases that include the medicine container information, and that may be stored locally, for example, on the memory 108, and/or remotely, including, but not limited to, any one of the databases 510-516. The log in information may be input by the user via an input device of the I/O device(s) 114, including, but not limited to, a keyboard, a keypad, a touch screen, a microphone, a fingerprint scanner, an eye scanner, a facial recognition camera, and the like. After logging in, the processor 106 may then retrieve the medicine container information from the database(s) on which it is stored.

Input mode 808 may include obtaining the medicine container information via a barcode reader or scanner of the I/O device(s) 114. At block 808a, the barcode reader/scanner may scan a barcode of the medicine storage container 320 to retrieve the container information, including, but not limited to, the container ID.

Input mode 810 may include obtaining the medicine container information via a RF reader of the I/O device(s) 114. At block 810a, the RF reader may read an RF tag on the medicine storage container 320 to retrieve the container information, including, but not limited to, the container ID.

Input modes 812 and 814 may include obtaining the medicine container information, including, but not limited to, the container ID, via direct input from the user, for example, tactilely or verbally. With respect to input mode 812, the user may input the medicine container information via a keyboard of the I/O device(s) 114, which may be a standalone keyboard or a touch screen keyboard, as illustrated in block 812a. With respect to input mode 814, the user may read the prescription via a microphone of the I/O device(s) 114, as illustrated in block 814a.

At block 816, the processor 106 may present the medicine container information to the user verbally and/or visually for confirmation of its accuracy. For example, the processor 106 may read the medicine container information via speaker(s) of the I/O device(s) 114 and/or the display 112 may display the data. The user may then verify the information tactilely, for example, via a keyboard of the I/O device(s) 114, which, again, may be a standalone keyboard or a touch screen keyboard, and/or verbally, for example, via a microphone of the I/O device(s) 114.

At block 818, the user may determine whether or not there are any errors in the medicine container information. If there are no errors, process 800 may proceed to block 820 at which the user may confirm the accuracy of the medicine container information verbally, for example, via a microphone of the I/O device(s) 114 and/or tactilely, for example, via a keyboard and/or button(s). If there are any errors, process 800 may proceed to blocks 822 and 824 at which the processor 106 may provide a warning message, verbally and/or visually, and the user may acknowledge the warning, tactilely or verbally.

At block 826, the processor 106 may store the medicine container information, for example, locally in the memory device 108, after which process 800 may end.

At block 828, the processor 106 monitors presentation of the medicine container. If it was removed from the unit, the system will give warning signal.

After block 828, the process may repeat or end.

Figure 9A:
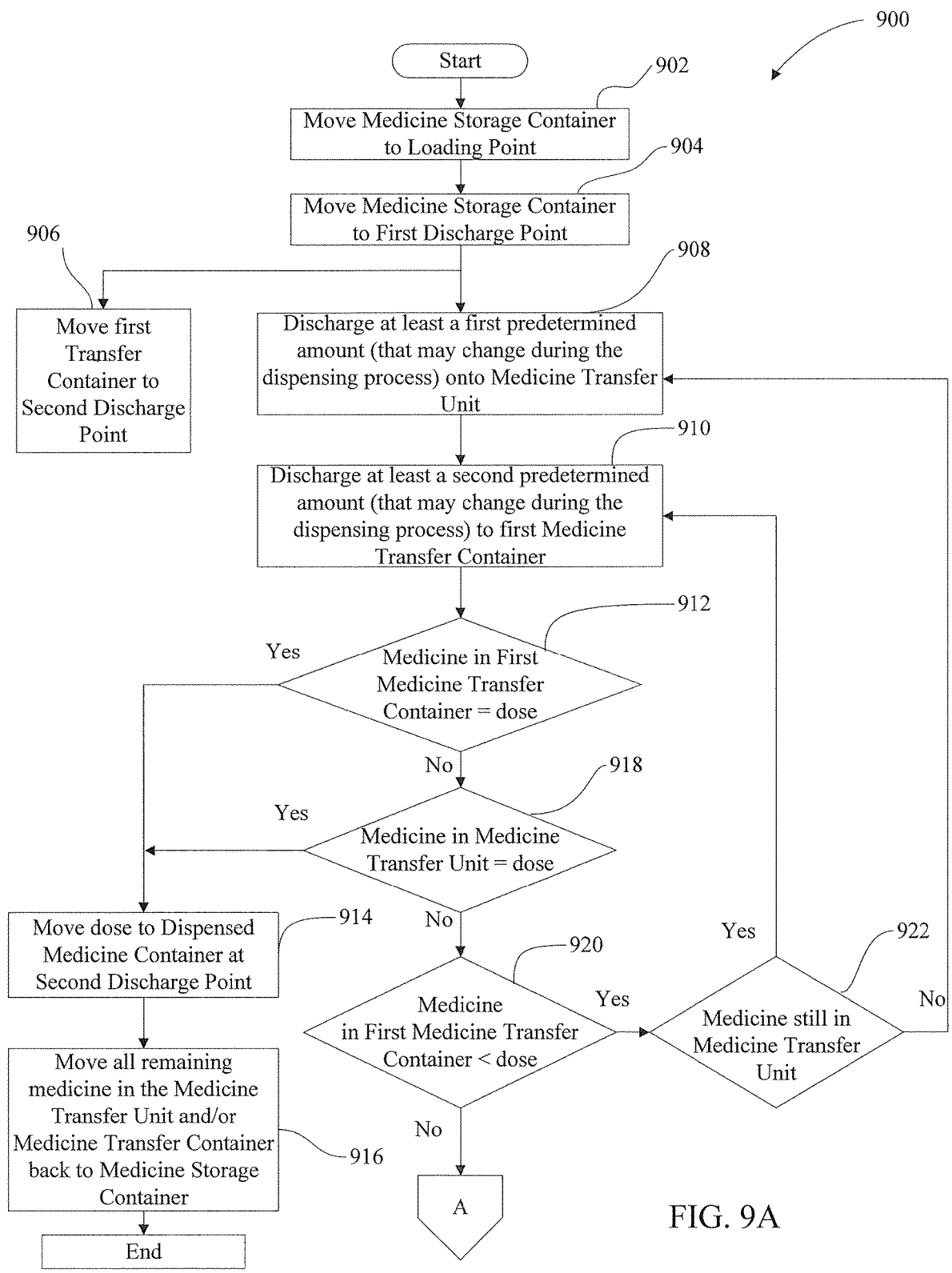
FIG. 9A is a flow diagram illustrating an exemplary process for dispensing a dose of medicine.
Figure 9B:
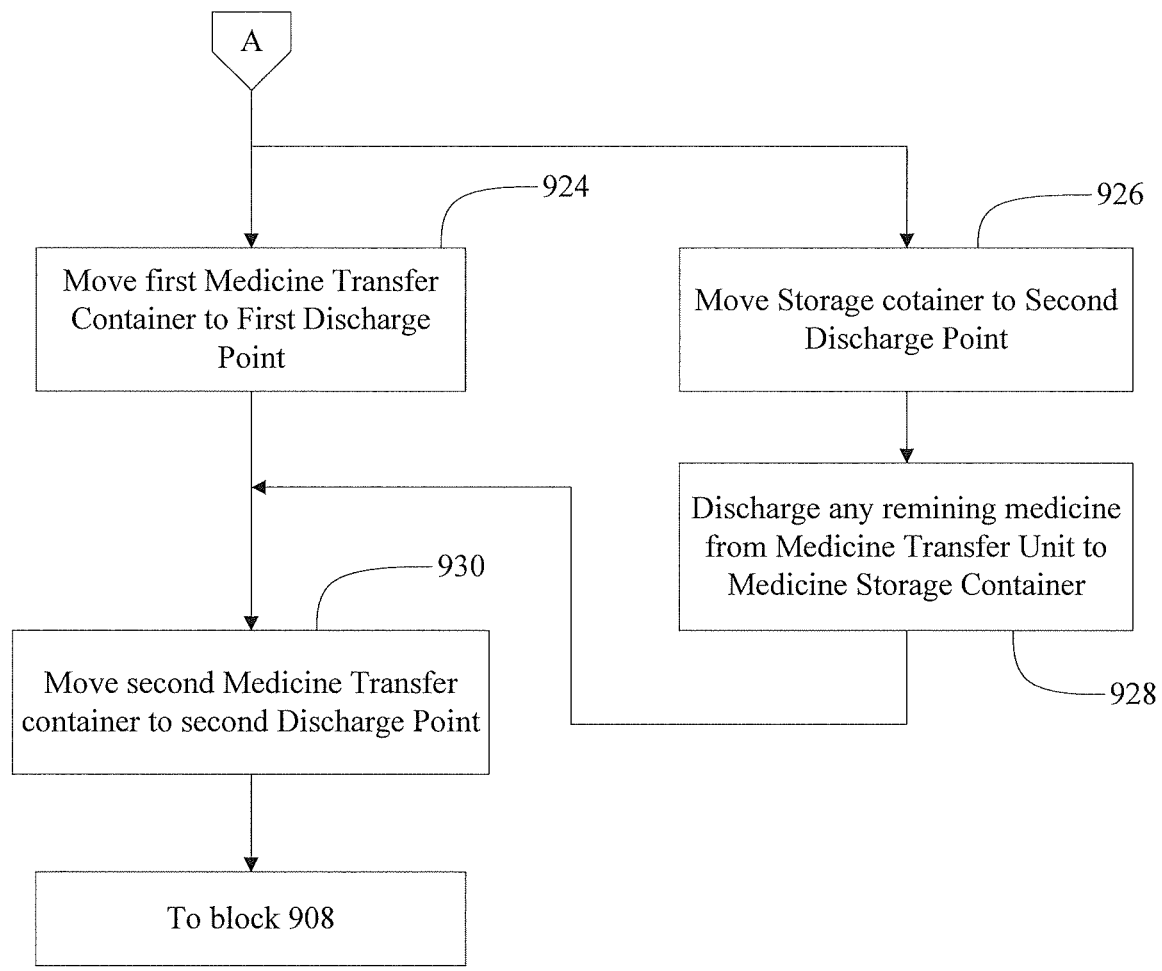
FIG. 9B is a flow diagram illustrating an exemplary process for continuing to iterate beyond FIG. 9A for dispensing a dose of medicine.

Referring now to FIGS. 9A and 9B, a flow diagram of an exemplary process 900 is illustrated. Process 900 may be for operating the dispensing unit 102, e.g., moving a dose (or other predetermined amount) of medicine to a dispensed medicine container. Process 900 may include operations that may be part of program 110, stored on memory 108 or database 122, and/or executed by processor 106. Process 900 may take many different forms and include multiple and/or alternate steps. While an exemplary process is shown, the exemplary steps illustrated are not intended to be limiting. Indeed, additional or alternative steps and/or implementations may be used. In addition, process 900 may be applicable, in whole or in part, to each of processes 1000, 1200, 1400, 1600, 1800, 2000, and 2200 and the specific embodiments of the dispensing unit 102 incorporated therein, as described in more detail hereinafter.

At block 902, processor 106, e.g., by way of medicine container transfer unit 330, may move the medicine storage container 320 from an initial position, e.g., the storage position, to the medicine container loading point 340, which may be stored on and received from memory 108 or database 122. The moving of the medicine storage container 320 may be performed by the first medicine container transfer unit 330, and may generally be in a circumferential direction, as illustrated in FIG. 3. However, it should be appreciated that the medicine storage container 320 may be moved to the loading point 340 in any linear or non-linear direction.

At block 904, the processor 106 may move, e.g., by way of the medicine container transfer unit 345, the medicine storage container 320 from the loading point 340 to a first discharge point 350, which may be stored on and received from memory 108 or database 122.

At block 906, the processor 106 may move, e.g., by way of the medicine container transfer unit 330, a first medicine transfer container, which may be either medicine transfer container 370 or 375 from an initial position to a second discharge point 380, which, as explained above, may be located at an end of the medicine transfer unit 355 to receive the medicine. The moving of the first medicine transfer container 370, 375 generally may be in a circumferential direction, as illustrated in FIG. 3. However, it should be appreciated that the first medicine transfer container 370, 375 may be moved to the second discharge point 380 in a linear direction.

At block 908, the processor 106 may discharge, e.g., by way of the medicine container transfer unit 345, at least a first predetermined amount of medicine from the medicine storage container 320 onto the medicine transfer unit 355. The predetermined amount may change during the dispensing process. It should be appreciated that the processor 106 may discharge the medicine from the medicine storage container 320 via any known mechanism or device, which may rotate, tilt, or otherwise move the medicine storage container 320.

At block 910, the processor 106 may discharge, e.g., by way of the medicine transfer unit 355, at least a second predetermined amount of the medicine on the medicine transfer unit 355 therefrom into the medicine transfer container 370, 375. The second predetermined amount may or may not be the same as the first predetermined amount, and may change during the dispensing process.

At block 912, the dispensing unit 102, by way of the processor 106 and feedback from check stations, may determine if the medicine in the first medicine transfer container 370, 375 is equal to the required dosage, as determined and stored in the memory 108 in process 600. If the medicine does equal the required dosage, then process 900 may proceed to blocks 914 and 916. If not, then process 900 may proceed to block 918.

At block 914, the processor 106 may move, e.g., by way of the medicine transfer unit 355, the medicine in the first medicine transfer container 370, 375, which is in the required dosage amount, to the dispensed medicine container 365 at the second discharge point 380.

At block 916, the processor 106 may move, e.g., via the medicine transfer unit 355, all the remaining medicine on the medicine transfer unit 355 and/or the first medicine transfer container 370, 375 back to the medicine storage container 320 by various rearranging of the dispensed medicine container 365 and medicine storage container 320 from and to the second medicine discharge point 380. Process 900 may end after block 916.

At block 918, the dispensing unit 102, for example, the processor 106, may determine if the medicine on the medicine transfer unit 355 is equal to the required dosage. If the medicine does equal the required dosage, then process 900 may proceed to blocks 914 and 916 described above. If not, then process 900 may proceed to block 920.

At block 920, the dispensing unit 102, for example, the processor 106, may determine if the medicine in the first medicine transfer container 370, 375 is less than the required dosage. If it is less, then process 900 may proceed to block 922 at which the dispensing unit (e.g., the processor 106) may determine if there is still medicine on the medicine transfer unit 355. If there is not, process 900 may go back to block 908. If there is, process 900 may go back to block 910.

If the medicine in the first medicine transfer container 370, 375 is not less than the required dosage, as may be determined at block 920, process 900 may proceed to blocks 924 and 926 at which the processor 106 may move the medicine storage container 320 to the second discharge point 380, and the first medicine transfer container 370, 375 to the first discharge point 350. Blocks 924 and 926 may occur simultaneously or one after the other.

At block 928, the processor 106 may discharge any remaining medicine on the medicine transfer unit 355 into the medicine storage container 320.

At block 930, the processor 106 may move a second medicine transfer container, which may be the other of medicine transfer containers 370 and 375, to the second discharge point 380.

After block 930, process 900 may go back to block 908, where the first medicine transfer container 370, 375 may act as the medicine storage container 320, and the second medicine transfer container 370, 375 may act as the first medicine transfer container 370, 375. Accordingly, medicine may be discharged from the first medicine transfer container 370, 375 to the second medicine transfer container 370, 375, and medicine storage container 320.

Process 900 may be iterated until the medicine in the dispensed medicine container 365 equals the required dosage, as described below.

In general, the processes herein (e.g., process 900) may involve different combinations of medicine in one or two units. The combinations may include, but are not limited to, the first medicine transfer container 370, 375 alone, the second medicine transfer container 370, 375 alone, the medicine transfer unit 355 alone, the first and second medicine transfer containers 370, 375, the first medicine transfer container 370, 375 and the medicine transfer unit 355, and the second medicine transfer container 370,375 and the medicine transfer unit 355. Those combinations may change for every iteration. The process 900 determines the most optimal way to dispense for every iteration.

As described in more detail with respect to processes 1000, 1200, 1400, 1600, 1800, 2000, and 2200, the processor 106 may communicate with, i.e., send commands to, receive data from, and the like, to various components of the dispensing unit 102 and/or system 500 to perform the different steps of process 900. In addition or alternatively, the various components may communicate directly with each other.

Figure 10:
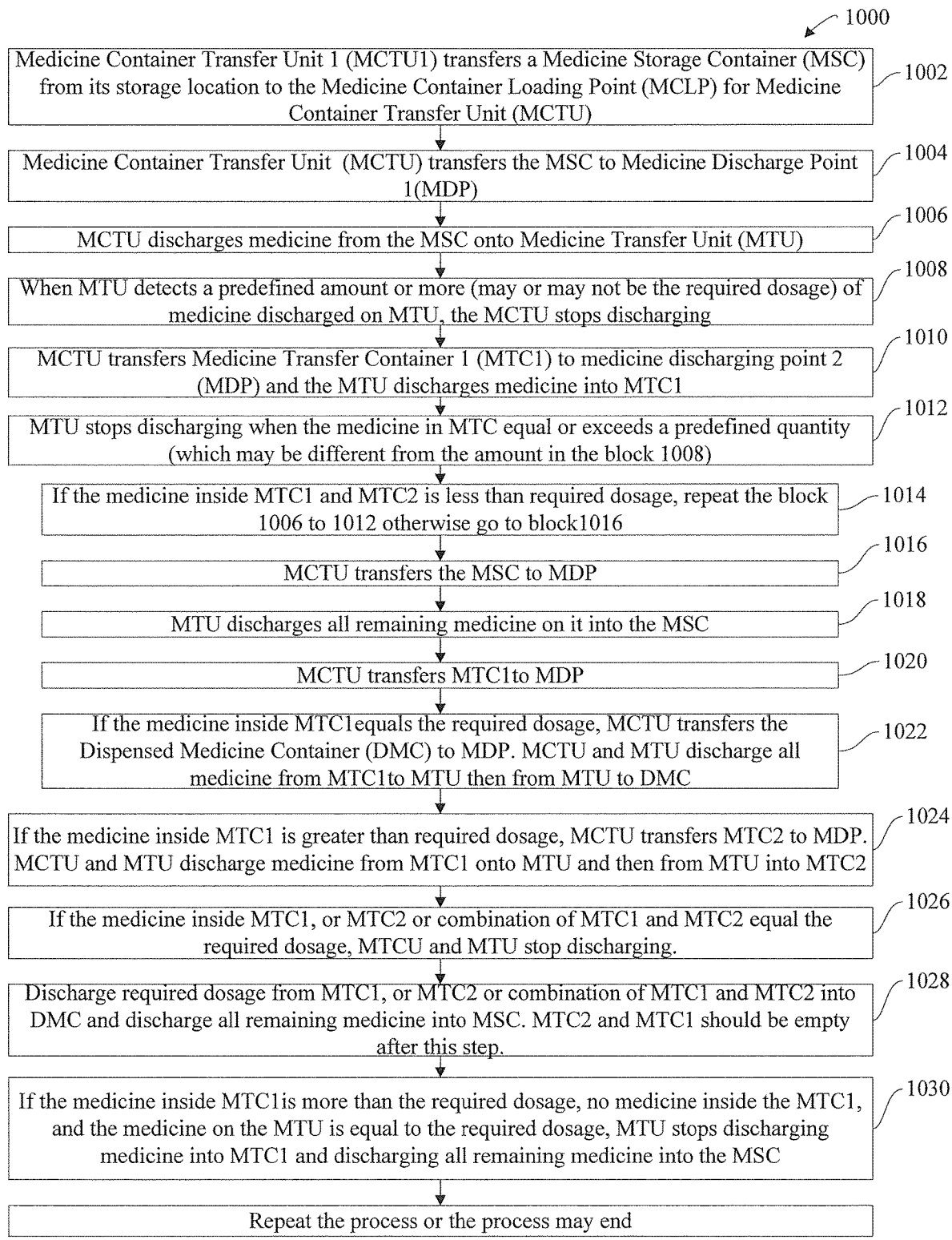
FIG. 10 is a flow diagram illustrating an exemplary process for dispensing a dose of medicine via the exemplary sub-assembly of FIG. 3.

Referring now to FIG. 10, a flow diagram of another exemplary process 1000 for operating the dispensing unit 102 is illustrated, which may incorporate the sub-assembly 300. Process 1000 may include operations that may be part of program 110, stored on memory 108, and/or executed by processor 106. Process 1000 may take many different forms and include multiple and/or alternate steps. While an exemplary process is shown, the exemplary steps illustrated are not intended to be limiting. Indeed, additional or alternative steps and/or implementations may be used.

Process 1000 may begin at step 1002 at which the processor 106 may run calibration and verification logic with calibration and verification device 382 to calibrate or verify weight detecting devices.

At block 1004, the medicine container transfer unit 330 (MCTU) may transfer the medicine transfer container 375 (MTC1) to second discharge point 380 (MDP2) and a medicine storage container 320 (MSC) from its storage location to first discharge point 350 (MDP1).

At block 1006, the medicine container transfer unit 330 (MCTU) may discharge medicine from the medicine storage container 320 (MSC) onto the medicine transfer unit 355 (MTU). This may be achieved by rotating the medicine storage container 320 (MSC), which may be steady or intermittent. It should be appreciated that other ways to discharge the medicine from the medicine storage container 320 (MSC) onto the medicine transfer unit 355 (MTU) are contemplated.

At block 1008, the medicine container transfer unit 330 (MCTU) may stop discharging when it receives a signal from the medicine transfer unit 355 (MTU) or other medicine detecting devices that detects at least a predefined amount of medicine discharged on the medicine transfer unit 355 (MTU), which may or may not be the required dosage. For example, the medicine transfer unit 355 (MTU) may include one or more sensors that detect weight, area, volume, or any other characteristic by which an amount of medicine on the medicine transfer unit 355 (MTU) may be determined. The medicine transfer unit 355 (MTU) may then communicate, e.g., send a signal, directly to the medicine container transfer unit 330 (MCTU) to stop discharging, or indirectly by sending a signal to the processor 106 that the predefined amount of medicine has been detected, the processor 106 in turn commanding the medicine container transfer unit 330 (MCTU) to stop discharging.

At block 1010, the medicine transfer unit 355 (MTU) may then begin discharging the medicine on it into the medicine transfer container 375 (MTC1) at a second discharge point 380 (MDP2), which may be, but is not limited to, at an end of the medicine transfer unit 355 (MTU).

At block 1012, the medicine transfer unit 355 (MTU) may stop discharging the medicine when the medicine in the medicine transfer container 375 (MTC1) equal or exceeds a predefined quantity (which may be different from the amount in the block 1008).

At block 1014, the processor 106 may determine if the medicine inside the first medicine transfer container 375 (MTC1) is less than the required dosage, In one exemplary approach, this may be determined by measuring the weight of the medicine in the first medicine transfer container 375 (MTC1) by weight checking station 360 and/or by the scale 395 on which the first medicine transfer container 375 (MTC1) may be disposed. The weight checking device 395 and/or weight checking station 360 may then transmit data representing the measured weight to the processor 106, which may then compare the measured weight with a weight corresponding to the medicine in the required dosage, which may be stored locally on the memory 108 and/or remotely at any one of the databases 510-516.

If the medicine inside the first medicine transfer container is not less than the required dosage, then process 1000 may proceed to block 1016. If it is less, then process 1000 may repeat blocks 1006 to 1012 until the amount of medicine inside the first medicine transfer container 375 (MTC1) is not less than the required dosage. Then process 1000 may proceed to block 1016.

At block 1016, the medicine container transfer unit 330 (MCTU) may transfer the medicine storage container 320 (MSC) to the second medicine discharge point 380.

At block 1018, the medicine transfer unit 355 (MTU) may discharge the remaining medicine on it back into the medicine storage container 320 (MSC).

At block 1020, the medicine container transfer unit 330 (MCTU) may move the first medicine transfer container 375 (MTC1) to the first medicine discharge point 350 (MDP1). If the medicine in the first medicine transfer container 375 (MTC1) is equal to the required dosage, process 1000 may proceed to block 1022. If the medicine in the first medicine transfer container 375 (MTC1) is greater than the required dosage, process 1000 may proceed to block 1024.

At block 1022, the medicine container transfer unit 330 (MCTU) may transfer the dispensed medicine container 365 (DMC) to the second medicine discharge point 380 (MDP2). The medicine container transfer unit 330 (MCTU) may then transfer all the medicine in the first medicine transfer container 375 (MTC1) onto the medicine transfer unit 355 (MTU), which, in turn, may then transfer the medicine into the dispensed medicine container 365 (DMC). Process 1000 may end after this step.

At block 1024, the medicine container transfer unit 330 (MCTU) may transfer the second medicine transfer container 370 (MTC2), to the second medicine discharge point 380 (MDP2). The medicine container transfer unit 330 (MCTU) may then discharge medicine from the first medicine transfer container 375 (MTC1) onto the medicine transfer unit 355 (MTU), which, in turn, may begin transferring medicine into the second medicine transfer container 370 (MTC2). The processor 106 may then determine if the medicine on the medicine transfer unit 355 (MTU) is equal to the required dosage. If it is equal, process 1000 may proceed to block 1026. The processor 106 may also determine if the medicine inside the first medicine transfer container 375 (MTC1), the second medicine transfer container 370 (MTC2), or the combination of the medicine transfer containers 370, 375 is equal to or greater than the required dosage. If it is equal, process 1000 may proceed to block 1028. If it is greater, process 1000 may proceed to block 1030.

At block 1026, if the medicine on the medicine transfer unit 355 (MTU) is equal to the required dosage, the medicine transfer unit 355 (MTU) may stop discharging medicine into the second medicine transfer container 370 (MTC2) and may discharge all medicine on the medicine transfer unit 355 (MTU) into the dispensed medicine container 365 (DMC). The remaining medicine inside the medicine transfer containers 370 (MTC2) and 375 (MTC1) may be discharged back into the medicine storage container 320 (MSC). Process 1000 may end after this step.

At block 1028, if medicine in the first medicine transfer container 375 (MTC1), the second medicine transfer container 370 (MTC2), or combination of both that equals the required dosage, the required dosage may be discharged into the dispensed medicine container 365 (DMC). The remaining amount of medicine, which may be in the first medicine transfer container 375 (MTC1), the second medicine transfer 370 (MTC2) and/or on the medicine transfer unit 355 (MTU), may be discharged back into the medicine storage container 320 (MSC). Both medicine transfer containers 370, 375 should be empty after this step. Process 1000 may end after this step.

At block 1030, if the medicine inside MTC 370 (MTC2) is more than the required dosage, the medicine container transfer unit 330 (MCTU) transfers the medicine transfer container 370 (MTC2) to the first medicine discharging point 350 (MDP1) and the medicine transfer container 375 (MTC1) to the second medicine discharging point 380 (MDP2) and discharging all remaining medicine on the medicine transfer unit 355 (MTU) into the medicine storage container 320 (MSC). Repeat blocks 1006 to 1030 with the medicine transfer containers 375 370 until required dosage is dispensed into the dispensed medicine container 365 and all extra medicine is returned to the medicine storage container 320.

Process 1000 may be repeated for the next medicine when required.

In general, process 1000 may be a closed feedback loop process with stable and fast convergent iterations. In addition, the processor 106 may communicate with, i.e., send commands to, receive data from, and the like, to various components of the dispensing unit 102 and/or system 500 to perform process 1000, and to decide the best way to distribute the medicine among medicine storage container 320, the medicine transfer containers 370, 375, and the dispensed medicine container 365 based on process 1000.

Figure 11A:
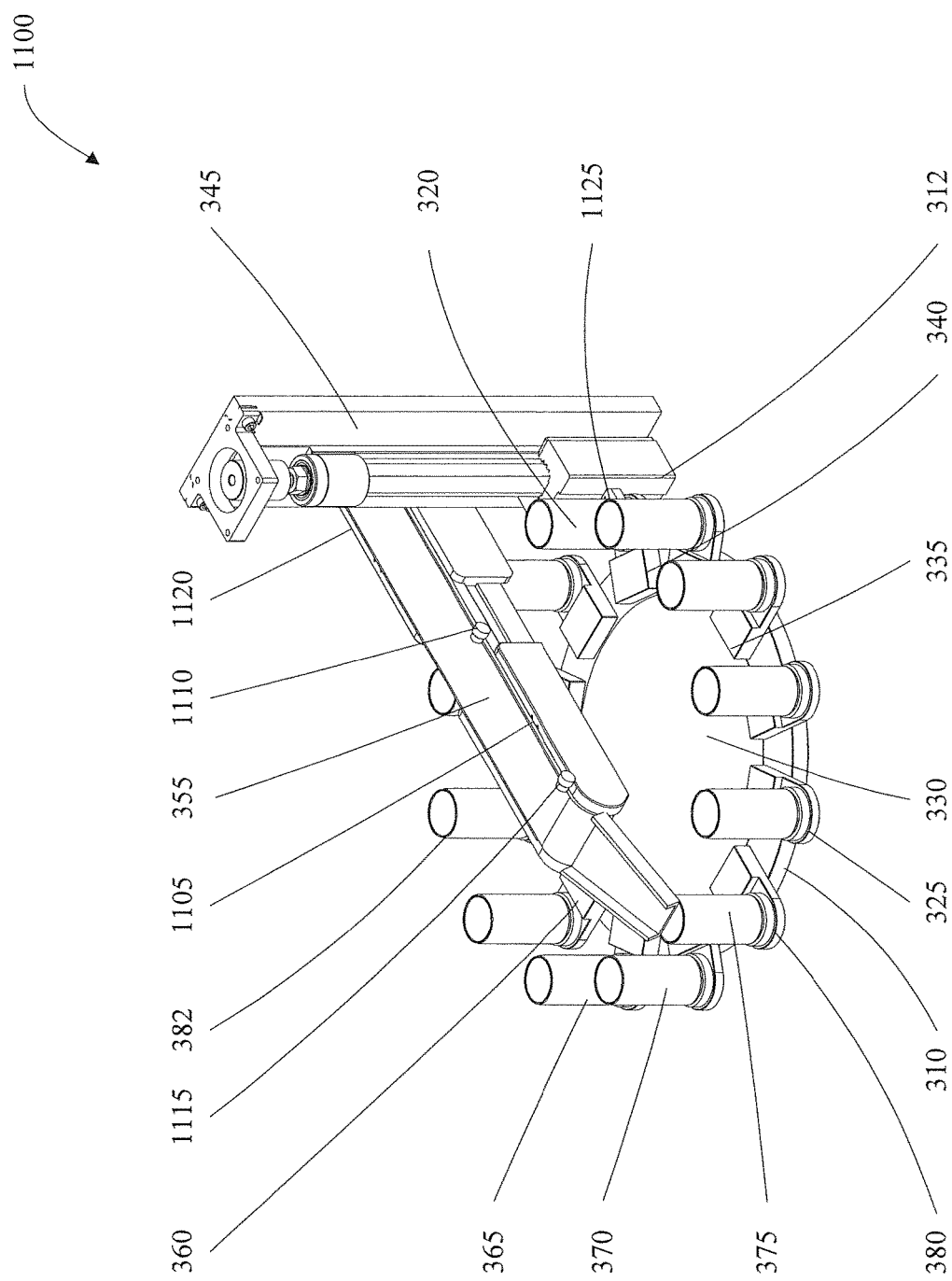
FIG. 11A is a perspective view of a sub-assembly according to another exemplary approach.
Figure 11B:
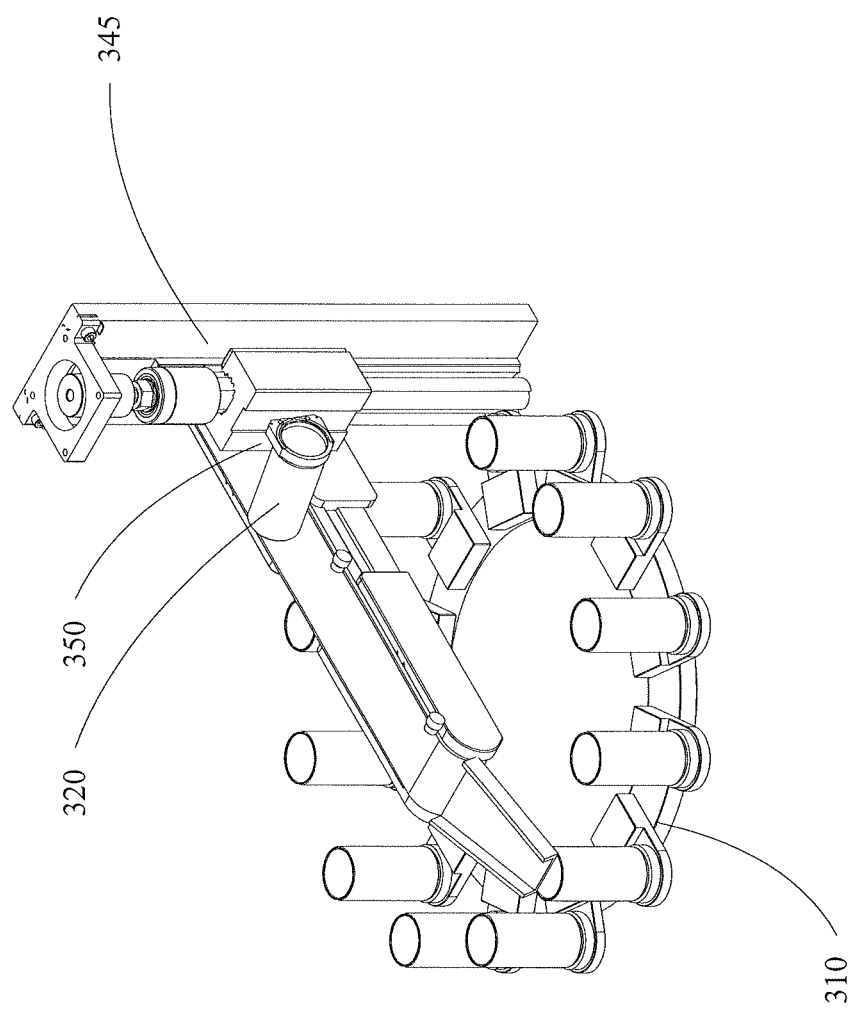
FIG. 11B illustrates the exemplary system of FIG. 11A during operation.
Figure 11C:
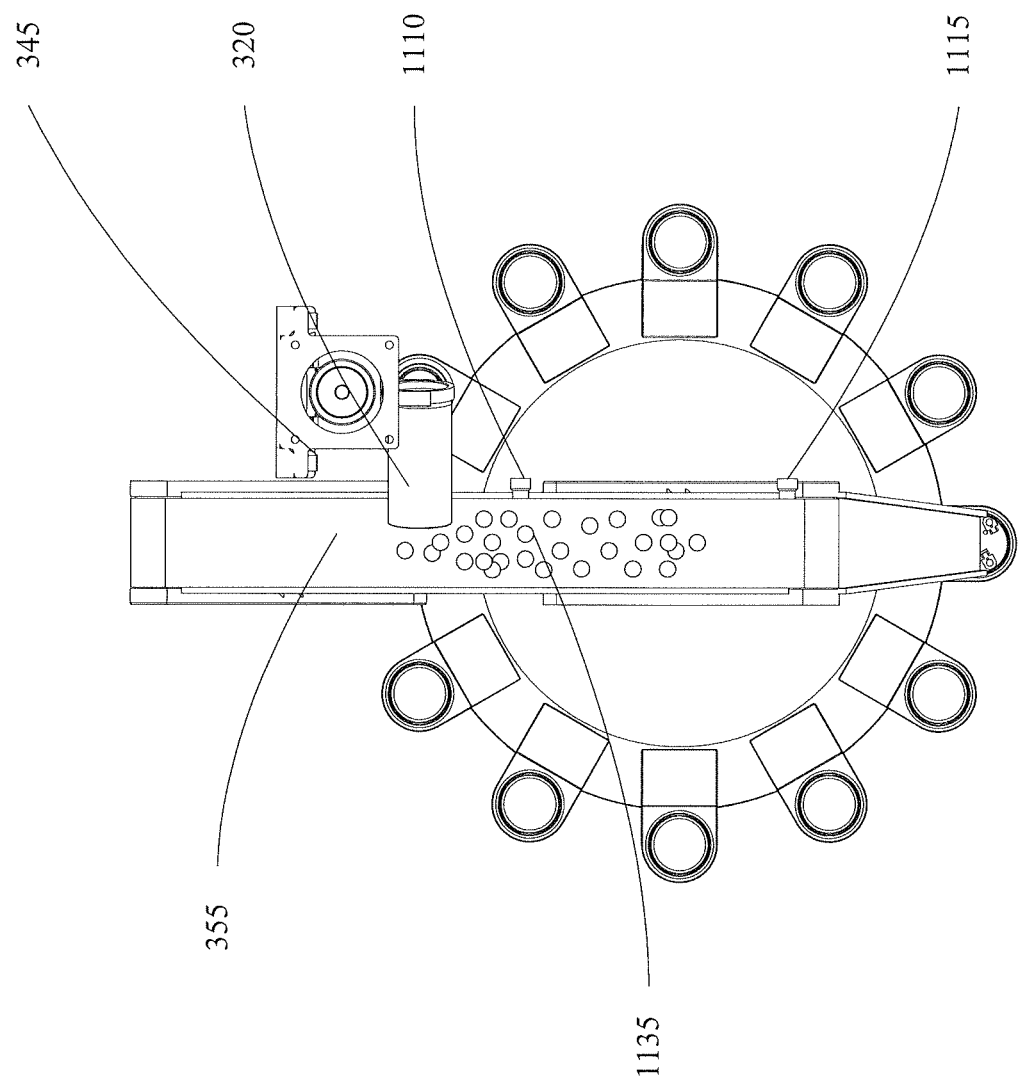
FIG. 11C illustrates a top view of the exemplary system of FIG. 11B.

FIG. 11A illustrates an exemplary sub-assembly 1100 of the disclosed system. FIG. 11B illustrates the exemplary system of FIG. 11A during operation. FIG. 11C illustrates a top view of the exemplary system of FIGS. 11A and 11B. FIG. 11A illustrates the disclosed dispenser having a conveyor 1105, a robot 1120, and carousel 310. In this example medicine container transfer unit 330 includes carousel 310, medicine container transfer unit 345 includes robot 1120 having an end of arm tool 1125, medicine transfer unit 355 having a conveyor 1105 and sensors 1110 and 1115. FIG. 11B is a view of sub-assembly as shown in FIG. 11A, showing medicine storage container 320 transferred to first medicine discharge point 350 by medicine container transfer unit 345 to discharge medicine from medicine storage container 320 to conveyor 1105. Sensors 1110 and 1115 monitor medicine positioned on medicine transfer unit 355 and more specifically on conveyor 1105.

FIG. 11A illustrates an exemplary sub-assembly 1100 illustrating the disclosed system or dispenser. Sub-assembly 1100 is a view of inside elements of dispenser 102 and includes carousel 310. Sub-assembly 1100 includes loading station or medicine container loading station 325, first medicine container transfer unit 330, and medicine container storage nest 335. Medicine container loading point 340 is proximate second medicine container transfer unit 345. First medicine discharge point 350 includes, in the illustrated example, medicine transfer unit 355 that may include conveyer 1105 for transporting or otherwise conveying medicine from medicine container transfer unit 345 to second medicine discharge point 380, and may include sensors 1110 and 1115. Sub-assembly 1100 includes weight checking station 360, dispensed medicine container 365, a calibration and verification device 382 to automatically calibrate weight detecting devices, and medicine transfer containers 370 and 375. Medicine storage container 320 is positioned on carousel 310.

Referring to FIGS. 11A-C, FIG. 11A is an illustration of medicine storage container 320 as positioned proximate medicine container transfer unit 345, and FIG. 11B the exemplary system of FIG. 11A during operation. Medicine storage container 320 may include original medicine container 390, medicine container identification unit 385, weight detecting device 395, and medicine container storage nest 335. Weight detecting device 395 and medicine container storage nest 335 may be integrated together. Weight detecting device 395 and medicine container storage nest 335 may also be part of carousel 310. Weight detecting device 395 may be a scale, a load cell, or other device for measuring weight, according to the disclosure. Weight detecting device 395 and medicine container storage nest 335 are positioned about carousel 310 at each of the illustrated locations. Medicine container identification unit 385 may include identification information particular to a given medicine, and may also identify an amount of medicine that may constitute a single patient dose particular to a given user of dispenser 102.

Referring still to FIG. 11A, medicine storage container 320 may be loaded into dispenser 102 from medicine container loading station 325, and medicine storage container 320 is transferred to its storage position by medicine container transfer unit 330. Medicine storage container 320 may include medicine in the form of a pill or a capsule, as examples, and a dose of medicine for a user may include one or more of the pills or capsules. Medicine container transfer unit 330 is illustrated as having carousel 310, but may instead include a conveyor, a robot, or any device that can move medicine storage container 320 from one position to another, and discharge medicine from medicine storage container 320.

Medicine transfer unit 355 moves medicine from one position to another, accepts medicine from medicine storage container 320, and medicine transfer unit 355 also discharges medicine into medicine storage container 320 or any container when positioned at medicine discharge point 380. Medicine transfer unit 355 may have a linear moving surface such as a walking beam, a conveyor, or a rotating surface such as a rotating disc or other shape.

In operation, as shown in FIGS. 11A and 11B, dispenser 102 moves, via carousel 310, medicine storage container 320 to loading point 312, and loading point 312 is proximate medicine container transfer unit 345. Medicine container transfer unit 345 engages with medicine storage container 320 by attaching thereto, and moving medicine storage container 320 to first medicine discharge point 350. Medicine storage container 320 is, in one example, a medicine storage container which may have an amount of medicine that is in excess of a dose, or an amount of medicine that is desired to be distributed into dispensed medicine container 365. Medicine container transfer unit 345 turns medicine storage container 320 such that at least a predetermined amount of medicine spills or otherwise pours from medicine storage container 320 onto medicine transfer unit 355, as determined by medicine detecting device. Carousel 310 rotates to move medicine storage container 375 to second medicine discharge point 380. When medicine transfer container 375 is positioned at medicine discharge point 380, and when medicine has been discharged onto medicine transfer unit 355, medicine transfer unit 355 thereby conveys the discharged medicine from medicine transfer unit 355 into medicine transfer container 375 until at least a second predetermined amount of medicine is contained in medicine transfer container 375, as determined by weight detecting device, which weigh and transmit weight information to for instance a controller of dispenser 102.

Medicine transfer unit 355 includes conveyor 1105, and sensors 1110 and 1115, which monitor medicine positioned on medicine transfer unit 355 and on conveyor 1105. Sensors 1110, 1115 may be optical sensors that are coupled, electrically or optically as examples, to processor 106. As such, processor 106 monitors medicine positioned on medicine transfer unit 355 via sensors 1110, 1115.

FIG. 11C illustrates a top view of the exemplary system of FIGS. 11A and 11B, and shows medicine storage container 320 turned such that at least a predetermined amount of medicine spills or otherwise pours from medicine storage container 320 onto medicine transfer unit 355. Sensors 1110 and 1115 detect the presence of pills or capsules 1135 as they pass thereby via medicine transfer unit 355 to second medicine discharge point 380.

Medicine is transferred from medicine transfer unit 355 into medicine transfer container 375, and a weight of the medicine is determined via weight detecting device. If the measured weight is less than a given or desired dose, and if medicine is still on medicine transfer unit 355 (i.e., has not been fully discharged), then medicine transfer unit 355 further conveys more medicine into medicine transfer container 375. On the other hand, if no medicine is on medicine transfer unit 355, then additional medicine is discharged to medicine transfer unit 355 from medicine storage container 320. The process of discharging from medicine storage container 320 to medicine transfer unit 355, and from medicine transfer unit 355 to medicine transfer container 375 continues until at least a dose of medicine is contained in medicine transfer container 375. That is, medicine transfer container 375 may include an exact or desired dose, or may include an amount of medicine that is in excess of an exact dose.

If an exact dose is present in medicine transfer container 375, then dispenser 102 operates to convey medicine transfer container 375 to first medicine discharge point 350 via medicine container transfer unit 345, any remaining medicine on medicine transfer unit 355 is discharged back into medicine storage container 320 at second medicine discharge point 380, and the medicine in medicine transfer container 375 is discharged into dispensed medicine container 365 that is positioned at second medicine discharge point 380.

On the other hand, in one example medicine transfer container 375 may include an amount of medicine that is in excess of an exact dose. In such an example, medicine transfer container 375 is thereby conveyed to first medicine discharge point 350 and operations described above are repeated with medicine transfer container 375 and/or medicine transfer container 370. That is, medicine container transfer unit 345 discharges medicine from medicine transfer container 375 onto medicine transfer unit 355, and medicine transfer container 375 (or 370) is conveyed via carousel 310 to second medicine discharge point 380. Medicine discharged from medicine transfer container 375 to medicine transfer unit 355 is thereby conveyed to medicine transfer container 375 (or 370) until at least the exact dose is present in medicine transfer container 375 (or 370). And, again, if medicine transfer container 375 (or 370) includes medicine equal to the dose, then the medicine in medicine transfer container 375 (or 370) is discharged into dispensed medicine container 365, and any excess medicine on medicine transfer unit 355 is returned to medicine storage container 320.

The aforementioned steps continue until a dose of medicine is contained within dispensed medicine container 365, and any additional medicine is returned to medicine storage container 320. In such fashion, dispenser 102 includes a feedback mechanism, ensuring a proper dose, and only a proper dose, is contained in dispensed medicine container 365. That is, feedback is provided in the form of a weight of pills or capsules, corresponding to a dose, measured via weight detecting device 395. Dispenser 102 is caused to operate using such feedback to ensure that a correct dose is provided in dispensed medicine container 365.

Figure 12:
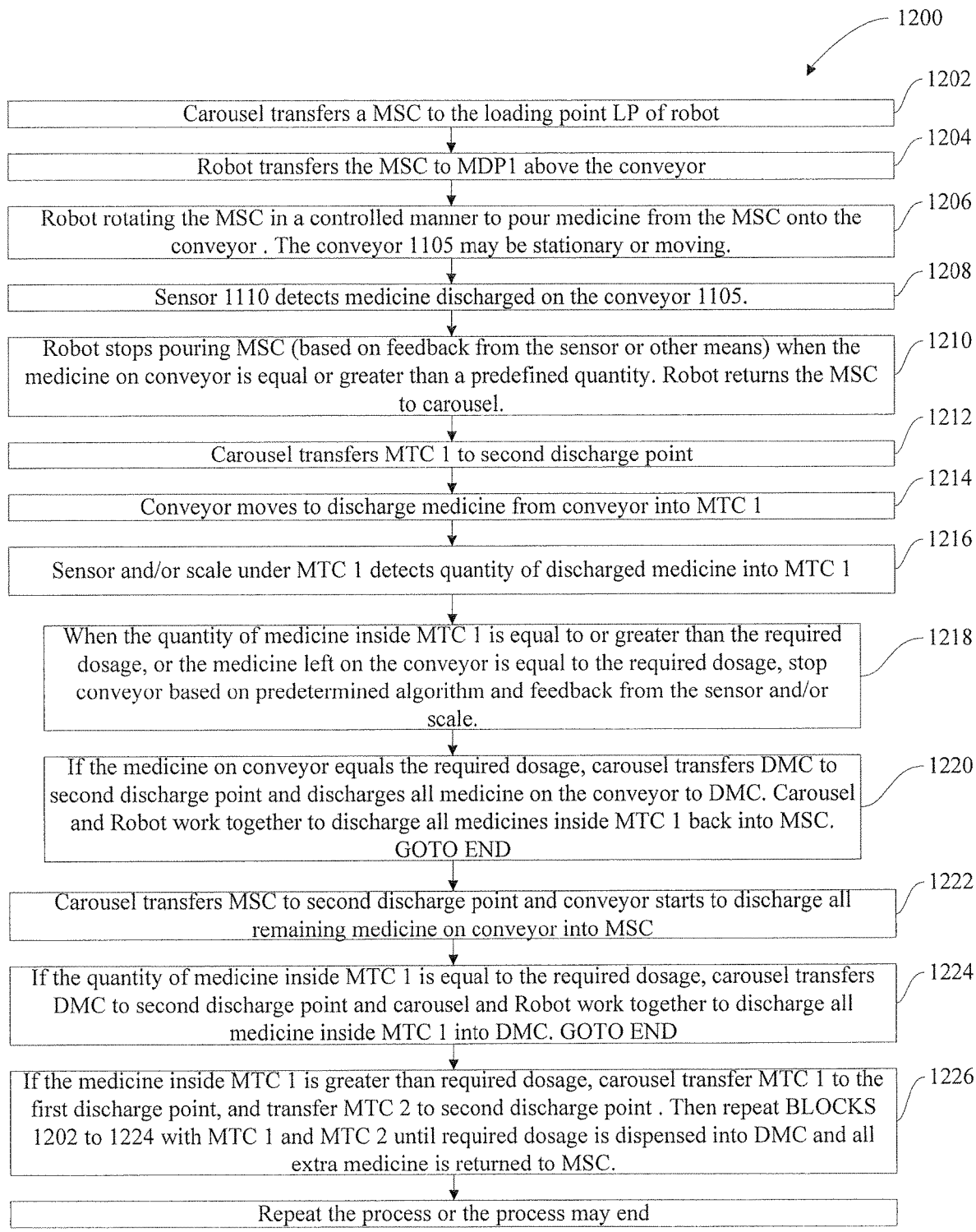
FIG. 12 is a flow diagram illustrating an exemplary process for dispensing a dose of medicine via the exemplary sub-assembly of FIGS. 11A-11C.

Referring now to FIG. 12, a flow diagram of another exemplary process 1200 for operating the dispensing unit 102, which may incorporate the sub-assembly 1100, is illustrated. Process 1200 may include operations that may be part of program 110, stored on memory 108, and/or executed by processor 106. Process 1200 may take many different forms and include multiple and/or alternate steps. While an exemplary process is shown, the exemplary steps illustrated are not intended to be limiting. Indeed, additional or alternative steps and/or implementations may be used. In addition, for purposes of process 1200, the first medicine container transfer unit 330 is referred to as the carousel, and the second medicine container transfer unit 345 is referred to as the robot. However, it should be appreciated that any medicine container transfer unit 330, 345 for performing the respective step(s) is contemplated, and that the use of the terms carousel and robot are not intended to be limiting.

Process 1200 may begin at block 1202 at which the carousel 310 may transfer a medicine storage container 320 to the loading point 340 of robot 345.

At block 1204, robot 345 may transfer the medicine storage container 320 to a first medicine discharge point 350 above the conveyor 1105.

At block 1206, robot 345 may rotate the medicine storage container 320 in a controlled manner to pour medicine from the medicine storage container 320 onto the conveyor 1105, which may be stationary or moving.

At block 1208, at least one sensor 1110 may detect medicine discharged on the conveyor 1105.

At block 1210, robot 345 may stop pouring medicine storage container 320 when medicine on the conveyor 1105 is equal to or greater than a predefined quantity. This may be determined based on feedback from sensor 1110 or other means. Robot 345 may then return the medicine storage container 320 to carousel 310.

At block 1212, the carousel 310 may transfer a medicine transfer container 375, to the second medicine discharge point 380.

At block 1214, the conveyor 1105 may move to discharge medicine from the conveyor 1105 into the medicine transfer container 375.

At block 1216, a sensor 1115 and/or scale 395 under the medicine transfer container 375 may detect a quantity of medicine discharged into the medicine transfer container 375.

At block 1218, the conveyor 1105 is stopped based on feedback from the sensor 1115 and/or scale 395 that the quantity of medicine inside the medicine transfer container 375 is equal to or greater than the required dosage, or the medicine left on the conveyor 1105 is equal to the required dosage.

At block 1220, the processor 106 may determine if the medicine on the conveyor 1105 equals the required dosage. If so, carousel 310 may transfer the dispensed medicine container 365 to the second medicine discharge point 380, and the conveyor 1105 may discharge all of the medicine on it into the dispensed medicine container 365. Carousel 310, robot 345, and conveyor 355 may then work together to discharge all medicines inside the medicine transfer container 375 back into the medicine storage container 320. Process 1200 may then end.

At block 1222, carousel 310 may transfer medicine storage container 320 to the second medicine discharge point 380, and conveyor 1105 may begin to discharge all remaining medicine on conveyor 1105 into the medicine storage container 320.

At block 1224, the processor 106 may determine if the medicine inside the medicine transfer container 375 is equal to the required dosage. If so, carousel 310 may transfer the dispensed medicine container 365 to the second medicine discharge point 380. Carousel 310, robot 345, and conveyor 355 may then work together to discharge all medicines inside the medicine transfer container 375 into the dispensed medicine container 365. Process 1200 may then end.

At block 1226, the processor 106 may determine if the medicine inside the medicine transfer container 375 is greater than the required dosage. If so, carousel 310 may transfer the medicine transfer container 375 to the first medicine discharge point 350 and discharge medicine inside the medicine transfer container 375 onto the conveyor 1105, and then transfer the medicine transfer container 375 (or 370) to the second medicine discharge point 380. Blocks 1202 through 1224 may then be repeated with the medicine containers 375 (and/or 370), 320 and 365 until the required dosage is dispensed into the dispensed medicine container 365, and all extra medicine, e.g., in the medicine transfer containers 375 (and/or 370) and/or on the conveyor 1105, is returned to the medicine storage container 320.

Process 1200 may be repeated for the next medicine when required.

In embodiments, scale(s) 395, for example, in each weighing station or storage nests associated with each container, may check quantity of medicine inside each container involved in process 1200, e.g., the medicine storage container 320, the medicine transfer containers 370, 375, and the dispensed medicine container 365.

In general, process 1200 may be a closed feedback loop process with stable and fast convergent iterations. In addition, the processor 106 may communicate with, i.e., send commands to, receive data from, and the like, to various components of the dispensing unit 102 and/or system 500 to perform process 1200, and may decide the best way to distribute the medicine among medicine storage container 320, the medicine transfer containers 375 (or 370), and the dispensed medicine container 365 based on process 1200.

Figure 13A:
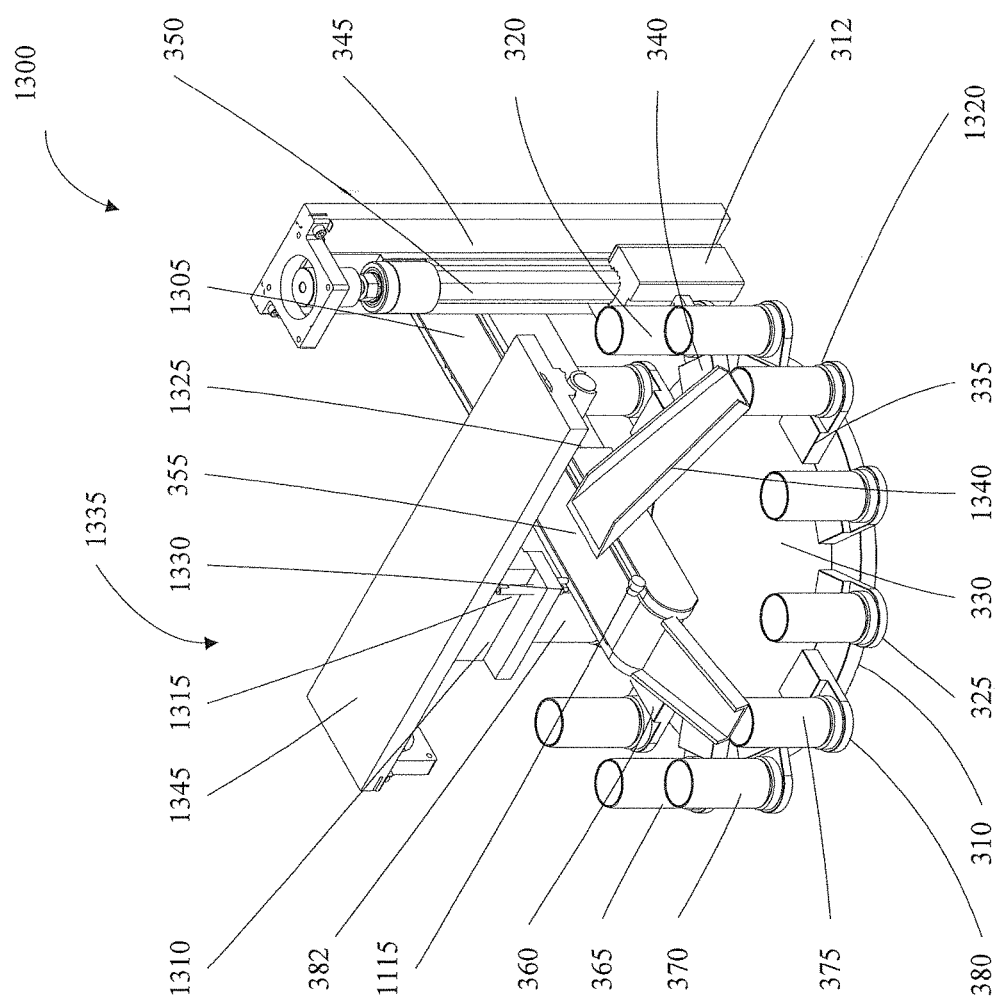
FIG. 13A is a perspective view of a sub-assembly according to another exemplary approach.

FIG. 13A illustrates an exemplary sub-assembly 1300 of the disclosed system. Sub-assembly 1300 includes medicine container transfer unit 330 having carousel 310, medicine container transfer unit 345 includes a robot with end of arm tool. Medicine transfer unit 355 includes a robot or conveyor 1305, sensors 1110 (not visible) and 1115, robot 1345 having an end of arm tool (EOAT) 1310, a sensor 1330, and a vacuum head 1315. Medicine container transfer unit 345 and robot 1345 may be two different robots, or two different parts of the same one robot.

Figure 13B:
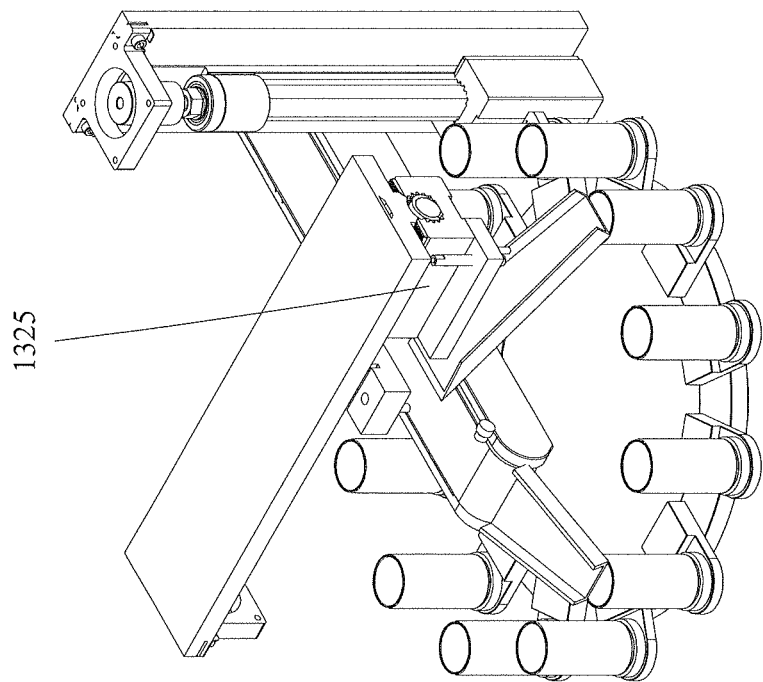
FIG. 13B illustrates the exemplary system of FIG. 13A during operation.

FIG. 13B is a view of the example of FIG. 13A, showing end of arm tool 1310 at medicine discharge position 1325 to discharge medicine into medicine container at discharge position 1320. The end of arm tool 1310 may also discharge medicine into medicine container at discharge position 380 (not shown). The end of arm tool 1310 may also pick up medicine from medicine containers at discharge position 1320 or 380 and discharge onto medicine transfer unit 355.

Sub-assembly 1300 is a view of inside elements of dispenser 102 and includes carousel 310. Sub-assembly 1300 includes loading station or medicine container loading station 325, first medicine container transfer unit 330, and medicine container storage nest 335. Medicine container loading point 340 is proximate second medicine container transfer unit 345. First medicine discharge point 350 includes, in the illustrated example, medicine transfer unit 355 that may include robot 1345 and conveyer 1305 for transporting or otherwise conveying medicine from first medicine discharge point 350 to second medicine discharge point 380, and may include sensors 1110 (not visible) and 1115. Sub-assembly 1300 includes weight checking station 360, a calibration and verification device 382 to automatically calibrate weight detecting devices, dispensed medicine container 365, and medicine transfer container 370 and 375. Medicine storage container 320 is positioned on carousel 310.

FIG. 13A is an illustration of exemplary sub-system 1300, and FIG. 13B of the exemplary system of FIG. 13A shows end of arm tool 1310 at medicine discharge position 1325. Medicine storage container 320 may include original medicine container 390, medicine container identification unit 385, weight detecting device 395, and medicine container storage nest 335. Weight detecting device 395 and medicine container storage nest 335 may be integrated together. Weight detecting device 395 and medicine container storage nest 335 may also be part of carousel 310. Weight detecting device 395 may be a scale, a load cell, or other device for measuring weight, according to the disclosure. Weight detecting device 395 and medicine container storage nest 335 are positioned about carousel 310 at each of the illustrated locations. Medicine container identification unit 385 may include identification information particular to a given medicine, and may also identify an amount of medicine that may constitute a single patient dose particular to a given user of dispenser 102.

Referring still to FIG. 13A, medicine storage container 320 may be loaded into dispenser 102 from medicine container loading station 325, and medicine storage container 320 is transferred to medicine container loading point 340 by medicine container transfer unit 330. Medicine storage container 320 may include medicine in the form of a pill or a capsule, as examples, and a dose of medicine for a user may include one or more of the pills or capsules. Medicine container transfer unit 330 is illustrated as having carousel 310, but may instead include a conveyor, a robot, or any device that can move medicine storage container 320 from one position to another, and discharge medicine from medicine storage container 320.

Medicine transfer unit 355 moves medicine from one position to another, accepts medicine from medicine storage container 320, and medicine transfer unit 355 also discharges medicine into medicine storage container 320 or any container when positioned at medicine discharge point 380. Medicine transfer unit 355 may have a linear moving surface such as a walking beam, a conveyor, or a rotating surface such as a rotating disc or other shape, and includes in the illustrated example conveyer 1105 and robot 1345.

In operation, as shown in FIGS. 13A and 13B, dispenser 102 moves, via carousel 310, medicine storage container 320 to loading point 312, and loading point 312 is proximate medicine container transfer unit 345. Medicine container transfer unit 345 engages with medicine storage container 320 by attaching thereto, and moving medicine storage container 320 to first medicine discharge point 350. Medicine storage container 320 is, in one example, a medicine storage container which may have an amount of medicine that is in excess of a dose, or an amount of medicine that is desired to be distributed into dispensed medicine container 365. Medicine container transfer unit 345 turns medicine storage container 320 such that at least a predetermined amount of medicine spills or otherwise pours from medicine storage container 320 onto medicine transfer unit 355, as determined by sensors or medicine detecting device of the medicine transfer unit 355. Carousel 310 rotates to move medicine transfer container 375 to second medicine discharge point 380. When medicine transfer container 375 is positioned at medicine discharge point 380, and when medicine has been discharged onto medicine transfer unit 355, medicine transfer unit 355 thereby conveys the discharged medicine from medicine transfer unit 355 into medicine transfer container 375 until at least a second predetermined amount of medicine is contained in medicine transfer container 375, as determined by weight detecting device 395 and medicine container storage nest 335, which weigh and transmit weight information to for instance a controller of dispenser 102.

Medicine transfer unit 355 includes robot 1345 and conveyor 1305, and sensors 1110 and 1115, which monitor medicine positioned on medicine transfer unit 355 and on conveyor 1305. Sensors 1110, 1115 may be optical sensors that are coupled, electrically or optically as examples, to processor 106. As such, processor 106 monitors medicine positioned on medicine transfer unit 355 via sensors 1110, 1115. Sensors 1110 and 1115 detect the presence of pills or capsules as they pass thereby via medicine transfer unit 355 to second medicine discharge point 380. In addition, robot 1345 includes end of arm tool 1310 having vacuum head 1315 that may attach via a vacuum, controlled by processor 106, to individual pills or capsules passing along medicine transfer unit 355. Accordingly, in this example, pills or capsules may be not only conveyed by conveyor 1305 to medicine transfer container 370 or medicine transfer container 375 when positioned at medicine discharge point 380, but also conveyed by robot 1345 to medicine transfer container 370 or 375 when positioned at medicine discharge point 380. Pills or capsules may also be conveyed by robot 1345 to medicine transfer container 370 or 375 positioned at position 1320. Pills or capsules may also be conveyed by robot 1345 from medicine transfer containers 370 or 375 at discharge point 380 or 1320 back to the medicine transfer unit 355. Both methods may be used concurrently or separately. Thus, overall efficiency or movement of pills or capsules may be improved by having an ability to move pills or capsules to and/or from two locations simultaneously.

Medicine is transferred from medicine transfer unit 355 into medicine transfer container 375, and a weight of the medicine is determined via weight detecting device. If the measured weight is less than a predetermined amount, and if medicine is still on medicine transfer unit 355 (i.e., has not been fully discharged), then medicine transfer unit 355 further conveys more medicine into medicine transfer container 375. On the other hand, if no medicine is on medicine transfer unit 355, then additional medicine is discharged to medicine transfer unit 355 from medicine storage container 320. The process of discharging from medicine storage container 320 to medicine transfer unit 355, and from medicine transfer unit 355 to medicine transfer container 375 continues until at least a predetermined amount of medicine is contained in medicine transfer container 375. That is, medicine transfer container 375 may include an exact or desired dose, or may include an amount of medicine that is in excess of an exact dose.

If an exact dose is present in medicine transfer container 375, then dispenser 102 operates to convey medicine transfer container 375 to first medicine discharge point 350 via medicine container transfer unit 345, any remaining medicine on medicine transfer unit 355 is discharged back into medicine storage container 320 at second medicine discharge point 380, and the medicine in medicine transfer container 375 is discharged into dispensed medicine container 365 that is positioned at second medicine discharge point 380.

On the other hand, in one example medicine transfer container 375 may include an amount of medicine that is in excess of an exact dose. In such an example, medicine transfer container 375 is thereby conveyed to first medicine discharge point 350 and operations described above are repeated. That is, medicine container transfer unit 345 discharges medicine from medicine transfer container 375 onto medicine transfer unit 355, and then medicine transfer container 375 (or 370) is conveyed via carousel 310 to second medicine discharge point 380. Medicine discharged from medicine transfer container 375 to medicine transfer unit 355 is thereby conveyed to medicine transfer container 375 (or 370) until at least the exact dose is present in medicine transfer container 375 (or 370). And, again, if medicine transfer container 375 (or 370) includes medicine equal to the dose, then the medicine in medicine transfer container 375 (or 370) is discharged into dispensed medicine container 365, and any excess medicine on medicine transfer unit 355 is returned to medicine storage container 320.

The aforementioned steps continue until a dose of medicine is contained within dispensed medicine container 365, and any additional medicine is returned to medicine storage container 320. In such fashion, dispenser 102 includes a feedback mechanism, ensuring a proper dose, and only a proper dose, is contained in dispensed medicine container 365. That is, feedback is provided in the form of a weight of pills or capsules, corresponding to a dose, measured via weight detecting device 395. Dispenser 102 is caused to operate using such feedback to ensure that a correct dose is provided in dispensed medicine container 365. However, in the illustrated example, medicine, in this example, may be conveyed to and from medicine transfer container 370 or medicine transfer container 375 positioned at discharge position 1320 and 380, allowing simultaneous iterations using two conveying methods on two containers in both directions, which may allow convergence to a final dose, and movement of medicine to and from medicine transfer unit 355 via a second path (i.e., via vacuum head 1315, for discharge position 380 and for a container positioned at discharge position 1320).

Figure 14:
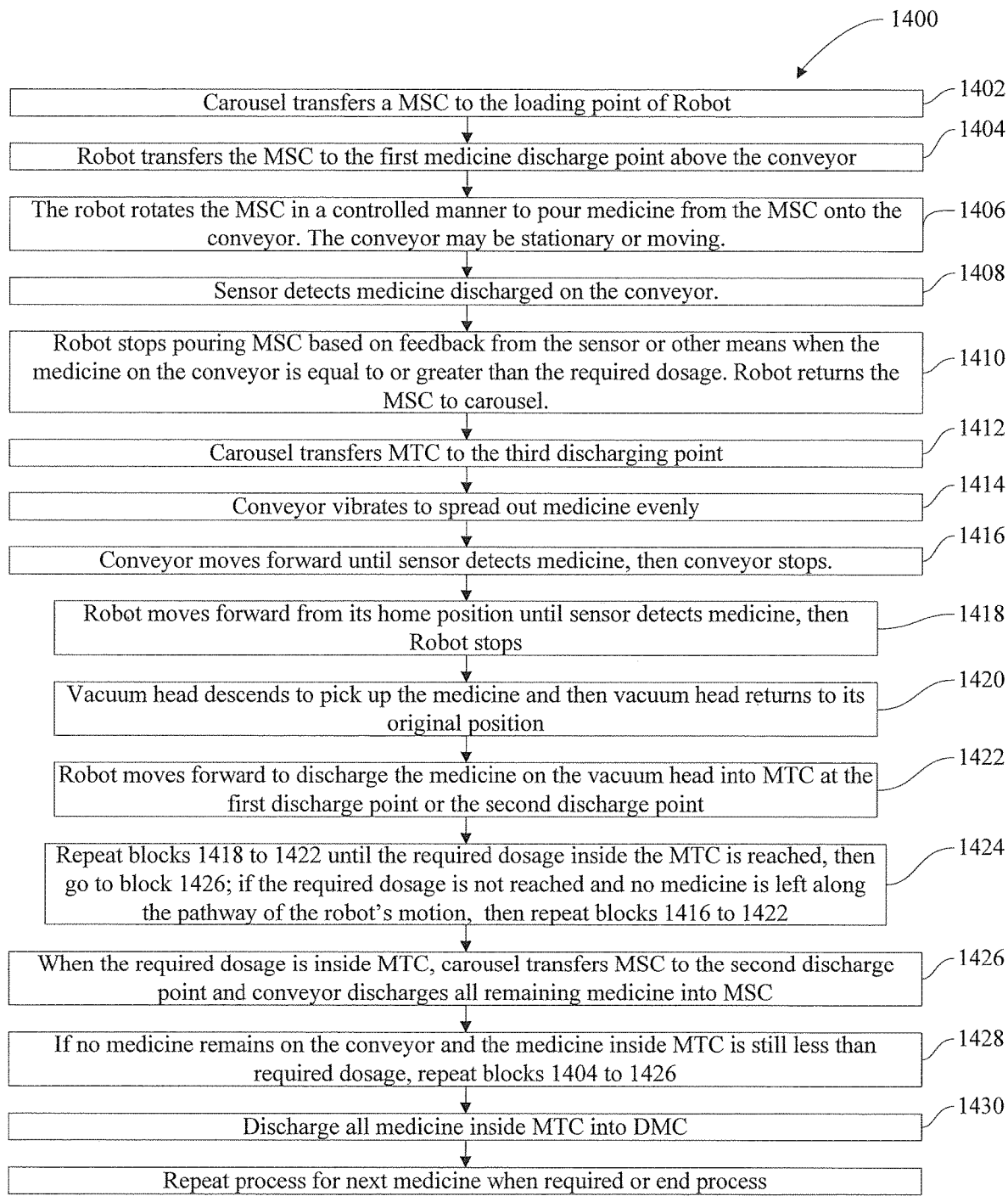
FIG. 14 is a flow diagram illustrating an exemplary process for dispensing a dose of medicine via the exemplary sub-assembly of FIG. 13A-13B.

Referring now to FIG. 14, a flow diagram of another exemplary process 1400 for operating the dispensing unit 102, which may incorporate the sub-assembly 1300, is illustrated. Process 1400 may include operations that may be part of program 110, stored on memory 108, and/or executed by processor 106. Process 1400 may take many different forms and include multiple and/or alternate steps. While an exemplary process is shown, the exemplary steps illustrated are not intended to be limiting. Indeed, additional or alternative steps and/or implementations may be used. In addition, for purposes of process 1400, the first medicine container transfer unit 330 is referred to as the carousel, and the second medicine container transfer unit 345 is referred to as the robot. However, it should be appreciated that any medicine container transfer unit 330, 345 for performing the respective step(s) is contemplated, and that the use of the terms carousel and robot are not intended to be limiting.

Blocks 1402 through 1410 may be the same or similar as blocks 1202 through 1210 of process 1200. Process 1400 may begin to diverge from process 1200 at block 1412 at which the carousel 310 may transfer a medicine transfer container 370, 375 to a medicine discharge point 1320 (as opposed to discharge point 380).

At block 1414, conveyor 1105 may vibrate to spread the medicine thereon out evenly.

At block 1416, conveyor 1105 may move forward until the sensor 1115 detects medicine, after which conveyor 1105 may stop.

At block 1418, robot 1345 may move forward from a home position until sensor 1330 detects medicine, after which robot 1345 may stop.

At block 1420, vacuum head 1315 may descend to pick up the medicine and then vacuum head 1315 may return to its original position.

At block 1422, robot 1345 may move forward to discharge the medicine on the vacuum head 1315 into the medicine transfer container 370, 375 at medicine discharge point 1320. Robot 1345 may also discharge the medicine on the vacuum head 1315 into the medicine transfer container 370,375 at medicine discharge point 380 (not shown). Robot 1345 may also pick up medicine from medicine transfer containers 370, 375 at medicine discharge point 380 or 1320 and discharge onto the medicine transfer unit 355.

At block 1424, processor 106 may determine if the medicine in the medicine transfer container 370, 375 has reached the required dosage. If it has, then process 1400 may proceed to block 1426. If it has not, and there is no medicine left along the pathway of the motion of robot 1345, then process 1400 may repeat blocks 1416 to 1422 until the required dosage has been reached, after which process 1400 may proceed to block 1426.

At block 1426, carousel 310 may transfer the medicine storage container 320 to the medicine discharge point 380, and conveyor 1105 may move forward to discharge all remaining medicine on the conveyor 1105 into the medicine storage container 320. Process 1400 may then proceed to block 1430.

At block 1428, processor 106 may determine if any medicine remains on the conveyor 1105. If not, and the medicine inside the medicine transfer container 370, 375 is still less than required dosage, blocks 1404 through 1426 may be repeated.

At block 1430, the medicine inside of the medicine transfer container 370, 375 may be discharged into the dispensed medicine container 365.

Process 1400 may be repeated for the next medicine when required or process 1400 may end.

In embodiments, scale(s) 395, for example, in each weighing station or storage nests associated with each container, may check quantity of medicine inside each container involved in process 1400, e.g., the medicine storage container 320, the medicine transfer containers 370, 375, and the dispensed medicine container 365.

In general, process 1400 may be a closed feedback loop process with stable and fast convergent iterations. In addition, the processor 106 may communicate with, i.e., send commands to, receive data from, and the like, to various components of the dispensing unit 102 and/or system 500 to perform process 1400, and may decide the best way to distribute the medicine among medicine storage container 320, the medicine transfer containers 370, 375, and the dispensed medicine container 365 based on process 1400.

Figure 15A:
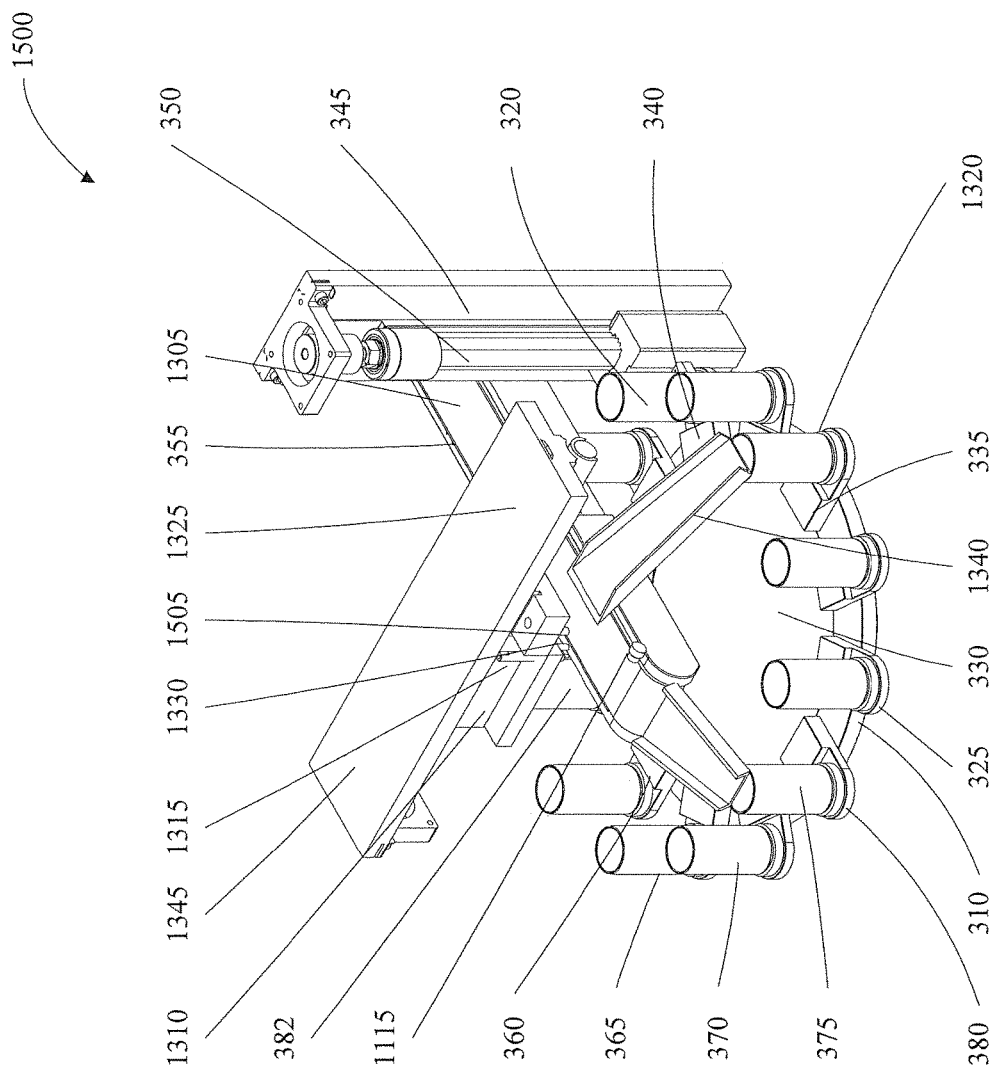
FIG. 15A is a perspective view of a sub-assembly according to another exemplary approach.

FIG. 15A illustrates an exemplary sub-assembly 1500 of dispenser 102 with a conveyor, a robot, a vacuum head (mounted on the same robot or a different robot), a vision system, and a carousel. In this example medicine container transfer unit 330 includes carousel 310, medicine container transfer unit 345 includes a robot with end of arm tool, medicine transfer unit 355 includes conveyor 1305, two sensors 1110 (not visible) and 1115, robot 1345 with end of arm tool 1310, sensor 1330, vacuum head 1315, and a machine vision system 1505 coupled to processor 106 and configured to output a visual location and images of items, such pills or capsules, of dispenser 102. Robot 345 and robot 1345 may be two different robots, or two different parts of the same one robot.

Figure 15B:
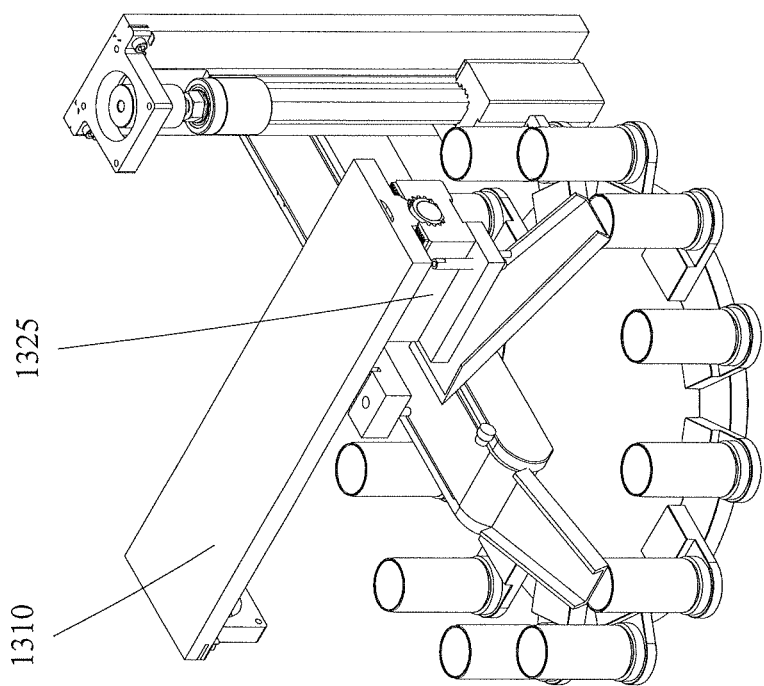
FIG. 15B illustrates the exemplary system of FIG. 15A during operation.

FIG. 15B shows end of arm tool 1310 at medicine discharge position 1325 to discharge medicine into the medicine storage container at the medicine container transfer unit 330 discharge position 1320. End of arm tool 1310 may also discharge medicine into medicine storage container at medicine container transfer unit 330 discharge position 380 (not shown).

FIG. 15A illustrates an exemplary sub-assembly 1500 of the disclosed system. Sub-assembly 1500 includes medicine container transfer unit 330 having carousel 310, medicine container transfer unit 345 includes a robot with end of arm tool. Medicine transfer unit 355 includes a robot or conveyor 1305, sensors 1110 (not visible) and 1115, robot 1345 having an end of arm tool (EOAT) 1310, a sensor 1330, and a vacuum head 1315. Medicine container transfer unit 345 and robot 1345 may be two different robots, or two different parts of the same one robot. FIG. 15B is a view of the example of FIG. 15A, showing end of arm tool 1310 at medicine discharge position 1325 to discharge medicine into medicine storage container at discharge position 1320. The end of arm tool 1310 may also discharge medicine into medicine storage container at medicine container transfer unit 330 discharge position 380 (not shown).

Sub-assembly 1500 is a view of inside elements of dispenser 102 and includes carousel 310. Sub-assembly 1500 includes loading station or medicine container loading station 325, first medicine container transfer unit 330, and medicine container storage nest 335. Medicine container loading point 340 is proximate second medicine container transfer unit 345. First medicine discharge point 350 includes, in the illustrated example, medicine transfer unit 355 that may include robot 1345 and conveyer 1305 for transporting or otherwise conveying medicine from the first medicine discharge point 350 to second medicine discharge point 380, and may include sensors 1110 (not visible) and 1115. Sub-assembly 1500 includes weight checking station 360, a calibration and verification device 382 to automatically calibrate weight detecting devices, dispensed medicine container 365, and medicine transfer container 370 and 375. Medicine storage container 320 is positioned on carousel 310.

FIG. 15A is an illustration of medicine storage container 320 as positioned proximate medicine container transfer unit 345, and FIG. 15B of the exemplary system of FIG. 15A shows end of arm tool 1310 at medicine discharge position 1325. Medicine storage container 320 may include original medicine container 390, medicine container identification unit 385, weight detecting device 395, and medicine container storage nest 335. Weight detecting device 395 and medicine container storage nest 335 may be integrated together. Weight detecting device 395 and medicine container storage nest 335 may also be part of carousel 310. Weight detecting device 395 may be a scale, a load cell, or other device for measuring weight, according to the disclosure. Weight detecting device 395 and medicine container storage nest 335 are positioned about carousel 310 at each of the illustrated locations. Medicine container identification unit 385 may include identification information particular to a given medicine, and may also identify an amount of medicine that may constitute a single patient dose particular to a given user of dispenser 102.

Referring still to FIG. 15A, medicine storage container 320 may be loaded into dispenser 102 from MCLS 325, and medicine storage container 320 is transferred to MCLP 340 by medicine container transfer unit 330. Medicine storage container 320 may include medicine in the form of a pill or a capsule, as examples, and a dose of medicine for a user may include one or more of the pills or capsules. Medicine container transfer unit 330 is illustrated as having carousel 310, but may instead include a conveyor, a robot, or any device that can move medicine storage container 320 from one position to another, and discharge medicine from medicine storage container 320.

Medicine transfer unit 355 moves medicine from one position to another, accepts medicine from medicine storage container 320, and medicine transfer unit 355 also discharges medicine into medicine storage container 320 or any container when positioned at medicine discharge point 380. Medicine transfer unit 355 may have a linear moving surface such as a walking beam, a conveyor, or a rotating surface such as a rotating disc or other shape, and includes in the illustrated example conveyer 1305.

In operation, as shown in FIGS. 15A and 15B, dispenser 102 moves, via carousel 310, medicine storage container 320 to loading point 312, and loading point 312 is proximate medicine container transfer unit 345. Medicine container transfer unit 345 engages with medicine storage container 320 by attaching thereto, and moving medicine storage container 320 to first medicine discharge point 350. Medicine container transfer unit 345 turns medicine storage container 320 such that at least a predetermined amount of medicine spills or otherwise pours from medicine storage container 320 onto medicine transfer unit 355, as determined by sensor or medicine weight detecting device on the medicine transfer unit 355. Carousel 310 rotates to move medicine transfer container 375 to second medicine discharge point 380. When medicine transfer container 375 is positioned at medicine discharge point 380, and when medicine has been discharged onto medicine transfer unit 355, medicine transfer unit 355 thereby conveys the discharged medicine from medicine transfer unit 355 into medicine transfer container 375 until at least a second predetermined amount of medicine is contained in medicine transfer container 375, as determined by weight detecting device 395 and MCSN 335, which weigh and transmit weight information to for instance a controller of dispenser 102.

Medicine transfer unit 355 includes robot 1345 and conveyor 1305, and sensors 1110 and 1115, which monitor medicine positioned on medicine transfer unit 355 and on conveyor 1305. Sensors 1110, 1115 may be optical sensors that are coupled, electrically or optically as examples, to processor 106. As such, processor 106 monitors medicine positioned on medicine transfer unit 355 via sensors 1110, 1115. Sensors 1110 and 1115 detect the presence of pills or capsules as they pass thereby via medicine transfer unit 355 to second medicine discharge point 380. In addition, robot 1345 includes end of arm tool 1310 having vacuum head 1315 that may attach via a vacuum, controlled by processor 106, to individual pills or capsules passing along medicine transfer unit 355. Accordingly, in this example, pills or capsules may be not only conveyed by conveyor 1305 to medicine transfer container 370 or medicine transfer container 375 when positioned at medicine discharge point 380, but also conveyed by robot 1345 to medicine transfer container 370 or 375 when positioned at medicine discharge point 380. Pills or capsules may also be conveyed by robot 1345 to medicine transfer container 370 or 375 positioned at position 1320. Pills or capsules may also be conveyed by robot 1345 from medicine transfer containers 370 or 375 at discharge point 380 or 1320 back to the medicine transfer unit 355. Both methods may be used concurrently or separately. Thus, overall efficiency or movement of pills or capsules may be improved by having an ability to move pills or capsules to two locations simultaneously.

Medicine is transferred from medicine transfer unit 355 into medicine transfer container 375, and a weight of the medicine is determined via weight detecting device 395. If the measured weight is less than a given or desired dose, and if medicine is still on medicine transfer unit 355 (i.e., has not been fully discharged), then medicine transfer unit 355 further conveys more medicine into medicine transfer container 375. On the other hand, if no medicine is on medicine transfer unit 355, then additional medicine is discharged to medicine transfer unit 355 from medicine storage container 320. The process of discharging from medicine storage container 320 to medicine transfer unit 355, and from medicine transfer unit 355 to medicine transfer container 375 continues until at least a dose of medicine is contained in medicine transfer container 375. That is, medicine transfer container 375 may include an exact or desired dose, or may include an amount of medicine that is in excess of an exact dose.

If an exact dose is present in medicine transfer container 375, then dispenser 102 operates to convey medicine transfer container 375 to first medicine discharge point 350 via medicine container transfer unit 345, any remaining medicine on medicine transfer unit 355 is discharged back into medicine storage container 320 at second medicine discharge point 380, and the medicine in medicine transfer container 375 is discharged into dispensed medicine container 365 that is positioned at second medicine discharge point 380.

On the other hand, in one example medicine transfer container 375 may include an amount of medicine that is in excess of an exact dose. In such an example, medicine transfer container 375 is thereby conveyed to first medicine discharge point 350 and operations described above are repeated. That is, medicine container transfer unit 345 discharges medicine from medicine transfer container 375 onto medicine transfer unit 355, and then medicine transfer container 375 is conveyed via carousel 310 to second medicine discharge point 380. Medicine discharged from medicine transfer container 375 to medicine transfer unit 355 is thereby conveyed to medicine transfer container 375 until at least the exact dose is present in medicine transfer container 375. And, again, if medicine transfer container 375 includes medicine equal to the dose, then the medicine in medicine transfer container 375 is discharged into dispensed medicine container 365, and any excess medicine on medicine transfer unit 355 is returned to medicine storage container 320.

The aforementioned steps continue until a dose of medicine is contained within dispensed medicine container 365, and any additional medicine is returned to medicine storage container 320. In such fashion, dispenser 102 includes a feedback mechanism, ensuring a proper dose, and only a proper dose, is contained in dispensed medicine container 365. That is, feedback is provided in the form of a weight of pills or capsules, corresponding to a dose, measured via weight detecting device 395. Dispenser 102 is caused to operate using such feedback to ensure that a correct dose is provided in dispensed medicine container 365. However, in the illustrated example, medicine, in this example, may be conveyed to and from medicine transfer container 370 or medicine transfer container 375 positioned at discharge position 1320 and 380 in both directions, allowing simultaneous or sequential iterations using two containers and two conveying methods in both directions, which may allow convergence to a final dose, and movement of any additional medicine from medicine transfer unit 355 via a second path (i.e., via vacuum head 1315, for containers positioned at position 1320 and 380). Additionally, vision system 1505 provides yet additional functionality, in that vision system 1505 may convey an image of pills or capsules passing along medicine transfer unit 355, providing a visual representation of the pills or capsules, and an additional method of identifying the movement thereof into medicine transfer container 370 and/or medicine transfer container 375. Processor 106 may compare these images with images stored in database 122 to make sure correct medicine is dispensed.

Figure 16:
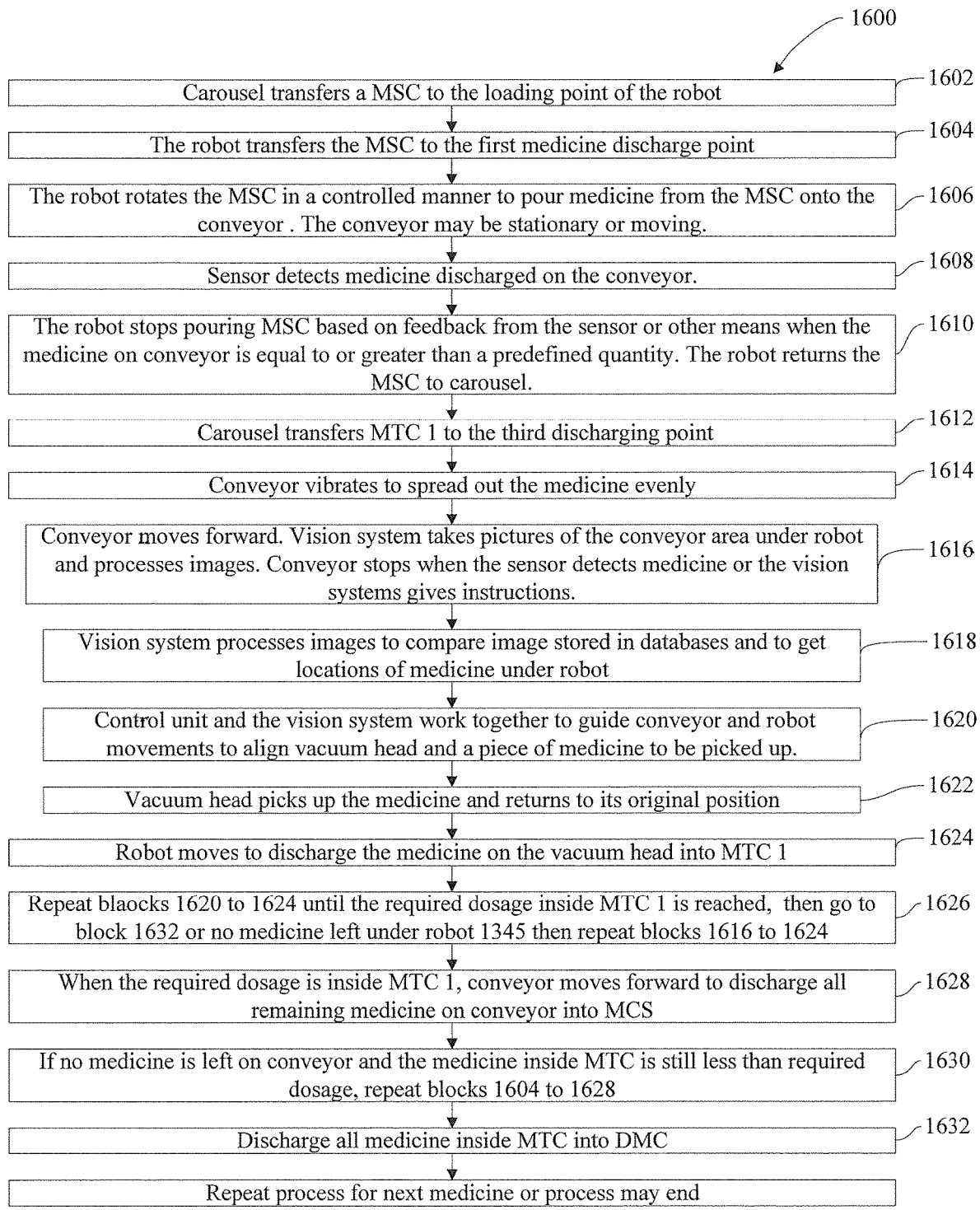
FIG. 16 is a flow diagram illustrating an exemplary process for dispensing a dose of medicine via the exemplary sub-assembly of FIG. 15A-15B.

Referring now to FIG. 16, a flow diagram of another exemplary process 1600 for operating the dispensing unit 102, which may incorporate the sub-assembly 1500, is illustrated. Process 1600 may include operations that may be part of program 110, stored on memory 108, and/or executed by processor 106. Process 1600 may take many different forms and include multiple and/or alternate steps. While an exemplary process is shown, the exemplary steps illustrated are not intended to be limiting. Indeed, additional or alternative steps and/or implementations may be used. In addition, for purposes of process 1600, the first medicine container transfer unit 330 is referred to as the carousel, and the second medicine container transfer unit 345 is referred to as the robot. However, it should be appreciated that any medicine container transfer unit 330, 345 for performing the respective step(s) is contemplated, and that the use of the terms carousel and robot are not intended to be limiting.

Process 1600 generally may be the same as or similar to process 1400, but may differ in the incorporation of the vision system 1505. For example, blocks 1602 through 1610 may correspond to blocks 1402 through 1414 of process 1400. Process 1600 may begin to diverge from process 1400 at block 1616 at which the conveyor 1105 may move forward, and the vision system 1505 may take pictures of the area of the conveyor 1105 and process the images. Conveyor 1105 may stop when the sensor 1115 detects medicine or the vision system 1505 gives instructions.

At block 1618, the vision system 1505 may process the images to determine correct medicine is dispensed and locations of the medicine on the conveyor 1105 under robot 1345.

At block 1620, the processor 106 and the vision system 1505 may work together to guide conveyor 1105 and robot 1345 movements to align vacuum head 1315 and a piece of medicine to be picked up.

The remaining blocks 1622 through 1632 may correspond with blocks 1420 through 1430 of process 1400.

Process 1600 may be repeated for the next medicine when required or the process 1600 may end.

In embodiments, scale(s) 395, for example, in each weighing station or storage nests associated with each container, may check quantity of medicine inside each container involved in process 1600, e.g., the medicine storage container 320, the medicine transfer containers 370, 375, and the dispensed medicine container 365.

In general, process 1600 may be a closed feedback loop process with stable and fast convergent iterations. In addition, the processor 106 may communicate with, i.e., send commands to, receive data from, and the like, to various components of the dispensing unit 102 and/or system 500 to perform process 1600, and may decide the best way to distribute the medicine among medicine storage container 320, the medicine transfer containers 370, 375, and the dispensed medicine container 365 based on process 1600.

Figure 17A:
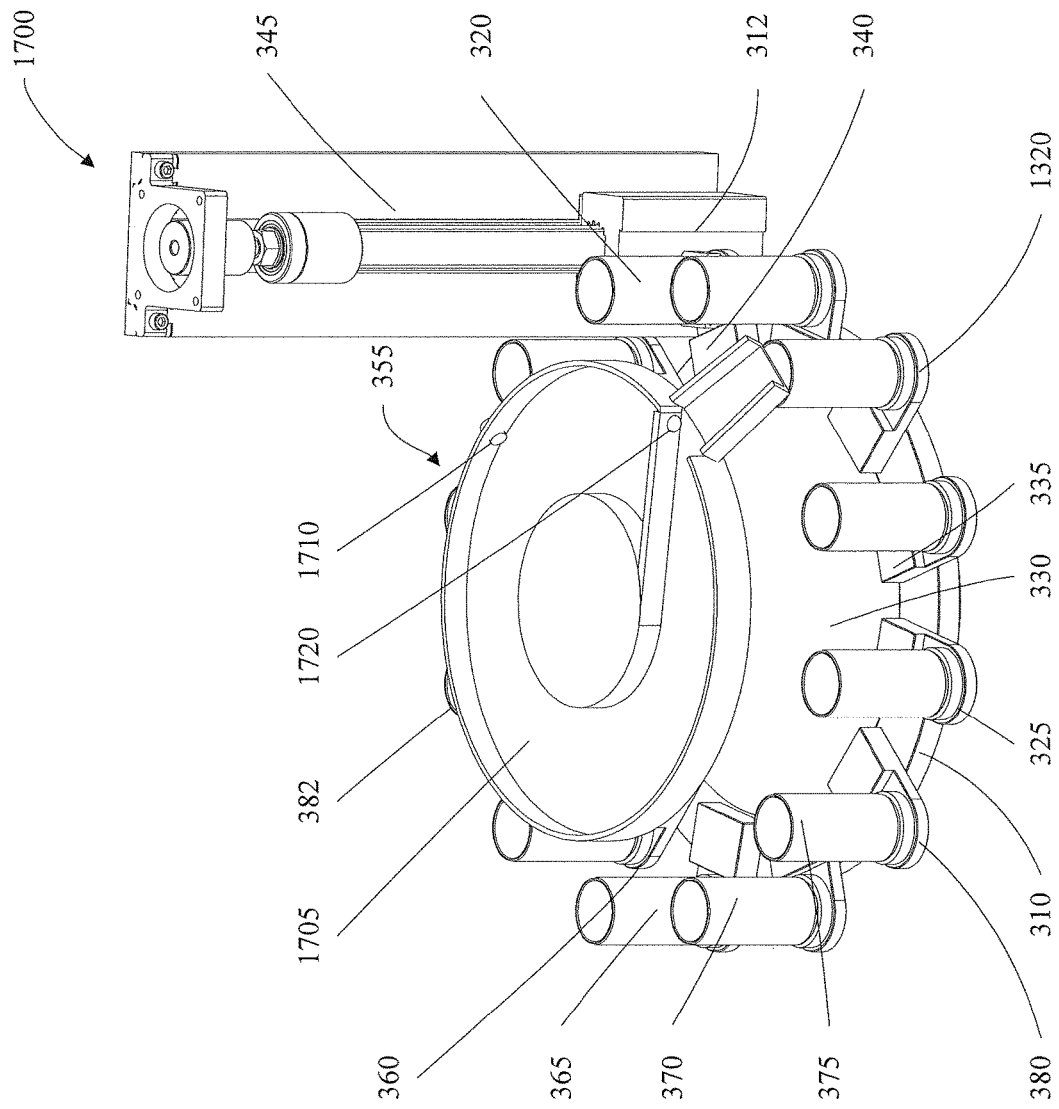
FIG. 17A is a perspective view of a sub-assembly according to another exemplary approach.
Figure 17B:
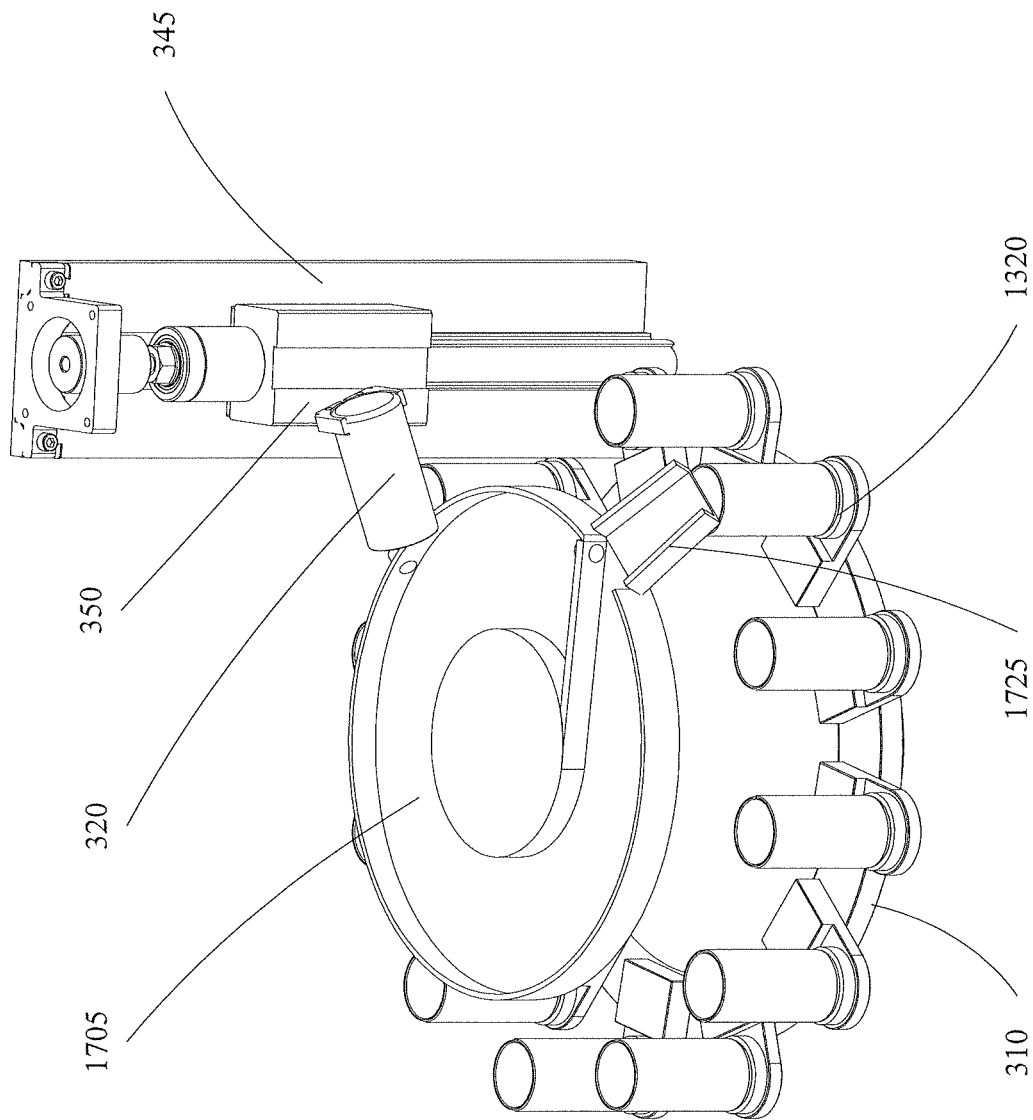
FIG. 17B illustrates the exemplary system of FIG. 17A during operation.
Figure 17C:
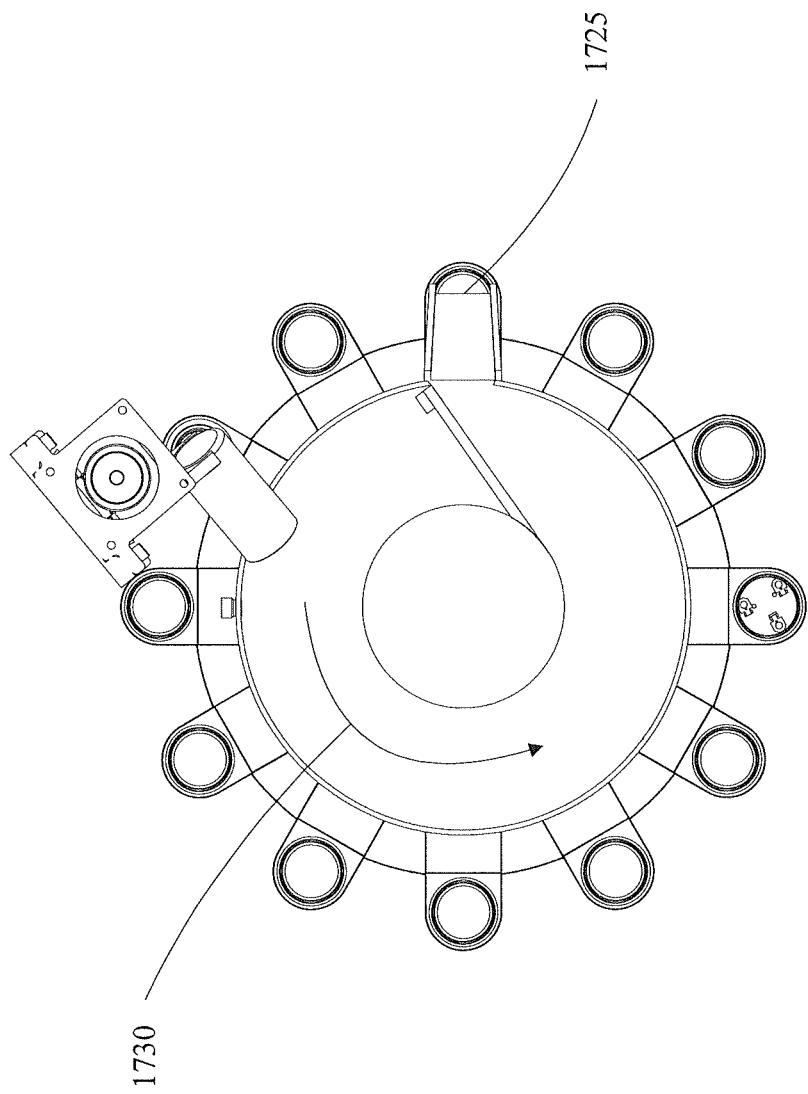
FIG. 17C illustrates a top view of the exemplary system of FIG. 17B.

FIG. 17A illustrates an exemplary sub-assembly 1700 of the disclosed dispenser 102. FIG. 17B illustrates the exemplary system of FIG. 17A during operation. FIG. 17C illustrates a top view of the exemplary system of FIGS. 17A and 17B.

FIG. 17A is an example of dispenser 102 having a rotating table, a robot, and a carousel. In this example medicine container transfer unit 330 includes carousel 310 and robot 345, medicine transfer unit 355 includes a rotating table 1705 and sensors 1710 and 1720. FIG. 17B shows medicine storage container 320 transferred to medicine discharge point 350 by medicine container transfer unit 345 to discharge medicine from the medicine storage container 320 to rotating table 1705. Sensors 1710 and 1720 monitor the medicine on table 1705.

FIG. 17A illustrates the disclosed dispenser 102 having rotating table 1705 and sensors 1710 and 1720. In this example medicine container transfer unit 330 includes carousel 310, and medicine container transfer unit 345 includes table 1705 on which pills or capsules may be placed, such that they may roll or otherwise move in a generally circular fashion to discharge position 1320.

FIG. 17B is a view of sub-assembly as shown in FIG. 17A, showing medicine storage container 320 transferred to first medicine discharge point 350 by medicine container transfer unit 345 to discharge medicine from medicine storage container 320 to table 1705.

FIG. 17A illustrates an exemplary sub-assembly 1700 illustrating the disclosed system or dispenser. Sub-assembly 1700 is a view of inside elements of dispenser 102 and includes carousel 310. Sub-assembly 1700 includes medicine container transfer unit 330, and medicine container storage nest 335. Medicine container loading point 340 is proximate medicine container transfer unit 345. Sub-assembly 1700 includes weight checking station 360, a calibration and verification device 382 to automatically calibrate weight detecting devices, dispensed medicine container 365, and medicine transfer container 370 and 375. Medicine storage container 320 is positioned on carousel 310.

In operation, carousel 310 moves medicine storage container 320 to loading point 312, and loading point 312 is proximate medicine container transfer unit 345. Medicine container transfer unit 345 engages with medicine storage container 320 by attaching thereto, and moves medicine storage container 320 to first medicine discharge point 350. Medicine storage container 320 is, in one example, a medicine storage container which may have an amount of medicine that is in excess of a dose, or an amount of medicine that is desired to be distributed into dispensed medicine container 365. Medicine container transfer unit 345 turns medicine storage container 320 such that a predetermined amount of medicine spills or otherwise pours from medicine storage container 320 onto rotating table 1705, as illustrated in FIG. 17B. Rotating table 1705 is configured to rotate or jostle back and forth, causing items such as pills or capsules thereon to jostle or vibrate, such that the items pass about a circumference of rotating table 1705 and in a rotational direction 1730 to a chute 1725.

When medicine transfer container 370 is positioned at discharge position 1320, and when medicine has been discharged onto rotating table 1705, rotating table 1705 thereby conveys the discharged medicine from rotating table 1705 into medicine transfer container 370 positioned at discharge position 1320, until at least a second predetermined amount of medicine is contained in medicine transfer container 370, as determined by weight detecting device 395 and medicine container storage nest 335, which weigh and transmit weight information to for instance a controller of dispenser 102.

Medicine is transferred from rotating table 1705 into medicine transfer container 370, and a weight of the medicine is determined via weight detecting device 395. If the medicine is less than a given or desired dose, and if medicine is still on rotating table 1705 (i.e., has not been fully discharged), then rotating table 1705 further conveys more medicine into medicine transfer container 370. On the other hand, if no medicine is on rotating table 1705, then additional medicine is discharged to rotating table 1705 from medicine storage container 320. The process of discharging from medicine storage container 320 to rotating table 1705, and from rotating table 1705 to medicine transfer container 370 continues until at least a dose of medicine is contained in medicine transfer container 370. That is, medicine transfer container 370 may include an exact or desired dose, or may include an amount of medicine that is in excess of an exact dose.

If an exact dose is present in medicine transfer container 370, then dispenser 102 operates to convey medicine transfer container 370 to discharge position 350 via medicine container transfer unit 345, any remaining medicine on rotating table 1705 is discharged back into medicine storage container 320, and the medicine in medicine transfer container 370 is discharged into dispensed medicine container 365.

On the other hand, in one example medicine transfer container 370 may include an amount of medicine that is in excess of an exact dose. In such an example, medicine transfer container 370 is thereby conveyed to first medicine discharge point 350 and operations described above are repeated. That is, medicine container transfer unit 345 discharges medicine from medicine transfer container 370 onto the rotating table 1705, and then medicine transfer container 370 (or medicine transfer container 375) is conveyed via carousel 310 to medicine discharge point 1320. Medicine discharged from medicine transfer container 370 to the rotating table 1705 is thereby conveyed to medicine transfer container 370 (or 375) until at least the exact dose is present in medicine transfer container 370 (or 375). And, again, if medicine transfer container 370 (or 375) includes medicine equal to the dose, then the medicine in medicine transfer container 370 (or 375) is discharged into dispensed medicine container 365, and any excess medicine on the rotating table 1705 is returned to medicine storage container 320.

The aforementioned steps continue until a dose of medicine is contained within dispensed medicine container 365, and any additional medicine is returned to medicine storage container 320. In such fashion, dispenser 102 includes a feedback mechanism, ensuring a proper dose, and only a proper dose, is contained in dispensed medicine container 365. That is, feedback is provided in the form of a weight of pills or capsules, corresponding to a dose, measured via weight detecting device. Dispenser 102 is caused to operate using such feedback to ensure that a correct dose is provided in dispensed medicine container 365.

Figure 18:
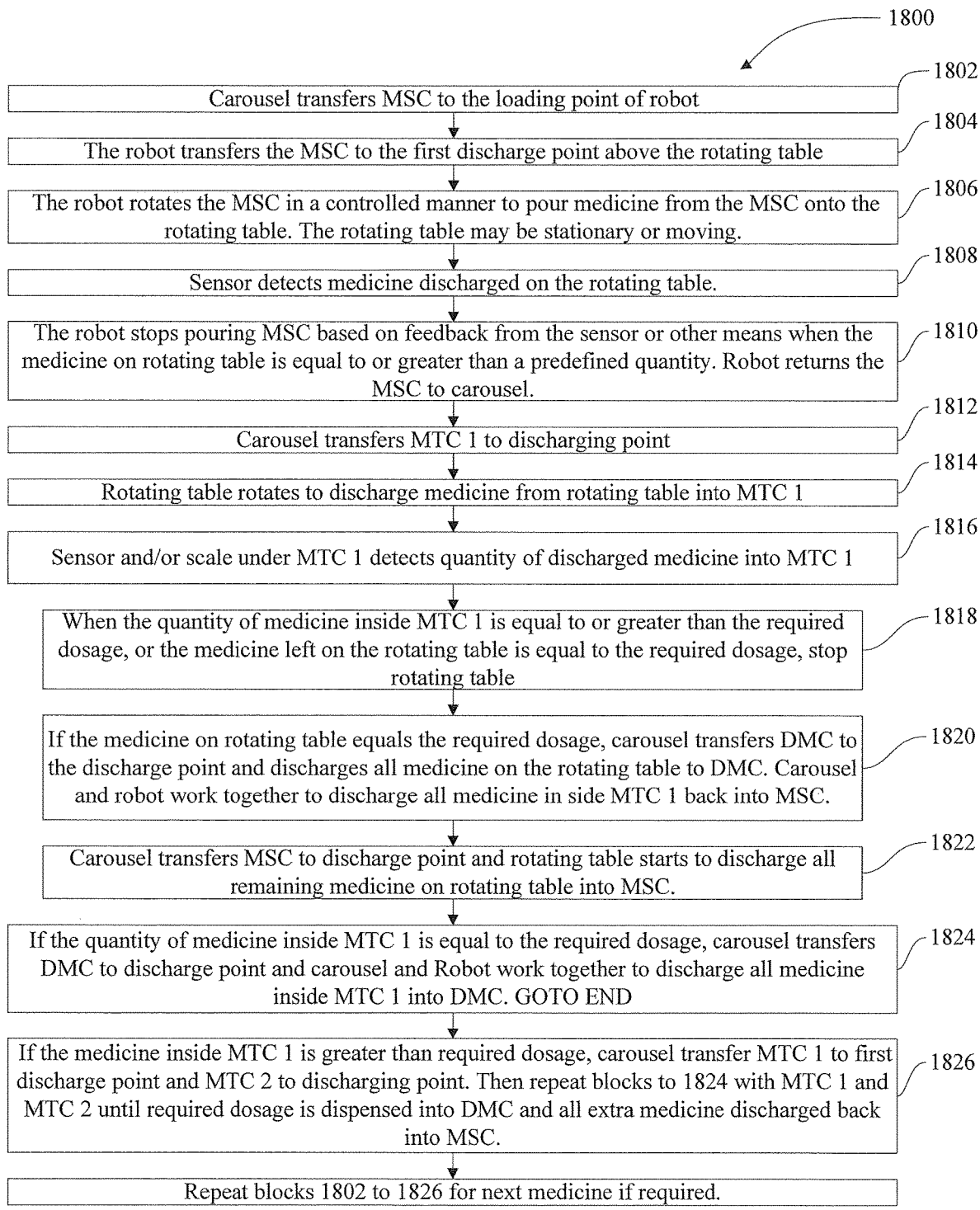
FIG. 18 is a flow diagram illustrating an exemplary process for dispensing a dose of medicine via the exemplary sub-assembly of FIG. 17A-17C.

Referring now to FIG. 18, a flow diagram of another exemplary process 1800 for operating the dispensing unit 102, which may incorporate the sub-assembly 1700, is illustrated. Process 1800 may include operations that may be part of program 110, stored on memory 108, and/or executed by processor 106. Process 1800 may take many different forms and include multiple and/or alternate steps. While an exemplary process is shown, the exemplary steps illustrated are not intended to be limiting. Indeed, additional or alternative steps and/or implementations may be used. In addition, for purposes of process 1800, the first medicine container transfer unit 330 is referred to as the carousel, and the second medicine container transfer unit 345 is referred to as the robot. However, it should be appreciated that any medicine container transfer unit 330, 345 for performing the respective step(s) is contemplated, and that the use of the terms carousel and robot are not intended to be limiting.

Process 1800 generally may be the same as or similar to process 1200, but may differ in the incorporation of a rotating table 1705 and corresponding sensors 1410, 1420, in lieu of the conveyor 1105 and sensor 1110, 1115. In addition, the medicine transfer container 375 and the dispensed medicine container 365 are moved to medicine discharge point 1715 at blocks 1812, 1822, and 1824, as opposed to medicine discharge point 380 in process 1200. However, it should be appreciated that in some embodiments, the medicine discharge point 1715 may be the same as medicine discharge point 380.

Process 1800 may be repeated for the next medicine when required or process 1800 may end.

In embodiments, scale(s) 395, for example, in each weighing station or storage nests associated with each container, may check quantity of medicine inside each container involved in process 1800, e.g., the medicine storage container 320, the medicine transfer containers 370, 375, and the dispensed medicine container 365.

In general, process 1800 may be a closed feedback loop process with stable and fast convergent iterations. In addition, the processor 106 may communicate with, i.e., send commands to, receive data from, and the like, to various components of the dispensing unit 102 and/or system 500 to perform process 1800, and may decide the best way to distribute the medicine among medicine storage container 320, the medicine transfer containers 370, 375, and the dispensed medicine container 365 based on process 1800.

Figure 19A:
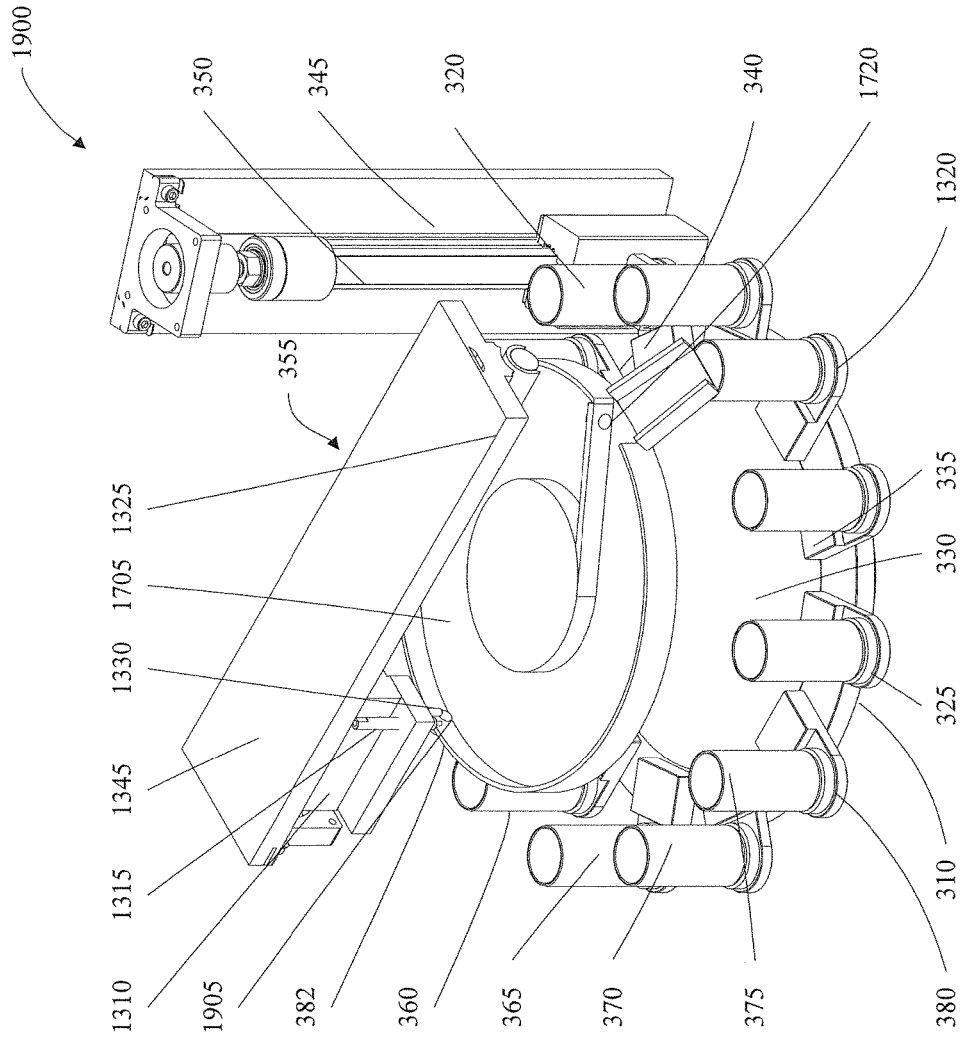
FIG. 19A is a perspective view of a sub-assembly according to another exemplary approach.
Figure 19B:
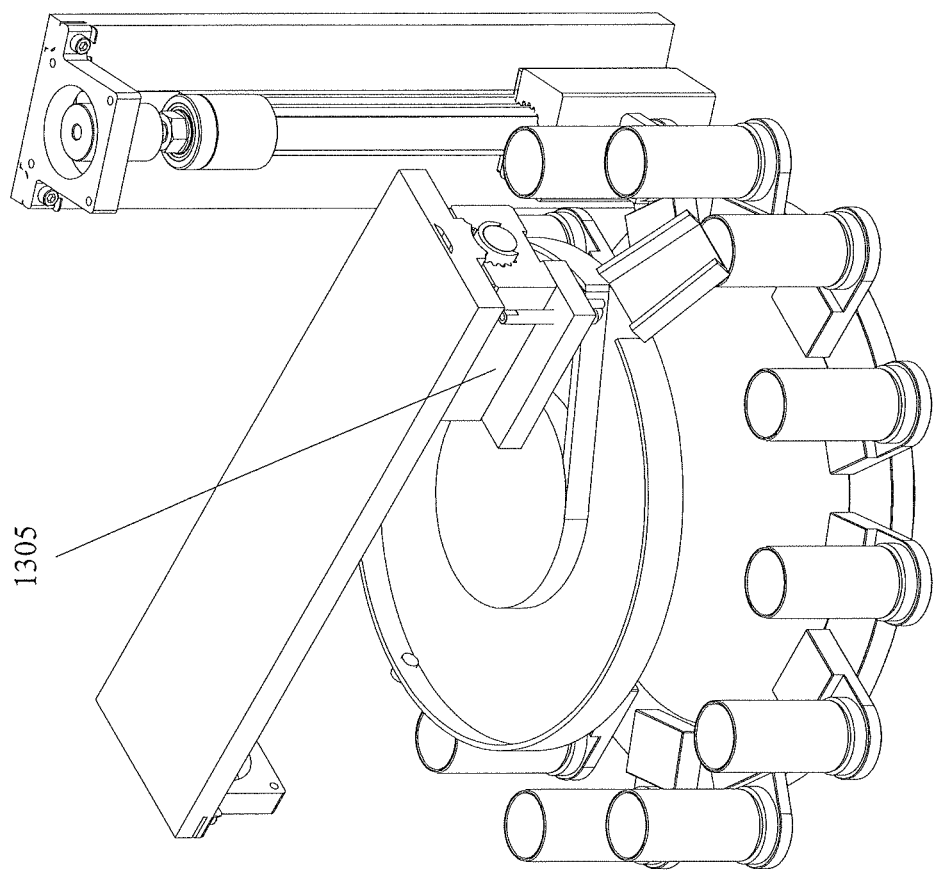
FIG. 19B illustrates the exemplary system of FIG. 19A during operation.

FIG. 19A illustrates an exemplary sub-assembly 1900 of the disclosed dispenser 102. FIG. 19B illustrates the exemplary sub-assembly of FIG. 19A during operation.

Sub-assembly 1900 includes medicine container transfer unit 330 includes having carousel 310, and medicine container transfer unit 345 includes a robot with end of arm tool. Medicine transfer unit 355 includes a rotating table 1705, two sensors 1710 (not visible) and 1720, and robot 1345 having end of arm tool 1310, another sensor 1330, and vacuum head 1315. Sensor 1905 is additionally positioned orthogonal to a surface of table 1705. Robot or medicine container transfer unit 345 and robot 1345 may be two different robots, or two different parts of the same one robot.

Sub-assembly 1900 includes weight checking station 360, a calibration and verification device 382 (not visible) to automatically calibrate weight detecting devices, dispensed medicine container 365, and medicine transfer container 370 and 375. Medicine storage container 320 is positioned on carousel 310. FIG. 19B shows end of arm tool 1310 at medicine discharge position 1325 to discharge medicine into the medicine storage container 320 at medicine container transfer unit 330 discharge position 1320.

Figure 20:
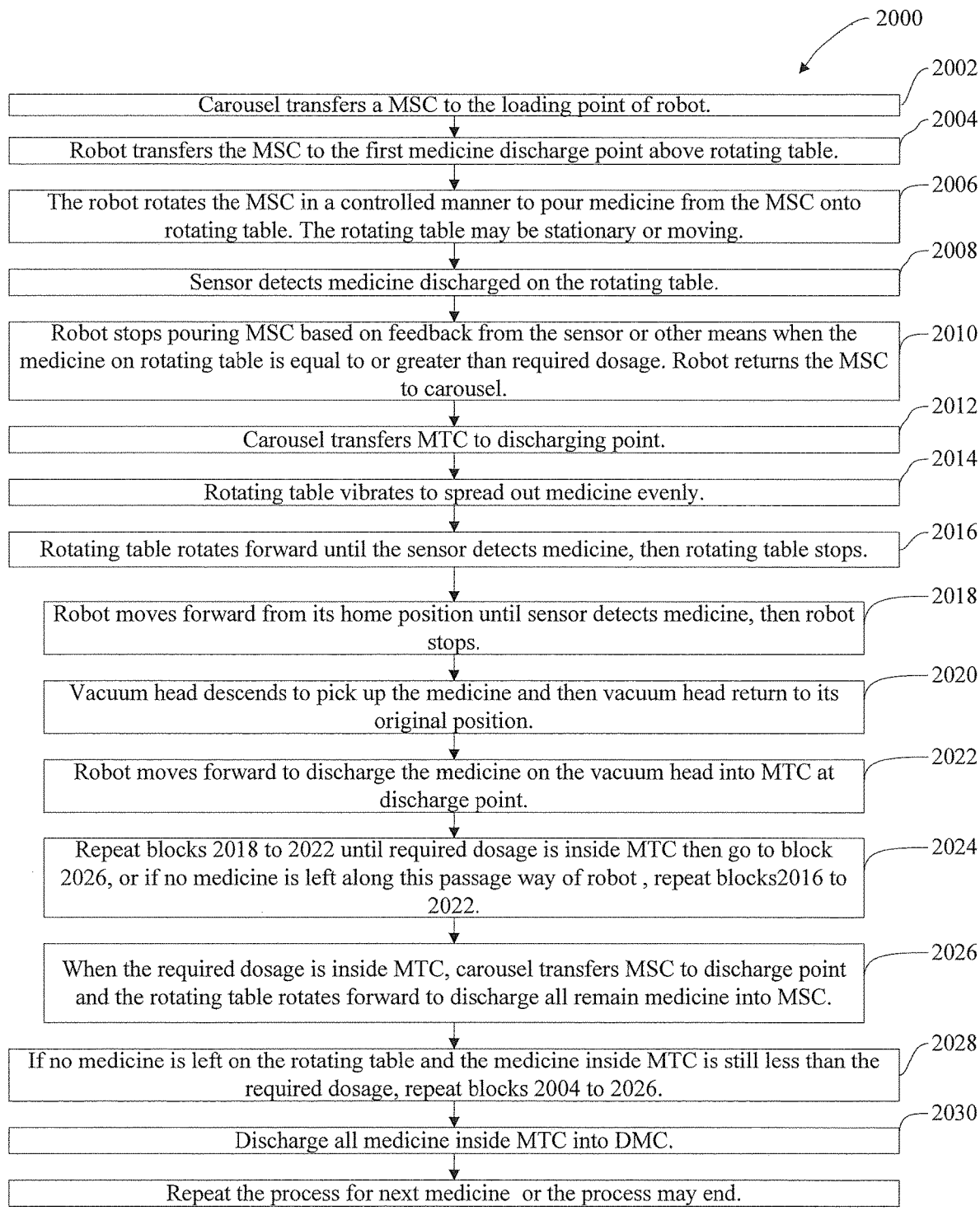
FIG. 20 is a flow diagram illustrating an exemplary process for dispensing a dose of medicine via the exemplary sub-assembly of FIG. 19A-19B.

Referring now to FIG. 20, a flow diagram of another exemplary process 2000 for operating the dispensing unit 102, which may incorporate the sub-assembly 1100, is illustrated. Process 2000 may include operations that may be part of program 110, stored on memory 108, and/or executed by processor 106. Process 2000 may take many different forms and include multiple and/or alternate steps. While an exemplary process is shown, the exemplary steps illustrated are not intended to be limiting. Indeed, additional or alternative steps and/or implementations may be used. In addition, for purposes of process 2000, the first medicine container transfer unit 330 is referred to as the carousel, and the second medicine container transfer unit 345 is referred to as the robot. However, it should be appreciated that any medicine container transfer unit 330, 345 for performing the respective step(s) is contemplated, and that the use of the terms carousel and robot are not intended to be limiting.

Blocks 2002 through 2012 may be the same or similar as blocks 1802 through 1812 of process 1800. Process 2000 may begin to diverge from process 1800 at block 2014 at which the rotating table 1705 may vibrate to spread out medicine evenly.

At block 2016, the rotating table 1705 may rotate until a sensor 1905 detects medicine, after which the rotating table 1705 may stop.

At block 2018, robot 1345 may move forward from a home position until sensor 1330 detects medicine on the rotating table 1705, after which robot 1305 may stop.

At block 2020, vacuum head 1315 may descend to pick up the medicine and then vacuum head 1315 may return to its original position.

At block 2022, robot 1345 may move forward to discharge the medicine on the vacuum head 1315 into the medicine transfer container 370, 375 at medicine discharge point 1320. Robot 1345 may also discharge the medicine on the vacuum head 1315 into the medicine transfer container 370, 375 at medicine discharge point 380 (not shown). Robot 1345 may also pick up medicine from medicine transfer containers 370,375 at medicine discharge point 380 or 1320 and discharge onto the medicine transfer unit 355.

At block 2024, processor 106 may determine if the medicine in the medicine transfer container 370, 375 has reached the required dosage. If it has, then process 2000 may proceed to block 2026. If it has not, and there is no medicine left along the pathway of the motion of robot 1345, then process 2000 may repeat blocks 2016 to 2022 until the required dosage has been reached, after which process 2000 may proceed to block 2026.

At block 2026, carousel 310 may transfer the medicine storage container 320 to the medicine discharge point 1320, and rotating table 1705 may rotate to discharge all remaining medicine on the rotating table 1705 into the medicine storage container 320. Process 2000 may then proceed to block 2030.

At block 2028, processor 106 may determine if any medicine remains on the rotating table 1705. If no, and the medicine inside the medicine transfer container 370, 375 is still less than required dosage, blocks 2004 through 2026 may be repeated.

At block 2030, all the medicine inside of the medicine transfer container 370 or 375 may be discharged into the dispensed medicine container 365.

Process 2000 may be repeated for the next medicine when required or process 2000 may end.

In embodiments, scale(s) 395, for example, in each weighing station or storage nests associated with each container, may check quantity of medicine inside each container involved in process 2000, e.g., the medicine storage container 320, the medicine transfer containers 370, 375, and the dispensed medicine container 365.

In general, process 2000 may be a closed feedback loop process with stable and fast convergent iterations. In addition, the processor 106 may communicate with, i.e., send commands to, receive data from, and the like, to various components of the dispensing unit 102 and/or system 500 to perform process 2000, and may decide the best way to distribute the medicine among medicine storage container 320, the medicine transfer containers 370, 375, and the dispensed medicine container 365 based on process 2000.

Figure 21A:
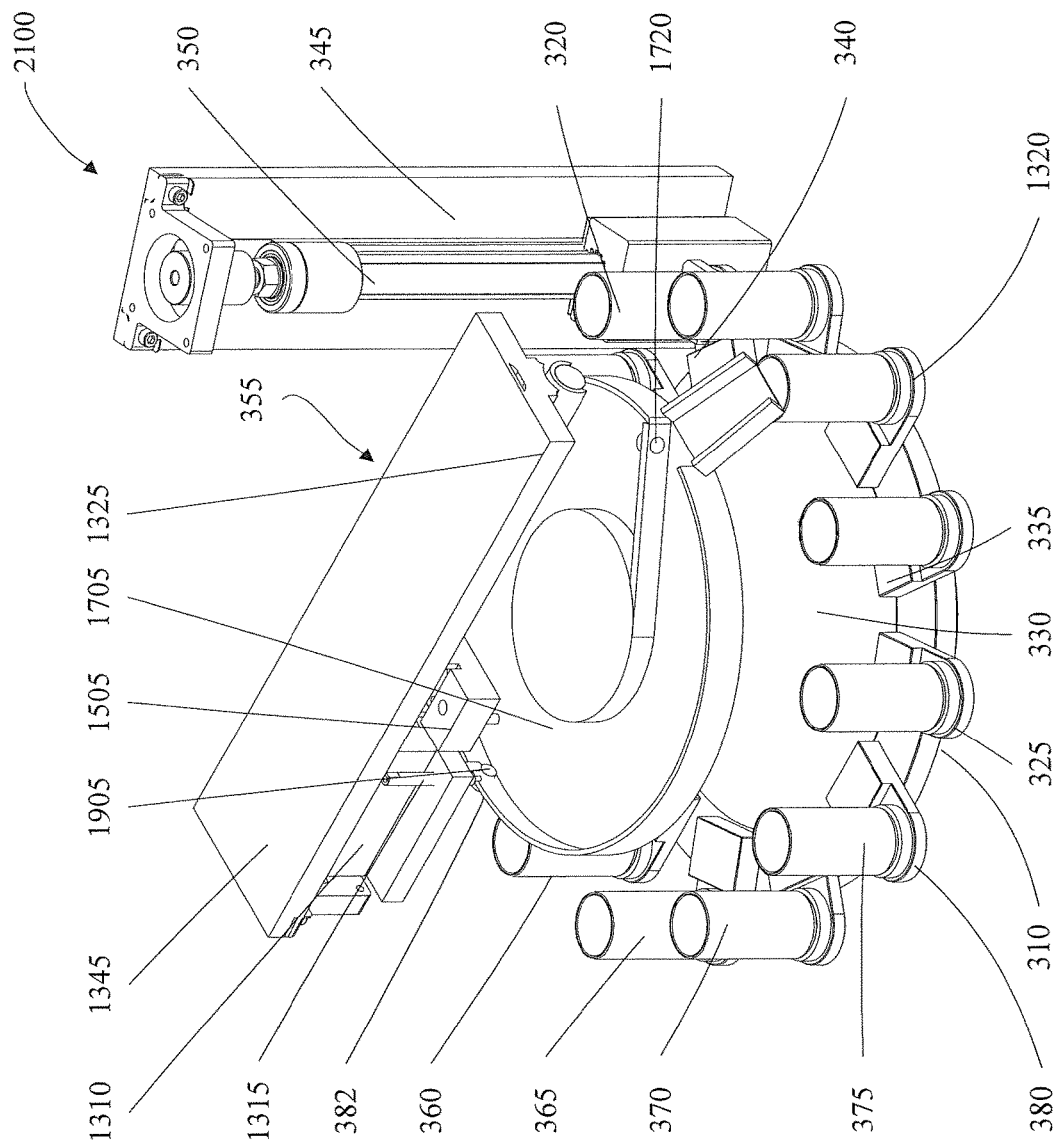
FIG. 21A is a perspective view of a sub-assembly according to another exemplary approach.
Figure 21B:
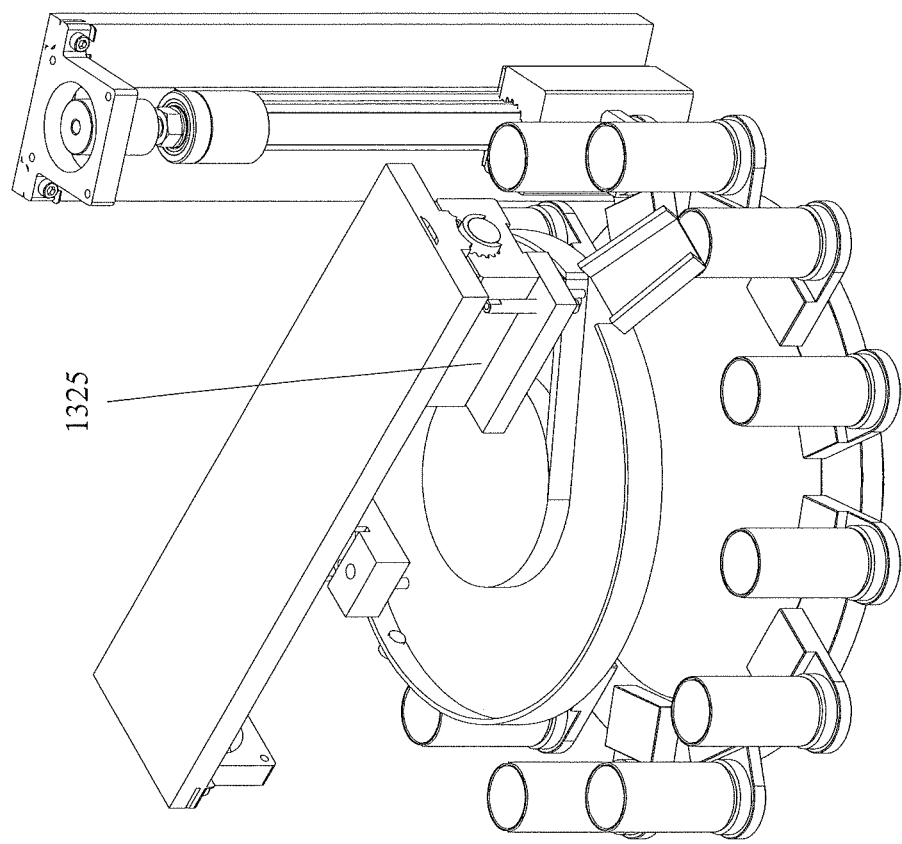
FIG. 21B illustrates the exemplary system of FIG. 19A during operation.

FIG. 21A illustrates an exemplary sub-assembly 2100 of the disclosed dispenser 102. FIG. 21B illustrates dispenser 102 having a rotating table, a robot, a vacuum head (mounted on the same robot or a different robot), a vision system, and a carousel. Sub-assembly 2100 illustrates medicine container transfer unit 330 having carousel 310, and medicine container transfer unit 345 includes a robot with end of arm tool. Medicine transfer unit 355 includes a rotating table 1705, three sensors 1710 (not visible), 1720 and 1905, another robot with 1345 with end of arm tool 1310, vacuum head 1315, and machine vision system 1505. Robot 345 and robot 1345 may be two different robots, or two different parts of the same one robot. Sub-assembly 2100 includes weight checking station 360, a calibration and verification device 382 (not visible) including to automatically calibrate weight detecting devices, dispensed medicine container 365, and medicine transfer container 370 and 375. Medicine storage container 320 is positioned on carousel 310.

FIG. 21B shows the end of arm tool 1310 at medicine discharge position 1325 to discharge medicine into the medicine storage container 320 at medicine container transfer unit 330 discharge position 1320.

Figure 22:
FIG. 22 is a flow diagram illustrating an exemplary process for dispensing a dose of medicine via the exemplary sub-assembly of FIG. 21A-21B.

Referring now to FIG. 22, a flow diagram of another exemplary process 2200 for operating the dispensing unit 102, which may incorporate the sub-assembly 2100, is illustrated. Process 2200 may include operations that may be part of program 110, stored on memory 108, and/or executed by processor 106. Process 2200 may take many different forms and include multiple and/or alternate steps. While an exemplary process is shown, the exemplary steps illustrated are not intended to be limiting. Indeed, additional or alternative steps and/or implementations may be used. In addition, for purposes of process 2200, the first medicine container transfer unit 330 is referred to as the carousel, and the second medicine container transfer unit 345 is referred to as the robot. However, it should be appreciated that any medicine container transfer unit 330, 345 for performing the respective step(s) is contemplated, and that the use of the terms carousel and robot are not intended to be limiting.

Process 2200 generally may combine various blocks from the different processes 1000, 1200, 1400, 1600, 1800 and/or 2000 described above. For example, blocks 2202 through 2214 correspond to blocks 2002 through 2014 of process 2000. The remaining blocks of process 2200 may correspond to blocks 1616 through 1632 of process 1600, where process 2200 differs in the use of rotating table 1705 in place of the conveyor 1105, and sensor 2205 in place of sensor 1115.

As with the other processes described above, process 2200 may be repeated for the next medicine when required.

In embodiments, scale(s) 395, for example, in each weighing station or storage nests associated with each container, may check quantity of medicine inside each container involved in process 2200, e.g., the medicine storage container 320, the medicine transfer containers 370, 375, and the dispensed medicine container 365.

In general, process 2200 may be a closed feedback loop process with stable and fast convergent iterations. In addition, the processor 106 may communicate with, i.e., send commands to, receive data from, and the like, to various components of the dispensing unit 102 and/or system 500 to perform process 2200, and may decide the best way to distribute the medicine among medicine storage container 320, the medicine transfer containers 370, 375, and the dispensed medicine container 365 based on process 2200.

Figure 23:
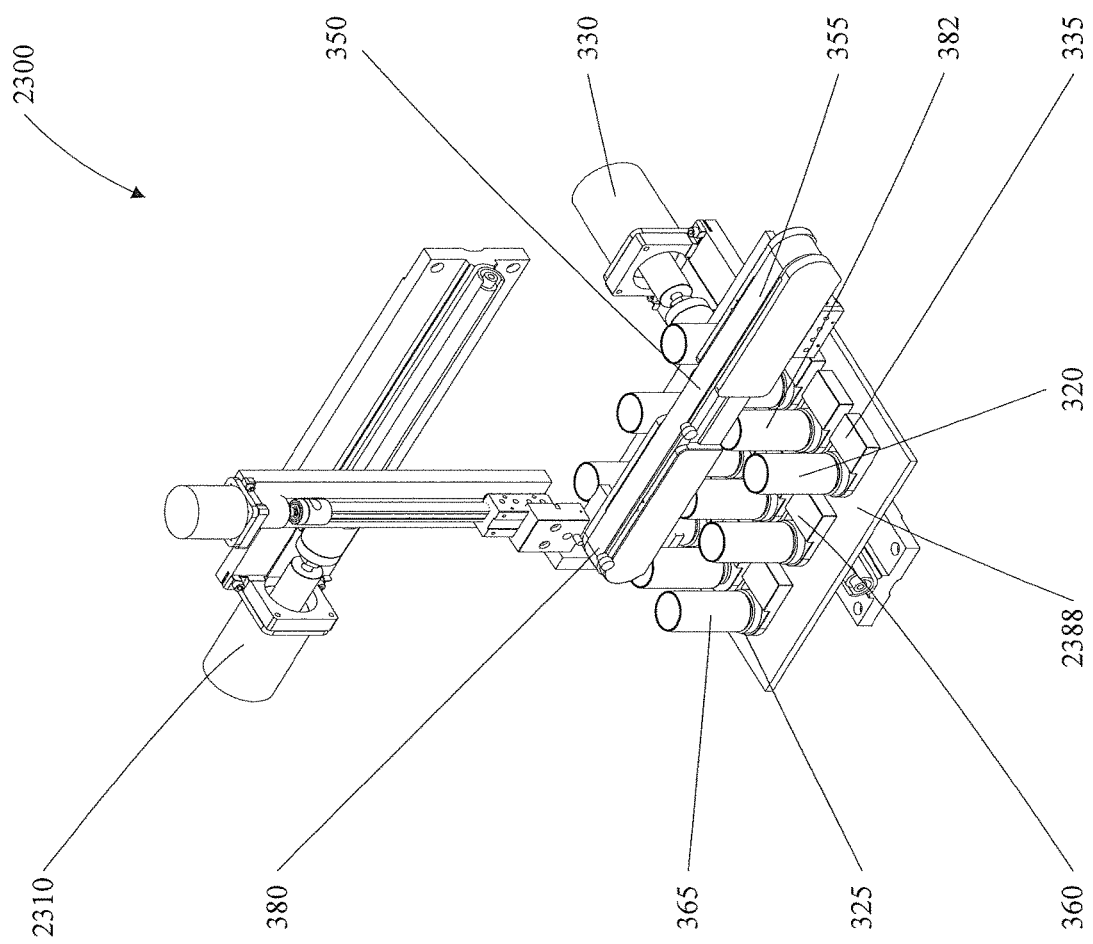
FIG. 23 is a perspective view of an exemplary sub-assembly of the dispensing unit as shown in FIG. 2.

FIG. 23 is a perspective view of an exemplary sub-assembly 2300 illustrating the disclosed system or dispenser. Sub-assembly 2300 is a view of inside elements of dispenser 102. Sub-assembly 2300 includes a loading station or MCLS 325, a medicine container transfer unit (MCTU) 330, and a storage device or medicine container storage nest (MCSN) 335. A medicine transfer unit (MTU) 355 may include a ramp or conveyor for transporting or otherwise conveying medicine from a first medicine discharge point (MDP) 350 to a second medicine discharge point (MDP) 380. The medicine discharge points 350 and 380 may not be fixed and may change to different positions during the dispensing process. MTU 355 may include one or more devices for measuring a weight or amount of medicine positioned thereon, as will be further described in further examples. Sub-assembly 2300 includes a weight checking station (WCS) 360, dispensed medicine container (DMC) 365. Weight checking station 360 may determine an amount of weight contained thereon. Sub-assembly 2300 includes a calibration and verification device 382 to automatically calibrate weight detecting devices. The calibration and verification device 382 may include, but is not limited to, a calibrator, and multiple calibration weights with different masses. The medicine containers are stored on the medicine container storage device 2388. The medicine container storage device may have many different forms and designs, Weight checking station 360 may have similar design as other medicine container storage nest 335 including a weight checking device 395 and attach to the medicine container storage device 2388. Weight checking station 360 may be a standalone device including a regular pharmacy scale or pharmacy balance.

The system may include and utilize one or a plurality of dispensed medicine containers 365 (DMC). For example, a first medicine container may have a final or prescribed dosage for patient to take and a second medicine container may be for system to use. Medicine transfer unit 355 (MTU), medicine transfer container 370 and/or 375 (MTC), dispensed medicine container 365 (DMC), and medicine storage containers 320 (MSC) may or may not be separated physical devices. The medicine containers may have any shape, size, and may differ from those illustrated. One device or container may have multiple functions. The Medicine Storage Container 320 (MSC) may include an original or standard container received with medicine from pharmacies, hospitals, etc., the medicine storage container may be integrated with or provided with the system, or may be a combination thereof. The medicine transfer unit 355 (MTU) may include any device that conveys medicine from one point to another point, and may have different forms and designs, may be a chute, a container of any shape and size, a plate, a conveyor, a moving surface, a robot, a sub assembly, a machine, although examples of the medicine transfer unit are shown in examples as a linear conveyor. A medicine quantity sensing unit may include visual sensors, or any monitoring device that may count or otherwise determine a quantity of medicine, and may include scales, load cells, balances, sensors, images, and other means. The medicine container transfer unit 330 (MCTU) may include any device that moves the medicine containers, and may have many different forms and designs, including a conveyor, a carousel, a robot, a walking beam, a dial table, a rotary table, a sub assembly, a machine. The medicine container storage device stores medicine containers and the devices may have many different forms and designs, including a platform, a container of any shape, a shelf, a conveyor, a carousel, a robot, a walking beam, a dial table, a rotary table, a sub assembly, and a machine. The systems herein may have multiple layers (such as additional medicine container transfer units).

In addition, in one example, containers used are original containers received from, for instance, a pharmacy with the medicine. However, the system may have its own containers and medicines are transferred from the original containers to the system containers. As such, the system may keep original containers. The disclosed system can transfer medicines back from system containers to original containers if needed, e.g., switch to a different medicine because of, for instance, any allergy to a medicine.

The disclosed system may have a cleaning device to clean the surfaces after dispensing cycle for those surfaces contacted with medicine during the disclosed dispensing processes.

Referring back to FIG. 23, medicine storage container 320, or original medicine container 390, either of which may have medicine provided from for instance a pharmacy, may be loaded into dispenser 102 from medicine container loading station 325, and medicine storage container 320 is transferred to it storage position on the medicine container storage device 2388 by medicine container transfer unit 330. Medicine storage container 320 may include medicine in the form of a pill or a capsule, as examples, and a dose of medicine for a user may include one or more of the pills or capsules. Medicine container transfer unit 330 is illustrated as having CNC (computer numerical control) machine 2310, but may instead include a conveyor, a robot, an automated machine, or any device that can move medicine storage container 320 from one position to another.

Medicine transfer unit 355 moves medicine from one position to another, accepts medicine from medicine storage container 320, and medicine transfer unit 355 also discharges medicine into medicine storage container 320 or any container when positioned at medicine discharge point 380. Medicine transfer unit 355 may have many different forms and designs, including a conveyor, a carousel, a robot, a walking beam, a dial table, a rotary table, a sub assembly, a machine.

In operation, dispenser 102 moves, via medicine container transfer unit 330, dispensed medicine container 365 to medicine discharge point 380. Medicine container transfer unit 330 then may move medicine storage container 320 to medicine discharge point 350. Medicine storage container 320 is, in one example, a medicine storage container which may have medicine that is desired to be distributed into dispensed medicine container 365. Medicine container transfer unit 330 discharges medicine storage container 320 such that at least a predetermined amount of medicine spills or otherwise pours from medicine storage container 320 onto medicine transfer unit 355, as determined by sensor or medicine weight detecting devices on the medicine transfer unit 355. When dispensed medicine container 365 is positioned at medicine discharge point 380, and when medicine has been discharged onto medicine transfer unit 355, medicine transfer unit 355 thereby conveys the discharged medicine from medicine transfer unit 355 into dispensed medicine container 365 until at least a second predetermined amount of medicine is contained in dispensed medicine container 365, as determined by weight determining device 395 and medicine container storage nest 335, which weigh and transmit weight information to for instance a controller of dispenser 102. The amount of medicine contained in dispensed medicine container 365 may also be determined by weight checking station 360. Other methods may be used to determine amount of medicine is contained in dispensed medicine container 365, e.g. sensor, and image.

Medicine is transferred from medicine transfer unit 355 into dispensed medicine container 365, and a weight of the medicine is determined via weight determining device 395 and/or weight checking station 360. If the measured weight is less than a given or desired dose, and if medicine is still on medicine transfer unit 355 (i.e., has not been fully discharged), then medicine transfer unit 355 further conveys more medicine into dispensed medicine container 365. On the other hand, if no medicine is on medicine transfer unit 355, then additional medicine is discharged to medicine transfer unit 355 from medicine storage container 320. The process of discharging from medicine storage container 320 to medicine transfer unit 355, and from medicine transfer unit 355 to dispensed medicine container 365 continues until at least a dose of medicine is contained in dispensed medicine container 365. That is, dispensed medicine container 365 may include an exact or desired dose, or may include an amount of medicine that is in excess of an exact dose.

If an exact dose is present in dispensed medicine container 365 and medicine is still on the medicine transfer unit 355, then dispenser 102 operates to convey medicine storage container 320 to second discharge point 380 via medicine container transfer unit 330 and discharge any remaining medicine on medicine transfer unit 355 back into medicine storage container 320.

On the other hand, in one example dispensed medicine container 365 may include an amount of medicine that is in excess of an exact dose and medicine is still on the medicine transfer unit 355, then dispenser 102 operates to convey medicine storage container 320 to second discharge point 380 via medicine container transfer unit 330 and discharge any remaining medicine on medicine transfer unit 355 back into medicine storage container 320. In such an example, dispensed medicine container 365 is conveyed via medicine container transfer unit 330 to first medicine discharge point 350. Medicine container transfer unit 330 discharges medicine inside dispensed medicine container 365 onto medicine transfer unit 355. Medicine container transfer unit 330 then moves dispensed medicine container 365 to second medicine discharge point 380 and operations described above are repeated. That is, medicine discharged from dispensed medicine container 365 to medicine transfer unit 355 is thereby conveyed to dispensed medicine container 365 until at least the exact dose is present in dispensed medicine container 365. And, again, if dispensed medicine container 365 includes medicine equal to the dose, then any excess medicine on medicine transfer unit 355 is returned to medicine storage container 320. On the other hand, in one example dispensed medicine container 365 may include an amount of medicine that is in excess of an exact dose. In such an example, any remaining medicine on medicine transfer unit 355 is discharged back into medicine storage container 320 and dispensed medicine container 365 is conveyed via medicine container transfer unit 330 to first medicine discharge point 350 and operations described above are repeated.

The aforementioned steps continue until a dose of medicine is contained within dispensed medicine container 365, and any additional medicine is returned to medicine storage container 320. In such fashion, dispenser 102 includes a feedback mechanism, ensuring a proper dose, and only a proper dose, is contained in dispensed medicine container 365. That is, feedback is provided in the form of a weight of pills or capsules, corresponding to a dose, measured via weight detecting device 395 and/or weight checking station 360. The feedback may also be provided in other forms, e.g. pill numbers determined by sensors, or images. Dispenser 102 is caused to operate using such feedback to ensure that a correct dose is provided in dispensed medicine container 365.

Figure 24:
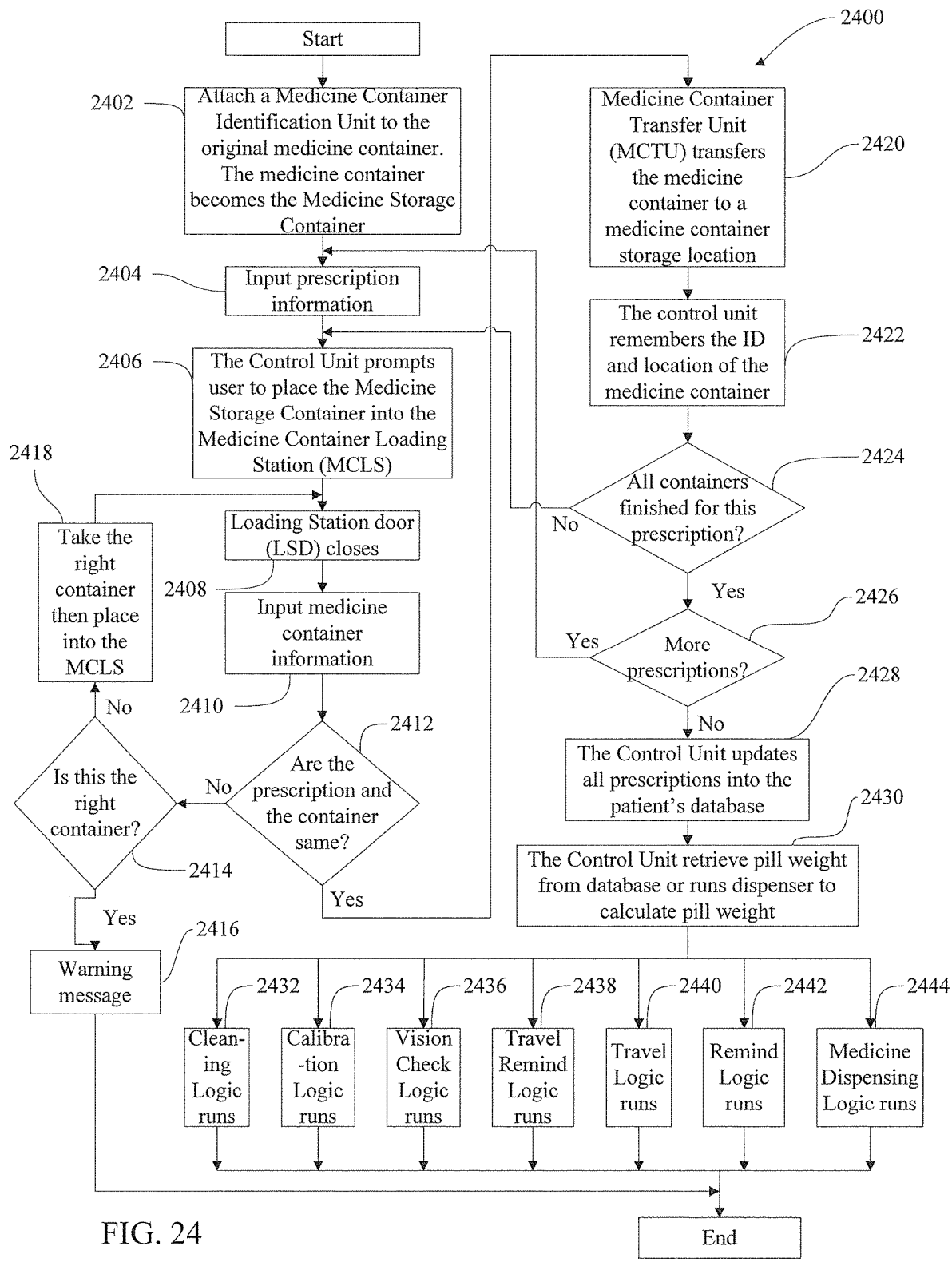
FIG. 24 is a flow diagram illustrating an exemplary process for setting up the system of FIG. 1 for operation.

Referring now to FIG. 24, a flow diagram of an exemplary process 2400 for setting up the system 100 is illustrated. Process 2400 may include operations that may be part of program 110 stored on memory 108, and/or executed by processor 106. Process 2400 may take many different forms and include multiple and/or alternate steps. While an exemplary process is shown, the exemplary steps illustrated are not intended to be limiting. Indeed, additional or alternative steps and/or implementations may be used.

Process 2400 may be the same or similar as process 600. Process 2400 may diverge from process 600 at block 2420 at which only use one medicine container transfer unit.

Figure 25:
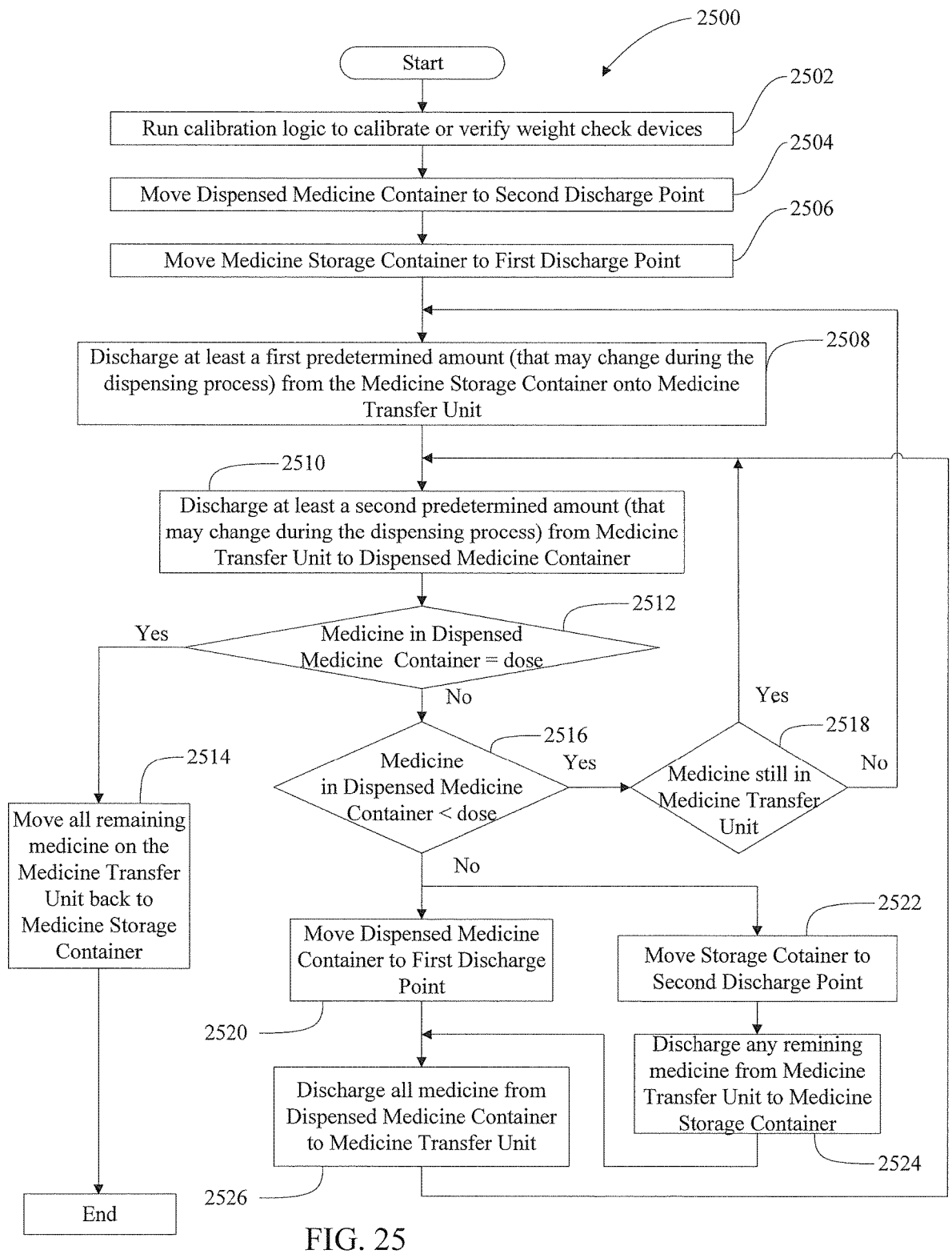
FIG. 25 is a flow diagram illustrating an exemplary process for dispensing a dose of medicine.

Referring now to FIG. 25, a flow diagram of an exemplary process 2500 is illustrated. Process 2500 may be for operating the dispensing unit 102, e.g., moving a dose (or other predetermined amount) of medicine to a dispensed medicine container. Process 2500 may include operations that may be part of program 110, stored on memory 108 or database 122, and/or executed by processor 106. Process 2500 may take many different forms and include multiple and/or alternate steps. While an exemplary process is shown, the exemplary steps illustrated are not intended to be limiting. Indeed, additional or alternative steps and/or implementations may be used. In addition, process 2500 may be applicable, in whole or in part, to each of processes 2600, 2800, 3000, and 3200 and the specific embodiments of the dispensing unit 102 incorporated therein, as described in more detail hereinafter.

At block 2502, the processor 106 may run calibration and verification logic with calibration and verification device 382 to calibrate or verify weight detecting devices.

At block 2504, the processor 106 may move, e.g., by way of the medicine container transfer unit 330, dispensed medicine container 365 from an initial position to a second discharge point 380, which, as explained above, may be located at an end of the medicine transfer unit 355 to receive the medicine.

At block 2506, processor 106, e.g., by way of medicine container transfer unit 330, may move the medicine storage container 320 from an initial position, e.g., the storage position, to a first discharge point 350, which may be stored on and received from memory 108 or database 122.

At block 2508, the processor 106 may discharge, e.g., by way of the medicine container transfer unit 330, at least a first predetermined amount of medicine from the medicine storage container 320 onto the medicine transfer unit 355. The predetermined amount may or may not be the required dosage and may change during the dispensing process. It should be appreciated that the processor 106 may discharge the medicine from the medicine storage container 320 via any known mechanism or device, which may rotate, tilt, or otherwise move the medicine storage container 320.

At block 2510, the processor 106 may discharge, e.g., by way of the medicine transfer unit 355, at least a second predetermined amount of the medicine on the medicine transfer unit 355 therefrom into the dispensed medicine container 365 positioned at the second discharge point 380. The second predetermined amount may or may not be the same as the first predetermined amount, and may change during the dispensing process.

At block 2512, the dispensing unit 102, by way of the processor 106, may determine if the medicine in the dispensed medicine container 365 is equal to the required dosage, as determined and stored in the memory 108 in process 2400. If the medicine does equal the required dosage, then process 2500 may proceed to blocks 2514. If not, then process 2500 may proceed to block 2516.

At block 2514 the processor 106 may move, e.g., via the medicine transfer unit 355, all the remaining medicine on the medicine transfer unit 355 back to the medicine storage container 320 by various rearranging of the medicine storage container 320 from and to the second medicine discharge point 380. Process 2500 may end after block 2514.

At block 2516, the dispensing unit 102, for example, by way of the processor 106, may determine if the medicine in the dispensed medicine container 365 is less than the required dosage. If it is less, then process 2500 may proceed to block 2518 at which the dispensing unit (e.g., the processor 106) may determine if there is still medicine on the medicine transfer unit 355. If there is not, process 2500 may go back to block 2508. If there is, process 2500 may go back to block 2510.

If the medicine in the dispensed medicine container 365 is not less than the required dosage, as may be determined at block 2516, process 2500 may proceed to blocks 2520 and 2522 at which the processor 106 may move the medicine storage container 320 to the second discharge point 380, and the dispensed medicine container 365 to the first discharge point 350.

At block 2524, the processor 106 may discharge any remaining medicine on the medicine transfer unit 355 into the medicine storage container 320.

At block 2526, the processor 106 may discharge medicine inside dispensed medicine container 365 onto medicine transfer unit 355.

After block 2526, process 2500 may go back to block 2510 and operations described above are repeated.

Process 2500 may be iterated until the medicine in the dispensed medicine container 365 equals the required dosage.

As described in more detail with respect to processes 2600, 2800, 3000, and 3200, the processor 106 may communicate with, i.e., send commands to, receive data from, and the like, to various components of the dispensing unit 102 and/or system 500 to perform the different steps of process 2500. In addition or alternatively, the various components may communicate directly with each other.

Figure 26:
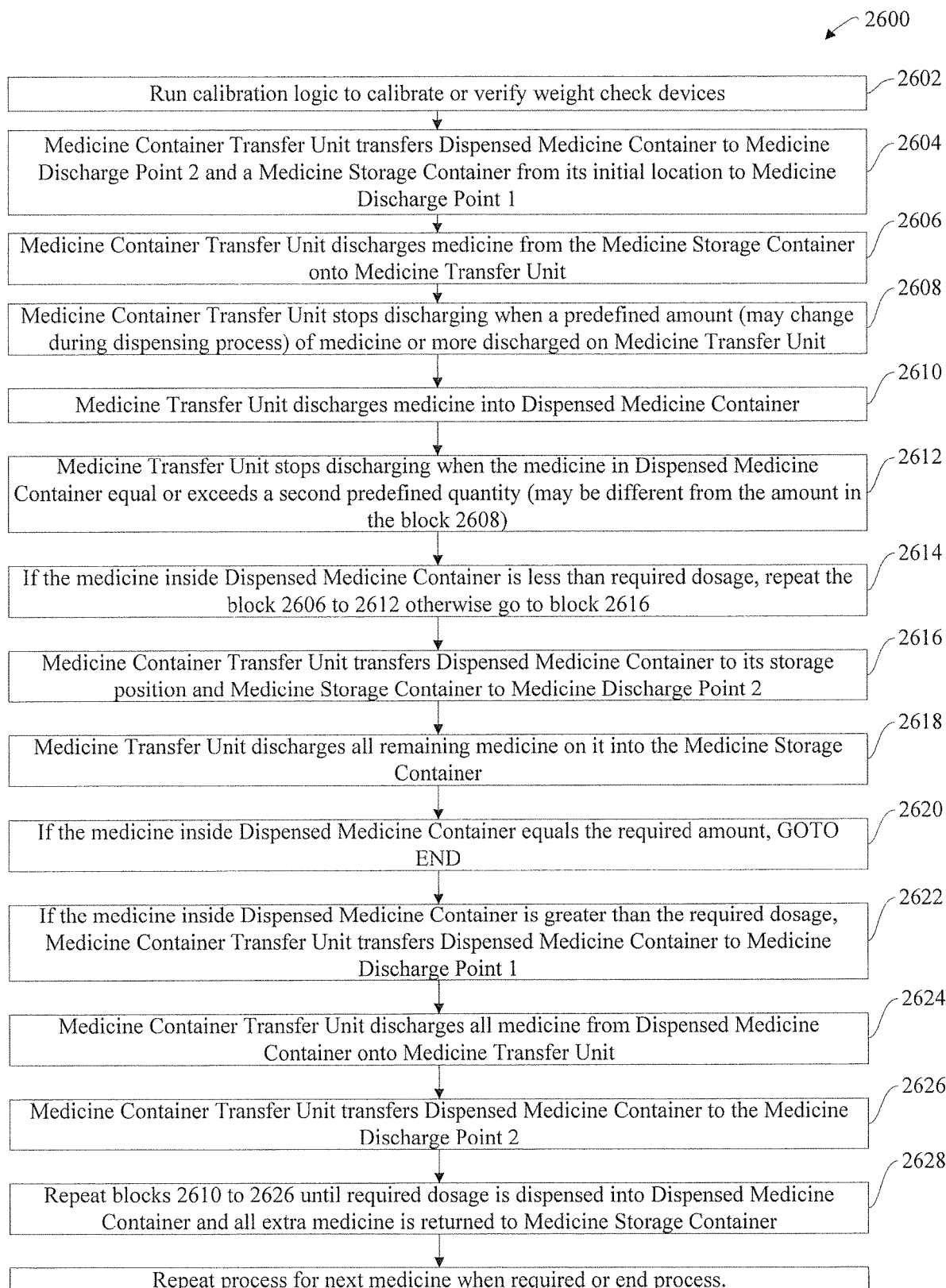
FIG. 26 is a flow diagram illustrating an exemplary process for dispensing a dose of medicine via the exemplary sub-assembly of FIG. 23.

Referring now to FIG. 26, a flow diagram of another exemplary process 2600 for operating the dispensing unit 102 is illustrated, which may incorporate the sub-assembly 2300. Process 2600 may include operations that may be part of program 110, stored on memory 108, and/or executed by processor 106. Process 2600 may take many different forms and include multiple and/or alternate steps. While an exemplary process is shown, the exemplary steps illustrated are not intended to be limiting. Indeed, additional or alternative steps and/or implementations may be used.

Process 2600 may begin at step 2602 at which the processor 106 may run calibration and verification logic with calibration and verification device 382 to calibrate or verify weight detecting devices.

At block 2604, the medicine container transfer unit 330 may transfer a dispensed medicine container 365 to second discharge point 380 and a medicine storage container 320 from its initial location to first discharge point 350.

At block 2606, the processor 106 may discharge medicine from the medicine storage container 320 onto the medicine transfer unit 355. This may be achieved by rotating the medicine storage container 320, which may be steady or intermittent, and operating the end of arm tool 1125. It should be appreciated that other ways to discharge the medicine from the medicine storage container 320 onto the medicine transfer unit 355 are contemplated.

At block 2608, sensor and/or scale and/or other medicine detecting devices detect quantity of medicine discharged on the medicine transfer unit 355.

At block 2610, the processor 106 may stop discharging when it receives a signal from the medicine transfer unit 355 or other medicine detecting devices that detects at least a predefined amount of medicine discharged on the medicine transfer unit 355, which may or may not be the required dosage. For example, the medicine transfer unit 355 may include one or more sensors that detect weight, area, volume, or any other characteristic by which an amount of medicine on the medicine transfer unit 355 may be determined. The medicine transfer unit 355 may then communicate, e.g., send a signal, directly to the medicine container transfer unit 330 to stop discharging, or indirectly by sending a signal to the processor 106 that the predefined amount of medicine has been detected, the processor 106 in turn to stop discharging.

At block 2612, the medicine transfer unit 355 may then begin discharging the medicine on it into the dispensed medicine container 365.

At block 2614, the processor 106 may determine if the medicine inside the dispensed medicine container 365 is less than the required dosage. In one exemplary approach, this may be determined by measuring the weight of the medicine in the dispensed medicine container 365 by weight checking station 360 and/or by the scale 395 on which the dispensed medicine container 365 may be disposed. The weight checking device 395 and/or weight checking station 360 may then transmit data representing the measured weight to the processor 106, which may then compare the measured weight with a weight corresponding to the medicine in the required dosage, which may be stored locally on the memory 108 and/or remotely at any one of the databases 510-516.

If the medicine inside the dispensed medicine container 365 is not less than the required dosage, then process 2600 may proceed to block 2616. If it is less and there is no medicine left on the medicine transfer unit 355, then process 2600 may repeat blocks 2606 to 2612 until the amount of medicine inside the dispensed medicine container 365 is not less than the required dosage. Then process 2500 may proceed to block 2616.

At block 2616, the medicine transfer unit 355 may stop discharging the medicine when the medicine in the dispensed medicine container 365 equals or exceeds a predefined quantity (which may be different from the amount in the block 2610).

At block 2618, the medicine container transfer unit 330 may transfer the dispensed medicine container 365 to its storage position and the medicine storage container 320 to the second medicine discharge point 380.

At block 2620, the medicine transfer unit 355 may discharge all the remaining medicine on it back into the medicine storage container 320.

At block 2622, if the medicine in the dispensed medicine container 365 is equal to the required dosage, process 2600 may end after this step.

At block 2624, if the medicine inside dispensed medicine container 365 is greater than the required dosage, medicine container transfer unit 330 transfers dispensed medicine container 365 to the first medicine discharge point 350.

At block 2626, the processor 106 may discharge medicine from the dispensed medicine container 365 onto the medicine transfer unit 355.

At block 2628, medicine detecting devices monitor medicine discharged on the medicine transfer unit 355 and left in the dispensed medicine container 365.

At block 2630, if medicine left in the dispensed medicine container 365 is less than the required dosage, go to block 2634.

At block 2632, if medicine left in the dispensed medicine container 365 equals to the required dosage, return all medicine on the medicine transfer unit 355 to the medicine storage container 320. The process may end.

At block 2634, the medicine container transfer unit 330 may transfer the dispensed medicine container 365 to the second medicine discharge point 380.

At block 2636, repeat blocks 2612 to 2634 until required dosage is dispensed into the dispensed medicine container 365 and all extra medicine is returned to the medicine storage container 320.

Process 2600 may be repeated for the next medicine when required.

In general, process 2600 may be a closed feedback loop process with stable and fast convergent iterations. In addition, the processor 106 may communicate with, i.e., send commands to, receive data from, and the like, to various components of the dispensing unit 102 and/or system 500 to perform process 2600.

Figure 27A:
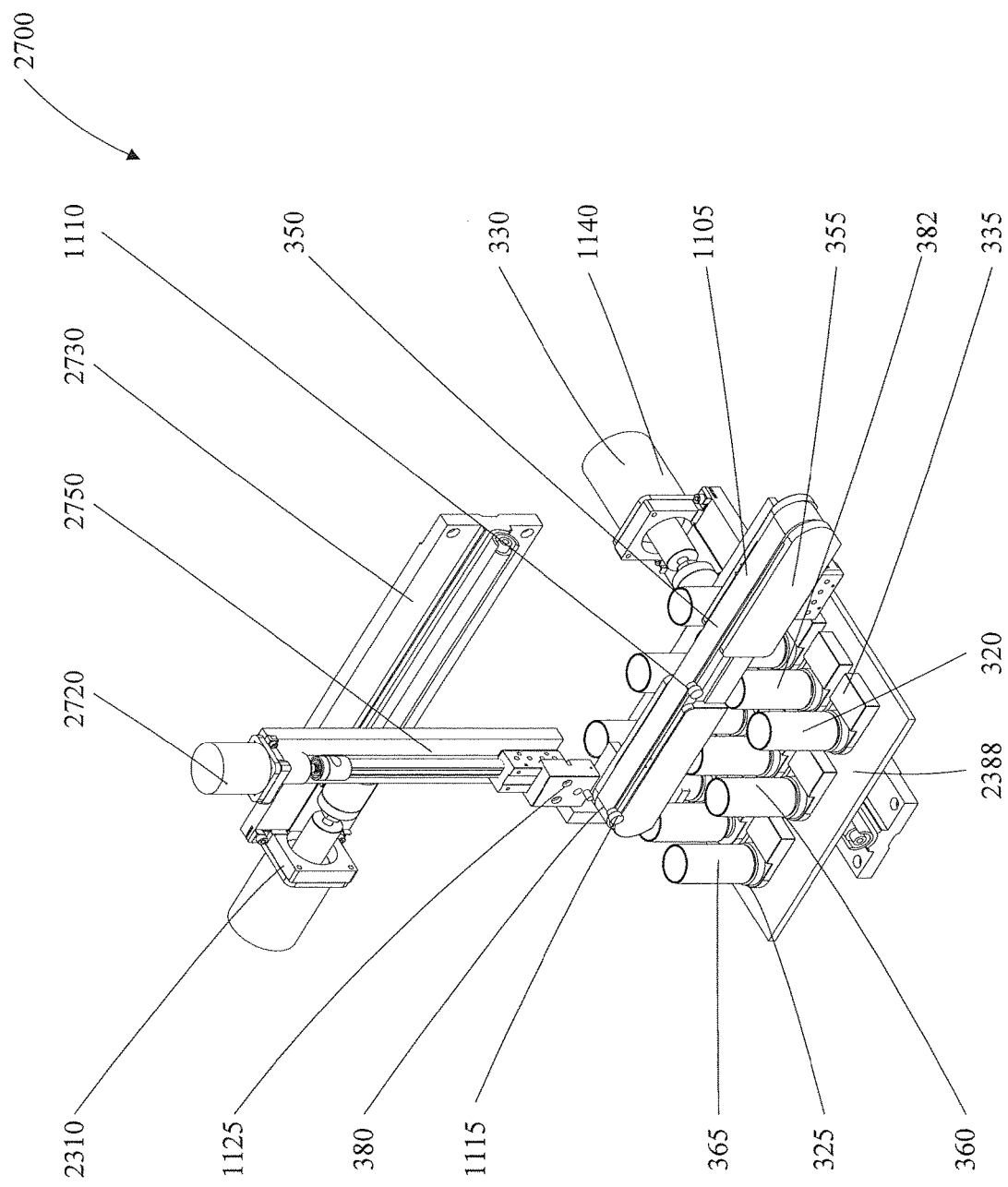
FIG. 27A is a perspective view of a sub-assembly according to another exemplary approach.
Figure 27B:
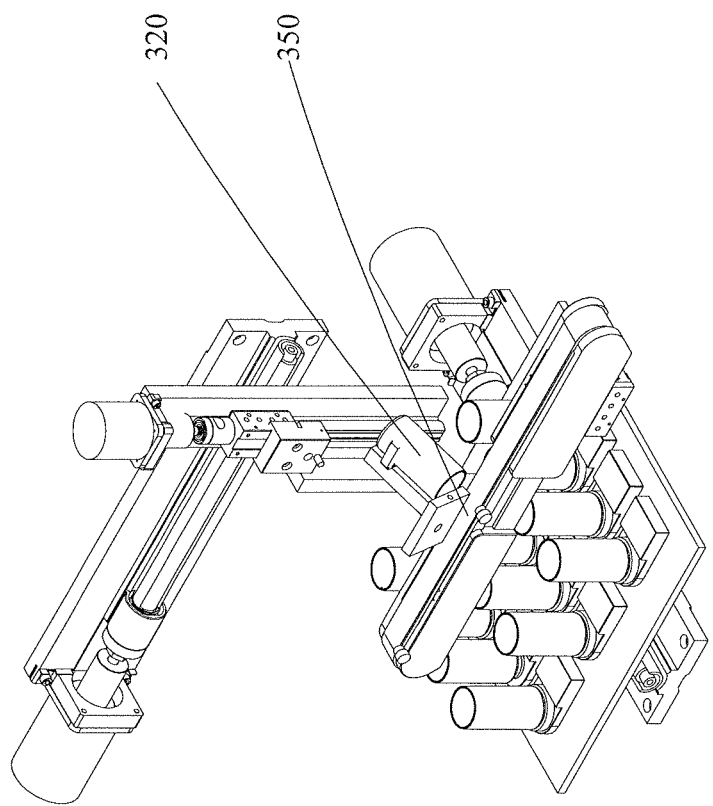
FIG. 27B illustrates the exemplary system of FIG. 27A during operation.
Figure 27C:
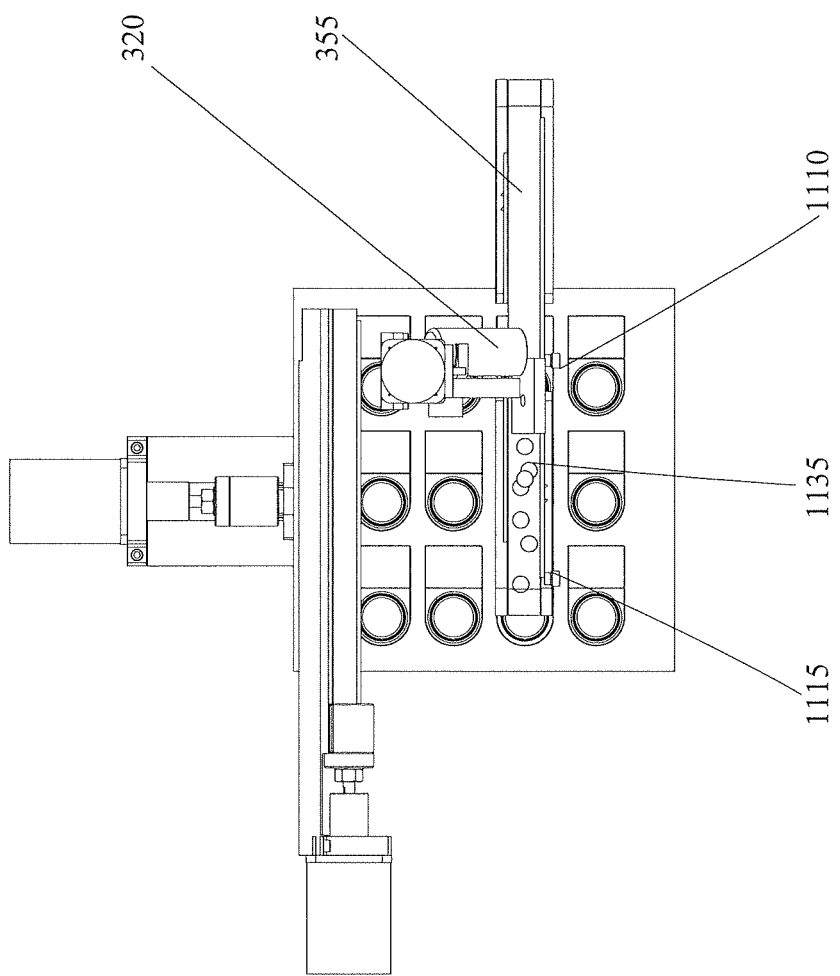
FIG. 27C illustrates a top view of the exemplary system of FIG. 27B.

FIG. 27A illustrates an exemplary sub-assembly 2700 of the disclosed system. FIG. 27B illustrates the exemplary system of FIG. 27A during operation. FIG. 27C illustrates a top view of the exemplary system of FIGS. 27A and 27B. FIG. 27A illustrates the disclosed dispenser having a conveyor 1105, and a CNC machine 2720, In this example medicine container transfer unit 330 includes CNC machine 2720 that includes X axis 2730, Y axis 2740, Z axis 2750, and an end of arm tool (EOAT) 1125. Medicine transfer unit 355 may include a conveyor 1105 and sensors 1110 and 1115. FIG. 27B is a view of sub-assembly as shown in FIG. 27A, showing medicine storage container 320 transferred to first medicine discharging point 350 by medicine container transfer unit 330 to discharge medicine from medicine storage container 320 onto conveyor 1105. Sensors 1110 and 1115 monitor medicine positioned on medicine transfer unit 355 and more specifically on conveyor 1105.

FIG. 27A illustrates an exemplary sub-assembly 2700 illustrating the disclosed system or dispenser. Sub-assembly 2700 is a view of inside elements of dispenser 102 and includes CNC machine 2720. Sub-assembly 2700 includes loading station or medicine container loading station 325, medicine container transfer unit 330, and medicine container storage nest 335. Medicine transfer unit 355 includes, in the illustrated example, conveyor 1105 for transporting or otherwise conveying medicine from first medicine discharge point 350 to second medicine discharge point 380, and may include sensors 1110 and 1115. The medicine discharge points 350 and 380 may not be fixed and may change to different positions during the dispensing process. Sub-assembly 2700 includes weight checking station 360, dispensed medicine container 365, and a calibration and verification device 382 to automatically calibrate weight detecting devices. The medicine containers are stored on the medicine container storage device 2388. The medicine container storage device may have many different forms and designs, Weight checking station 360 may have similar design as other medicine container storage nest 335 including a weight checking device 395 and attach to the medicine container storage device 2388. Weight checking station 360 may also be a standalone device including a regular pharmacy scale or pharmacy balance.

Referring to FIGS. 27A-C, FIG. 27A is an illustration of medicine storage container 320 as positioned at its storage position, and FIG. 27B the exemplary system of FIG. 27A during operation. Medicine storage container 320 may include original medicine container 390, medicine container identification unit 385, weight detecting device 395, and medicine container storage nest 335. Weight detecting device 395 and medicine container storage nest 335 may be integrated together. Weight detecting device 395 may be a scale, a load cell, or other device for measuring weight, according to the disclosure. Weight detecting device 395 and medicine container storage nest 335 are positioned about medicine container storage device 2388 at each of the illustrated locations. Medicine container identification unit 385 may include identification information particular to a given medicine, and may also identify an amount of medicine that may constitute a single patient dose particular to a given user of dispenser 102.

Referring still to FIG. 27A, medicine storage container 320 may be loaded into dispenser 102 from medicine container loading station 325, and medicine storage container 320 is transferred to its storage position by medicine container transfer unit 330. Medicine storage container 320 may include medicine in the form of a pill or a capsule, as examples, and a dose of medicine for a user may include one or more of the pills or capsules. Medicine container transfer unit 330 is illustrated as having a CNC machine 2720, but may instead include a conveyor, a robot, or any device that can move medicine storage container 320 from one position to another, and discharge medicine from medicine storage container 320. The Y axis 2740 is illustrated as a sub system of the CNC machine 2720, but may be a different machine working with the CNC machine 2720 and may have many different forms and designs, including a platform, a container of any shape, a shelf, a conveyor, a carousel, a robot, a walking beam, a dial table, a rotary table, a sub assembly, and any device that can move medicine storage container 320.

Medicine transfer unit 355 moves medicine from one position to another, accepts medicine from medicine storage container 320, and medicine transfer unit 355 also discharges medicine into medicine storage container 320 or any container when positioned at medicine discharge point 380. Medicine transfer unit 355 may have a linear moving surface such as a walking beam, a conveyor, a vibrating feeder, or a rotating surface such as a rotating disc or other shape.

In operation, as shown in FIGS. 27A and 27B, dispenser 102 moves, via the medicine container transfer unit 330, dispensed medicine container 365 to second medicine discharge point 380 and medicine storage container 320 to first medicine discharge point 350. Medicine storage container 320 is, in one example, a medicine storage container which may have an amount of medicine that is in excess of a dose, or an amount of medicine that is desired to be distributed into dispensed medicine container 365. Medicine container transfer unit 330 turns medicine storage container 320 such that a predetermined amount of medicine spills or otherwise pours from medicine storage container 320 onto medicine transfer unit 355, as determined by sensor or medicine detecting device on the medicine transfer unit 355. When dispensed medicine container 365 is positioned at medicine discharge point 380, and when medicine has been discharged onto medicine transfer unit 355, medicine transfer unit 355 thereby conveys the discharged medicine from medicine transfer unit 355 into dispensed medicine container 365 until at least a second predetermined amount of medicine is contained in dispensed medicine container 365, as determined by weight checking station 360 and/or by weight detecting device 395 and medicine container storage nest 335, which weigh and transmit weight information to for instance a controller of dispenser 102.

Medicine transfer unit 355 includes conveyor 1105, and sensors 1110 and 1115, which monitor medicine positioned on medicine transfer unit 355 and on conveyor 1105. Sensors 1110, 1115 may be optical sensors that are coupled, electrically or optically as examples, to processor 106. As such, processor 106 monitors an amount of medicine positioned on medicine transfer unit 355 via sensors 1110, 1115.

FIG. 27C illustrates a top view of the exemplary system of FIGS. 27A and 27B, and shows medicine storage container 320 turned such that at least a predetermined amount of medicine spills or otherwise pours from medicine storage container 320 onto medicine transfer unit 355. Sensors 1110 and 1115 detect the presence of pills or capsules 1135 as they pass thereby via medicine transfer unit 355 to second medicine discharge point 380.

Medicine is transferred from medicine transfer unit 355 into dispensed medicine container 365, and a weight of the medicine is determined via weight detecting device 395 and/or weight checking station 360. If the measured weight is less than a given or desired dose, and if medicine is still on medicine transfer unit 355 (i.e., has not been fully discharged), then medicine transfer unit 355 further conveys more medicine into dispensed medicine container 365. On the other hand, if no medicine is on medicine transfer unit 355, then additional medicine is discharged to medicine transfer unit 355 from medicine storage container 320. The process of discharging from medicine storage container 320 to medicine transfer unit 355, and from medicine transfer unit 355 to dispensed medicine container 365 continues until at least a dose of medicine is contained in dispensed medicine container 365. That is, dispensed medicine container 365 may include an exact or desired dose, or may include an amount of medicine that is in excess of an exact dose.

If an exact dose is present in dispensed medicine container 365 and medicine is still on the medicine transfer unit 355, then dispenser 102 operates to convey medicine storage container 320 to second discharge point 380 via medicine container transfer unit 330 and discharge any remaining medicine on medicine transfer unit 355 back into medicine storage container 320.

On the other hand, in one example dispensed medicine container 365 may include an amount of medicine that is in excess of an exact dose and medicine is still on the medicine transfer unit 355, then dispenser 102 operates to convey medicine storage container 320 to second discharge point 380 and discharge any remaining medicine on medicine transfer unit 355 back into medicine storage container 320. In such an example, dispensed medicine container 365 is thereby conveyed to first medicine discharge point 350 and medicine container transfer unit 330 discharges medicine from dispensed medicine container 365 onto medicine transfer unit 355. Medicine container transfer unit 330 moves dispensed medicine container 365 to second discharge point 380 and operations described above are repeated. That is, medicine discharged from dispensed medicine container 365 to medicine transfer unit 355 is thereby conveyed to dispensed medicine container 365 until at least a dose of medicine is contained in dispensed medicine container 365. That is, dispensed medicine container 365 may include an exact or desired dose, or may include an amount of medicine that is in excess of an exact dose. And, again, if dispensed medicine container 365 includes medicine equal to the dose, then the medicine in any excess medicine on medicine transfer unit 355 is returned to medicine storage container 320. If dispensed medicine container 365 includes an amount of medicine that is in excess of an exact dose, then operations described above are repeated.

The aforementioned steps continue until a dose of medicine is contained within dispensed medicine container 365, and any additional medicine is returned to medicine storage container 320. In such fashion, dispenser 102 includes a feedback mechanism, ensuring a proper dose, and only a proper dose, is contained in dispensed medicine container 365. That is, feedback is provided in the form of a weight of pills or capsules, corresponding to a dose, measured via weight detecting device 395 and/or weight checking station 360. Dispenser 102 is caused to operate using such feedback to ensure that a correct dose is provided in dispensed medicine container 365.

Figure 28:
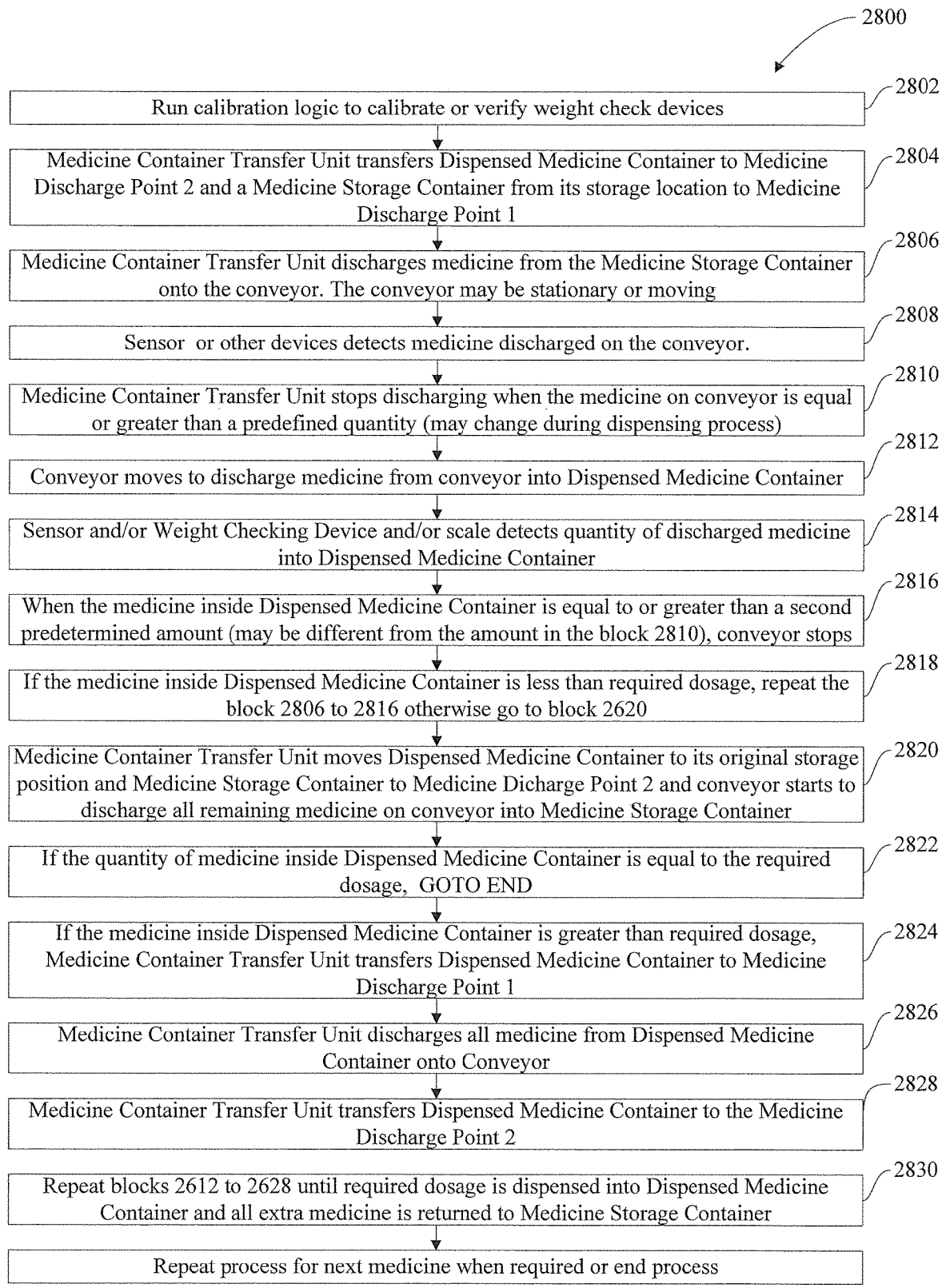
FIG. 28 is a flow diagram illustrating an exemplary process for dispensing a dose of medicine via the exemplary sub-assembly of FIGS. 27A-27C.

Referring now to FIG. 28, a flow diagram of another exemplary process 2800 for operating the dispensing unit 102, which may incorporate the sub-assembly 2700, is illustrated. Process 2800 may include operations that may be part of program 110, stored on memory 108, and/or executed by processor 106. Process 2800 may take many different forms and include multiple and/or alternate steps. While an exemplary process is shown, the exemplary steps illustrated are not intended to be limiting. Indeed, additional or alternative steps and/or implementations may be used. In addition, for purposes of process 2800, the medicine container transfer unit 330 is referred to as CNC machine. However, it should be appreciated that any medicine container transfer unit 330, for performing the respective step(s) is contemplated, and that the use of the terms CNC machine and robot are not intended to be limiting.

Process 2800 may begin at block 2802 at which the processor 106 may run calibration and verification logic with calibration and verification device 382 to calibrate or verify weight detecting devices.

At block 2804, the medicine container transfer unit 330 may transfer a dispensed medicine container 365 to the second medicine discharge point 380 and a medicine storage container from its storage location to first discharge point 350.

At block 2806, medicine container transfer unit 330 may discharge medicine from the medicine storage container 320 onto the conveyor 1105, which may be stationary or moving.

At block 2808, sensor 1110 or other devices may detect medicine discharged on the conveyor 1105.

At block 2810, medicine container transfer unit 330 may stop discharging medicine storage container 320 when medicine on the conveyor 1105 is equal to or greater than a predefined quantity. This may be determined based on feedback from sensor 1110, 1105 or other devices. The predefined quantity may change during the dispensing process.

At block 2812, the conveyor 1105 may move to discharge medicine from conveyor 1105 into the dispensed medicine container 365.

At block 2814, a sensor 1115 and/or scale 395 under the dispensed medicine container 365 and/or weight checking station 360 may detect a quantity of medicine discharged into the dispensed medicine container 365.

At block 2816, the conveyor 1105 may stop based on feedback from the sensor 1115 and/or scale 395 and/or weight checking station 360 that the quantity of medicine inside the dispensed medicine container 365 is equal to or greater than the required dosage.

At block 2818, if the medicine inside the dispensed medicine container 365 is less than required dosage and there is no medicine on the conveyor, repeats the blocks 2806 to 2816 otherwise go to block 2620.

At block 2820, medicine container transfer unit 330 may transfer the dispensed medicine container 365 to its storage location and medicine storage container 320 to the second medicine discharge point 380. Conveyor 1105 may begin to discharge all remaining medicine on conveyor 1105 into the medicine storage container 320.

At block 2822, the processor 106 may determine if the medicine inside the dispensed medicine container 365 is equal to the required dosage. If so, process 2800 may then end.

At block 2824, the processor 106 may determine if the medicine inside the dispensed medicine container 365 is greater than the required dosage. If so, medicine container transfer unit 330 may transfer the dispensed medicine container 365 to the first medicine discharge point 350.

At block 2826, medicine container transfer unit 330 may discharge medicine from the dispensed medicine container 365 onto the conveyor 1105.

At block 2828, medicine container transfer unit 330 may transfer the dispensed medicine container 365 to the second medicine discharge point 380.

At block 2830, blocks 2810 through 2826 may then be repeated until the required dosage is dispensed into the dispensed medicine container 365, and all extra medicine, is returned to the medicine storage container 320.

Process 2800 may be repeated for the next medicine when required.

In embodiments, weight checking station 360 and/or scale(s) 395, for example, in each weighing station or storage nests associated with each container, may check quantity of medicine inside each container involved in process 2800, e.g., the medicine storage container 320, and the dispensed medicine container 365.

In general, process 2800 may be a closed feedback loop process with stable and fast convergent iterations. In addition, the processor 106 may communicate with, i.e., send commands to, receive data from, and the like, to various components of the dispensing unit 102 and/or system 500 to perform process 2800.

Figure 29A:
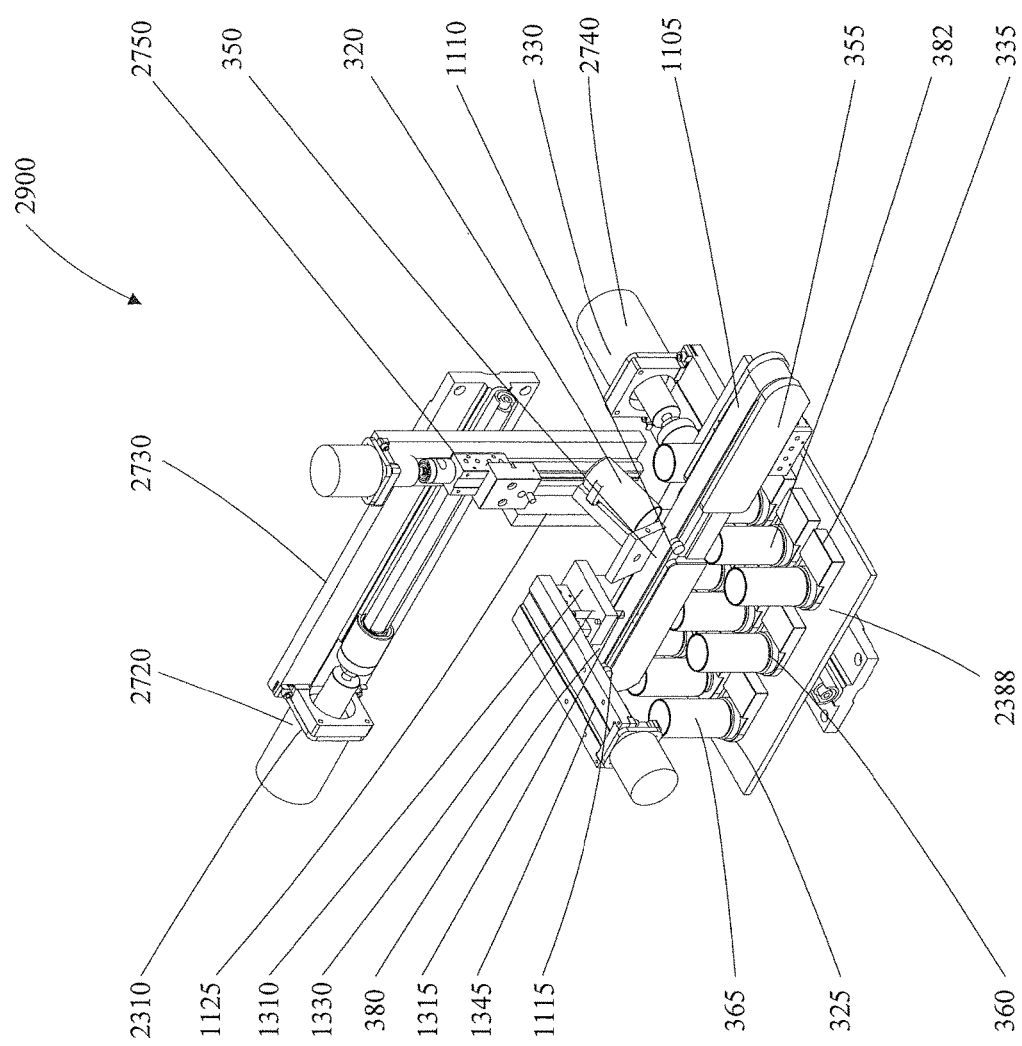
FIG. 29A is a perspective view of a sub-assembly according to another exemplary approach.

FIG. 29A illustrates an exemplary sub-assembly 2900 of the disclosed system. Sub-assembly 2900 includes medicine container transfer unit 330 having CNC machine 2720 with an end of arm tool 1125. Medicine transfer unit 355 includes a robot or conveyor 1105, sensors 1110 and 1115, robot 1345 having an end of arm tool 1310, a sensor 1330, and a vacuum head 1315. Medicine container transfer unit 330 and robot 1345 may be two different robots, or two different parts of the same one robot.

Figure 29B:
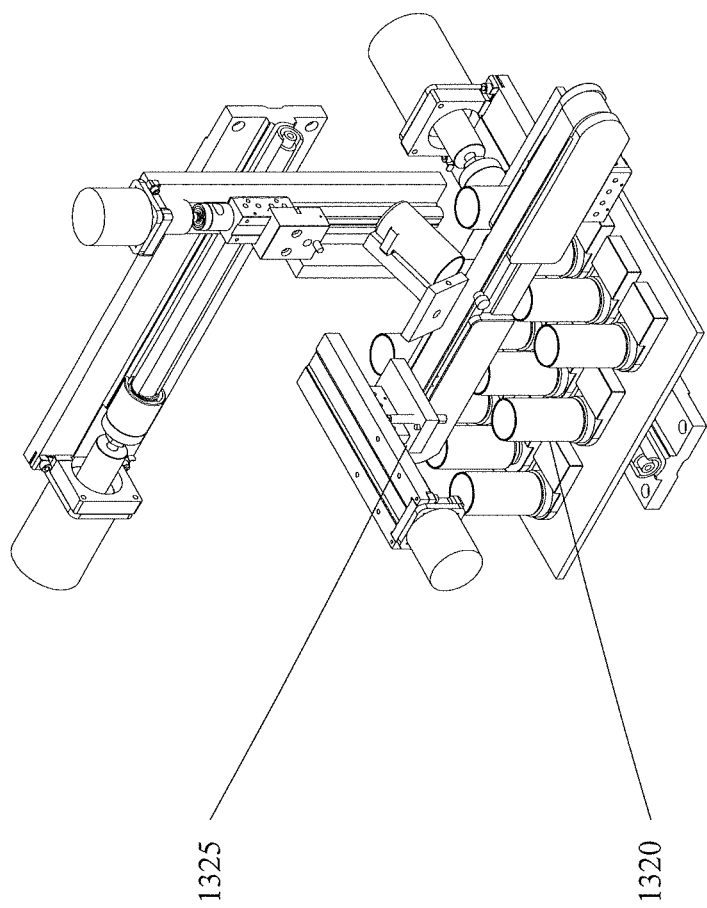
FIG. 29B illustrates the exemplary system of FIG. 29A during operation.

FIG. 29B is a view of the example of FIG. 29A, showing end of arm tool 1310 at medicine discharge position 1325 to discharge medicine into medicine storage container at discharge position 1320. The end of arm tool 1310 may also discharge medicine into medicine storage container at discharge position 380 (not shown). The end of arm tool 1310 may also pick up medicine from medicine containers at discharge position 1320 or 380 and discharge onto medicine transfer unit 355.

Sub-assembly 2900 is a view of inside elements of dispenser 102 and includes medicine container transfer unit 330. Sub-assembly 2900 includes loading station or medicine container loading station 325, medicine container transfer unit 330, and medicine container storage nest 335. Medicine transfer unit 355 includes, in the illustrated example, robot 1345 and conveyor 1105 for transporting or otherwise conveying medicine from first discharge point 350 to second medicine discharge point 380, and third medicine discharge point 1320, and may include sensors 1110 and 1115. Sub-assembly 2900 includes weight checking station 360, a calibration and verification device 382 to automatically calibrate weight detecting devices, and dispensed medicine container 365. Medicine storage container 320 is positioned on medicine container storage device 2388. Weight checking station 360 may have similar design as other medicine container storage nest 335 including a weight checking device 395 and attach to the medicine container storage device 2388. Weight checking station 360 may be a standalone device including a regular pharmacy scale or pharmacy balance.

FIG. 29A is an illustration of exemplary sub-system 2900, and FIG. 29B of the exemplary system of FIG. 29A shows end of arm tool 1310 at medicine discharging position. Medicine storage container 320 may include original medicine container 390, medicine container identification unit 385, weight detecting device 395, and medicine container storage nest 335. Weight detecting device 395 and medicine container storage nest 335 may be integrated together. Weight detecting device 395 and medicine container storage nest 335 may also be part of container storage device 2388. Weight detecting device 395 may be a scale, a load cell, a balance, or other device for measuring weight, according to the disclosure. Weight detecting device 395 and medicine container storage nest 335 are positioned on medicine container storage device 2388 at each of the illustrated locations. Medicine container identification unit 385 may include identification information particular to a given medicine, and may also identify an amount of medicine that may constitute a single patient dose particular to a given user of dispenser 102.

Referring still to FIG. 29A, medicine storage container 320 may be loaded into dispenser 102 from medicine container loading station 325, and medicine storage container 320 is transferred to its storage position on medicine container storage device 2388 by medicine container transfer unit 330. Medicine storage container 320 may include medicine in the form of a pill or a capsule, as examples, and a dose of medicine for a user may include one or more of the pills or capsules. Medicine container transfer unit 330 is illustrated as having CNC machine 2720 that includes X axis 2730, Y axis 2740, Z axis 2750, and an end of arm tool (EOAT) 1125, but may instead include a conveyor, a robot, or any device that can move medicine storage container 320 from one position to another, and discharge medicine from medicine storage container 320.

Medicine transfer unit 355 moves medicine from one position to another, accepts medicine from medicine storage container 320, and medicine transfer unit 355 also discharges medicine into medicine storage container 320 or any container when positioned at medicine discharge point 380 or 1320. Medicine transfer unit 355 may have a linear moving surface such as a walking beam, a conveyor, a vibrating feeder, or a rotating surface such as a rotating disc or other shape, and includes in the illustrated example conveyor 1105 and robot 1345.

In operation, as shown in FIGS. 29A and 29B, dispenser 102 moves, via medicine container transfer unit 330, dispensed medicine container 365 to second medicine discharge point 380 and medicine storage container 320 to first medicine discharge point 350. Medicine storage container 320 is, in one example, a medicine storage container which may have an amount of medicine that is in excess of a dose, or an amount of medicine that is desired to be distributed into dispensed medicine container 365. Medicine container transfer unit 330 turns medicine storage container 320 such that a predetermined amount of medicine spills or otherwise pours from medicine storage container 320 onto medicine transfer unit 355, as determined by sensor or medicine weight detecting device. When dispensed medicine container 365 is positioned at medicine discharge point 380, and when medicine has been discharged onto medicine transfer unit 355, medicine transfer unit 355 thereby conveys the discharged medicine from medicine transfer unit 355 into dispensed medicine container 365 until at least a second predetermined amount of medicine is contained in dispensed medicine container 365, as determined by weight checking station 360 and/or weight detecting device 395 and medicine container storage nest 335, which weigh and transmit weight information to for instance a controller of dispenser 102.

Medicine transfer unit 355 includes robot 1345 and conveyor 1105, and sensors 1110 and 1115, which monitor medicine positioned on medicine transfer unit 355 and on conveyor 1105. Sensors 1110, 1115 may be optical sensors that are coupled, electrically or optically as examples, to processor 106. As such, processor 106 monitors an amount of medicine positioned on medicine transfer unit 355 via sensors 1110, 1115. Sensors 1110 and 1115 detect the presence of pills or capsules as they pass thereby via medicine transfer unit 355 to second medicine discharge point 380. In addition, robot 1345 includes end of arm tool 1310 having vacuum head 1315 that may attach via a vacuum, controlled by processor 106, to individual pills or capsules passing along medicine transfer unit 355. Accordingly, in this example, pills or capsules may be not only conveyed by conveyor 1105 to dispensed medicine container 365 when positioned at medicine discharge point 380, but also conveyed by robot 1345 to dispensed medicine container 365 when positioned at medicine discharge point 380. Pills or capsules may also be conveyed by robot 1345 to dispensed medicine container 365 positioned at position 1320. Pills or capsules may also be conveyed by robot 1345 from dispensed medicine container 365 at discharge point 380 or 1320 back to the medicine transfer unit 355. Both methods may be used concurrently or separately. Thus, movement of pills or capsules may be improved by having an ability to move pills or capsules to and/or from two locations simultaneously.

Medicine is transferred from medicine transfer unit 355 into dispensed medicine container 365, and a weight of the medicine is determined via weight detecting device 395 and/or weight checking station 360. If the measured weight is less than a predetermined amount, and if medicine is still on medicine transfer unit 355 (i.e., has not been fully discharged), then medicine transfer unit 355 further conveys more medicine into dispensed medicine container 365. On the other hand, if no medicine is on medicine transfer unit 355, then additional medicine is discharged to medicine transfer unit 355 from medicine storage container 320. The process of discharging from medicine storage container 320 to medicine transfer unit 355, and from medicine transfer unit 355 to dispensed medicine container 365 continues until at least a predetermined amount of medicine is contained in dispensed medicine container 365. That is, dispensed medicine container 365 may include an exact or desired dose, or may include an amount of medicine that is in excess of an exact dose.

If an exact dose is present in dispensed medicine container 365 and medicine is still on the medicine transfer unit 355, then dispenser 102 operates to convey medicine storage container 320 to second discharge point 380 via medicine container transfer unit 330 and discharge any remaining medicine on medicine transfer unit 355 back into medicine storage container 320.

On the other hand, in one example dispensed medicine container 365 may include an amount of medicine that is in excess of an exact dose and medicine is still on the medicine transfer unit 355, then dispenser 102 operates to convey medicine storage container 320 to second discharge point 380 via medicine container transfer unit 330 and discharge any remaining medicine on medicine transfer unit 355 back into medicine storage container 320. In such an example, dispensed medicine container 365 is thereby conveyed to first medicine discharge point 350 and medicine container transfer unit 330 discharges medicine from dispensed medicine container 365 onto medicine transfer unit 355. Then medicine container transfer unit 330 may move medicine container 365 to second discharge point 380 and operations described above are repeated. That is, medicine discharged from dispensed medicine container 365 to medicine transfer unit 355 is thereby conveyed to dispensed medicine container 365 until at least the exact dose is present in dispensed medicine container 365. And, again, if dispensed medicine container 365 includes medicine equal to the dose, then any excess medicine on medicine transfer unit 355 is returned to medicine storage container 320. On the other hand, in one example dispensed medicine container 365 may include an amount of medicine that is in excess of an exact dose. In such an example, operations described above are repeated. That is, medicine container transfer unit 330 discharges medicine from dispensed medicine container 365 onto medicine transfer unit 355 and medicine transfer unit 355 discharges medicine into dispensed medicine container 365.

The aforementioned steps continue until a dose of medicine is contained within dispensed medicine container 365, and any additional medicine is returned to medicine storage container 320. In such fashion, dispenser 102 includes a feedback mechanism, ensuring a proper dose, and only a proper dose, is contained in dispensed medicine container 365. That is, feedback is provided in the form of a weight of pills or capsules, corresponding to a dose, measured via weight detecting device 395 and/or weight checking station 360. Dispenser 102 is caused to operate using such feedback to ensure that a correct dose is provided in dispensed medicine container 365. However, in the illustrated example, medicine, in this example, may be conveyed to and from dispensed medicine container 365 positioned at discharge position 1320 and 380 in both directions, allowing simultaneous or sequential iterations using two containers and two conveying methods in both directions, which may allow convergence to a final dose, and movement of any additional medicine from medicine transfer unit 355 via a second path (i.e., via vacuum head 1315, for containers positioned at position 1320 and 380).

Figure 30:
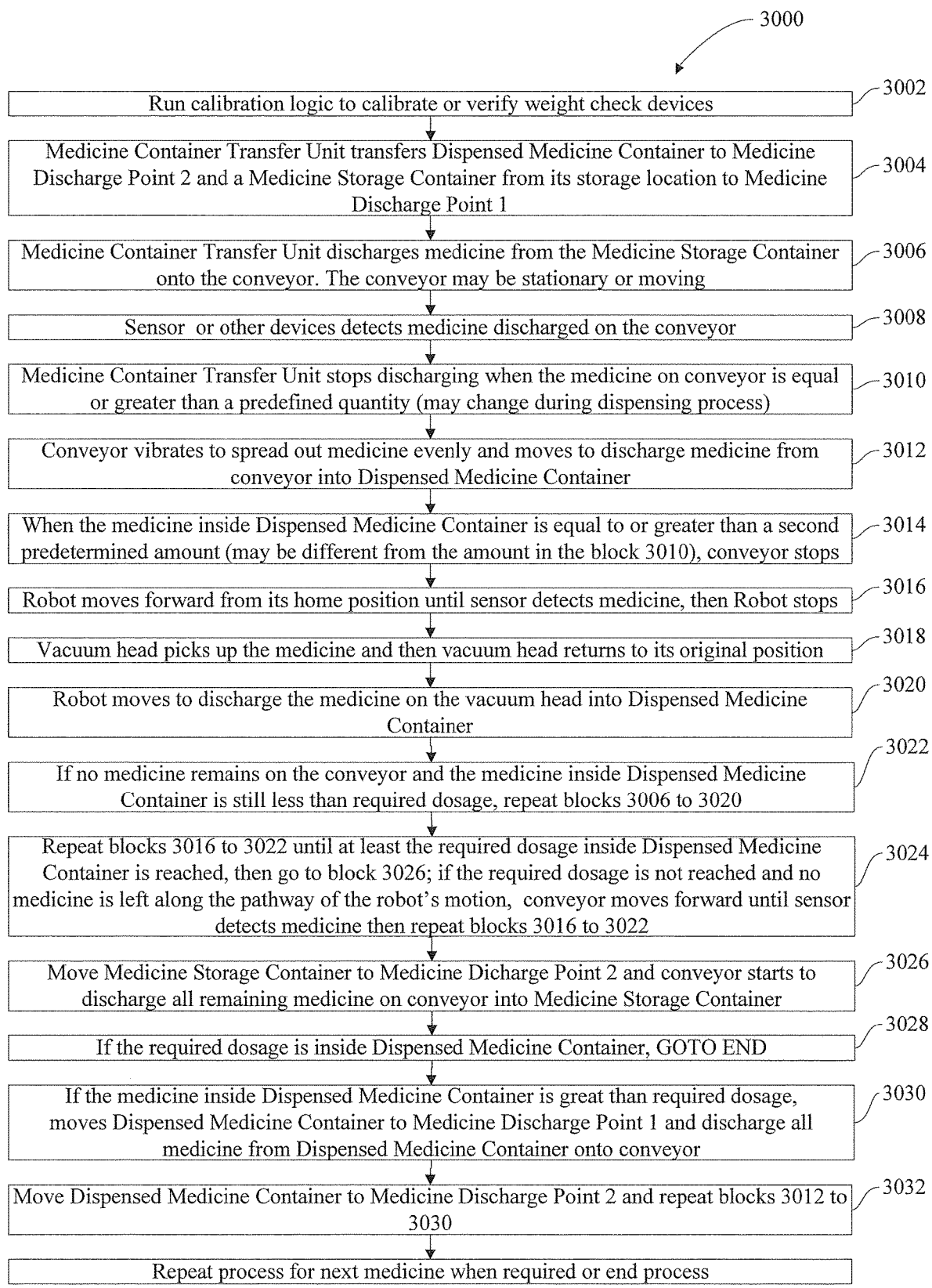
FIG. 30 is a flow diagram illustrating an exemplary process for dispensing a dose of medicine via the exemplary sub-assembly of FIG. 29A-29B.

Referring now to FIG. 30, a flow diagram of another exemplary process 3000 for operating the dispensing unit 102, which may incorporate the sub-assembly 2900, is illustrated. Process 3000 may include operations that may be part of program 110, stored on memory 108, and/or executed by processor 106. Process 3000 may take many different forms and include multiple and/or alternate steps. While an exemplary process is shown, the exemplary steps illustrated are not intended to be limiting. Indeed, additional or alternative steps and/or implementations may be used. In addition, for purposes of process 3000, the medicine container transfer unit 330 is referred to as CNC machine. However, it should be appreciated that any medicine container transfer unit 330 for performing the respective step(s) is contemplated, and that the use of the terms CNC machine and robot are not intended to be limiting.

Process 3000 may begin at block 3002 at which the processor 106 may run calibration and verification logic with calibration and verification device 382 to calibrate or verify weight detecting devices.

At block 3004, the medicine container transfer unit 330 may transfer a dispensed medicine container 365 to the second medicine discharge point 380 and medicine storage container 320 to the first discharge point 350.

At block 3006, medicine container transfer unit 330 may discharge medicine from the medicine storage container 320 onto the conveyor 1105, which may be stationary or moving.

At block 3008, sensor 1110 or other devices may detect medicine discharged on the conveyor 1105.

At block 3010, medicine container transfer unit 330 may stop discharging medicine storage container 320 when medicine on the conveyor 1105 is equal to or greater than a predefined quantity. This may be determined based on feedback from sensor 1110 or other devices.

At block 3012, the conveyor 1105 may vibrates to spread out medicine evenly and may move to discharge medicine from conveyor 1105 into dispensed medicine container 365.

At block 3014, a sensor 1115 and/or scale 395 under the dispensed medicine container 365 and/or weight checking station 360 may detect a quantity of medicine discharged into the dispensed medicine container 365. The conveyor 1105 is stopped based on feedback from the sensor 1115 and/or scale 395 and/or weight checking station 360 that the quantity of medicine inside the dispensed medicine container 365 is equal to or greater than a predetermined amount.

At block 3016, robot 1345 may move from a home position until sensor 1330 detects medicine, after which robot 1345 may stop.

At block 3018, vacuum head 1315 may descend to pick up the medicine and then vacuum head 1315 may return to its original position.

At block 3020, robot 1345 may move to discharge the medicine on the vacuum head 1315 into the dispensed medicine container 365. Robot 1345 may also pick up medicine from dispensed medicine container 365 and discharges onto the medicine transfer unit 355.

At block 3022, processor 106 may determine if any medicine remains on the conveyor 1105. If not, and the medicine inside dispensed medicine container 365 is still less than required dosage, blocks 3006 through 3020 may be repeated.

At block 3024, processor 106 may determine if the medicine in the dispensed medicine container 365 has reached the required dosage. If it has, then process 3000 may proceed to block 3026. If it has not, and there is no medicine left along the pathway of the motion of robot 1345, conveyor 1105 move forward until sensor 1115 detects medicine, then process 3000 may repeat blocks 3016 to 3022 until the required dosage has been reached, after which process 3000 may proceed to block 3026.

At block 3026, medicine container transfer unit 330 may transfer the medicine storage container 320 to the medicine discharge point 380, and discharge all remaining medicine on the conveyor 1105 into the medicine storage container 320.

At block 3028, if the required dosage is inside of the dispensed medicine container 365, process 3000 may then end.

At block 3030, if the medicine inside dispensed medicine container 365 is great than required dosage, move the dispensed medicine container 365 to discharging point 350 and discharge medicine from the dispensed medicine container 365 onto conveyor 1105.

At block 3032, the medicine container transfer unit 330 may transfer a dispensed medicine container 365 to the second medicine discharge point 380 and repeat blocks 3012 to 3030.

Process 3000 may be repeated for the next medicine when required or process 3000 may end.

In embodiments, weight checking station 360 and/or scale(s) 395, for example, in each weighing station or storage nests associated with each container, may check quantity of medicine inside each container involved in process 3000.

In general, process 3000 may be a closed feedback loop process with stable and fast convergent iterations. In addition, the processor 106 may communicate with, i.e., send commands to, receive data from, and the like, to various components of the dispensing unit 102 and/or system 500 to perform process 3000.

Figure 31A:
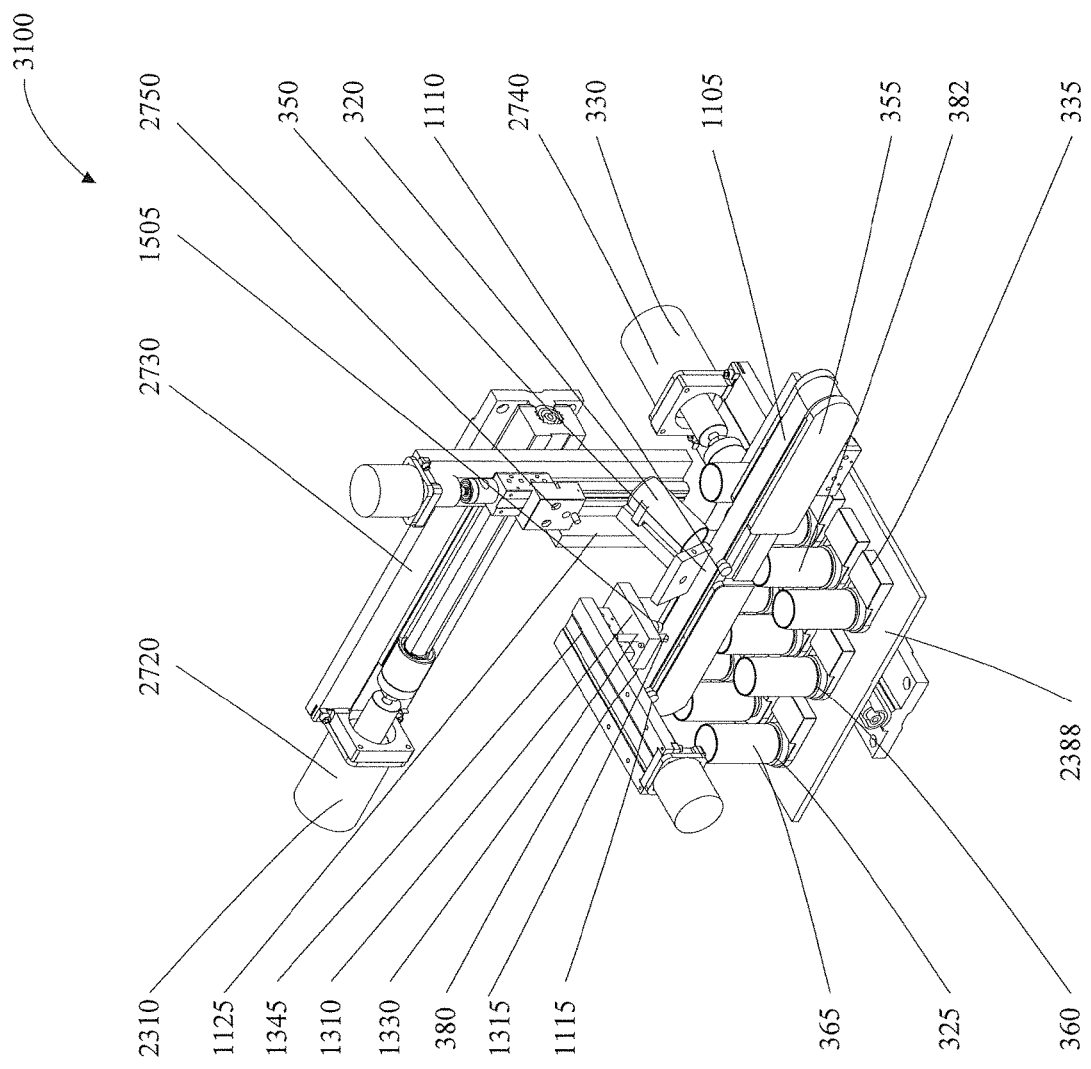
FIG. 31A is a perspective view of a sub-assembly according to another exemplary approach.

FIG. 31A illustrates an exemplary sub-assembly 3100 of dispenser 102 with a conveyor, a robot, a vacuum head (mounted on the same robot or a different robot), a vision system, and CNC machine. In this example medicine container transfer unit 330 includes CNC machine 2720 with end of arm tool 1125, medicine transfer unit 355 includes conveyor 1105, sensors 1110 and 1115, robot 1345 with end of arm tool 1310, sensor 1330, vacuum head 1315, and a machine vision system 1505 coupled to processor 106 and configured to output a visual location and images of items, such pills or capsules, of dispenser 102. CNC machine 2720 and robot 1345 may be two different robots, or two different parts of the same one robot.

Figure 31B:
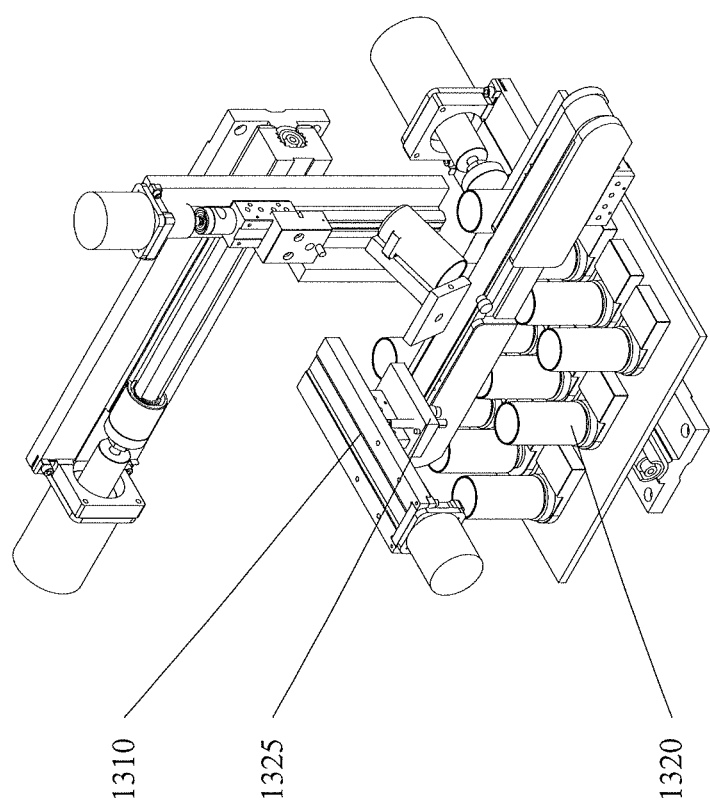
FIG. 31B illustrates the exemplary system of FIG. 31A during operation.

FIG. 31B is a view of the example of FIG. 31A, showing end of arm tool 1310 at medicine discharge position 1325 to discharge medicine into medicine storage container at discharge position 1320. The end of arm tool 1310 may also discharge medicine into medicine storage container at discharge position 380 (not shown). The end of arm tool 1310 may also pick up medicine from medicine containers at discharge position 1320 or 380 and discharge onto medicine transfer unit 355.

Sub-assembly 3100 is a view of inside elements of dispenser 102 and includes a CNC machine. Sub-assembly 3100 includes loading station or medicine container loading station 325, medicine container transfer unit 330, and medicine container storage nest 335. Medicine transfer unit 355, in the illustrated example, may include robot 1345 and conveyor 1105 for transporting or otherwise conveying medicine from first medicine discharge point 350 to second medicine discharge point 380 and third medicine discharge point 1320, and may include sensors 1110 and 1115. Sub-assembly 3100 includes weight checking station 360, a calibration and verification device 382 to automatically calibrate weight detecting devices, and dispensed medicine container 365. Medicine storage container 320 is positioned on container storage device 2388. Weight checking station 360 may have similar design as other medicine container storage nest 335 including a weight checking device 395 and attach to the medicine container storage device 2388. Weight checking station 360 may be a standalone device including a regular pharmacy scale or pharmacy balance.

FIG. 31A is an illustration of medicine storage container 320 as positioned on medicine container storage device 2388, and FIG. 31B of the exemplary system of FIG. 31A shows end of arm tool 1310 at medicine discharge position 1325. Medicine storage container 320 may include original medicine container 390, medicine container identification unit 385, weight detecting device 395, and medicine container storage nest 335. Weight detecting device 395 and medicine container storage nest 335 may be integrated together. Weight detecting device 395 and medicine container storage nest 335 may also be part of medicine container storage device 2388. Weight detecting device 395 may be a scale, a load cell, a balance, or other device for measuring weight, according to the disclosure. Weight detecting device 395 and medicine container storage nest 335 are positioned on medicine container storage device 2388 at each of the illustrated locations. Medicine container identification unit 385 may include identification information particular to a given medicine, and may also identify an amount of medicine that may constitute a single patient dose particular to a given user of dispenser 102.

Referring still to FIG. 31A, medicine storage container 320 may be loaded into dispenser 102 from medicine container loading station 325, and medicine storage container 320 is transferred to its storage position on medicine container storage device 2388 by medicine container transfer unit 330. Medicine storage container 320 may include medicine in the form of a pill or a capsule, as examples, and a dose of medicine for a user may include one or more of the pills or capsules. Medicine container transfer unit 330 is illustrated as having CNC machine 2720 that includes X axis 2730, Y axis 2740, Z axis 2750, and an end of arm tool 1125, but may instead include a conveyor, a robot, or any device that can move medicine storage container 320 from one position to another.

Medicine transfer unit 355 moves medicine from one position to another, accepts medicine from medicine storage container 320, and medicine transfer unit 355 also discharges medicine into medicine storage container 320 or any container when positioned at medicine discharge point 380 and/or 1320.

In operation, as shown in FIGS. 31A and 31B, dispenser 102 moves, via medicine container transfer unit 330, medicine storage container 320 to first medicine discharge point 350. Medicine storage container 320 is, in one example, a medicine storage container which may have an amount of medicine that is in excess of a dose, or an amount of medicine that is desired to be distributed into dispensed medicine container 365. Medicine container transfer unit 330 turns medicine storage container 320 such that a predetermined amount of medicine spills or otherwise pours from medicine storage container 320 onto medicine transfer unit 355, as determined by sensors or medicine detecting device. Medicine container transfer unit 330 moves dispensed medicine container 365 to second medicine discharge point 380. When dispensed medicine container 365 is positioned at medicine discharge point 380, and when medicine has been discharged onto medicine transfer unit 355, medicine transfer unit 355 thereby conveys the discharged medicine from medicine transfer unit 355 into dispensed medicine container 365 until at least a second predetermined amount of medicine is contained in dispensed medicine container 365, as determined by weight checking station 360 and/or weight detecting device 395 and medicine container storage nest 335, which weigh and transmit weight information to for instance a controller of dispenser 102.

Medicine transfer unit 355 includes robot 1345 and conveyor 1105, and sensors 1110 and 1115, which monitor medicine positioned on medicine transfer unit 355 and on conveyor 1105. Sensors 1110, 1115 may be optical sensors that are coupled, electrically or optically as examples, to processor 106. As such, processor 106 monitors an amount of medicine positioned on medicine transfer unit 355 via sensors 1110, 1115. Sensors 1110 and 1115 detect the presence of pills or capsules as they pass thereby via medicine transfer unit 355 to second medicine discharge point 380. In addition, robot 1345 includes end of arm tool 1310 having vacuum head 1315 that may attach via a vacuum, controlled by processor 106, to individual pills or capsules passing along medicine transfer unit 355. Accordingly, in this example, pills or capsules may be not only conveyed by conveyor 1105 to dispensed medicine container 365 when positioned at medicine discharge point 380, but also conveyed by robot 1345 to dispensed medicine container 365 when positioned at medicine discharge point 380. Pills or capsules may also be conveyed by robot 1345 to dispensed medicine container 365 positioned at position 1320. Pills or capsules may also be conveyed by robot 1345 from dispensed medicine container 365 at discharge point 380 or 1320 back to the medicine transfer unit 355. Both methods may be used concurrently or separately. Thus, overall efficiency or movement of pills or capsules may be improved by having an ability to move pills or capsules to two locations simultaneously.

Medicine is transferred from medicine transfer unit 355 into dispensed medicine container 365, and a weight of the medicine is determined via weight detecting device 395 and/or medicine checking station 360. If the measured weight is less than a given or desired dose, and if medicine is still on medicine transfer unit 355 (i.e., has not been fully discharged), then medicine transfer unit 355 further conveys more medicine into dispensed medicine container 365. On the other hand, if no medicine is on medicine transfer unit 355, then additional medicine is discharged to medicine transfer unit 355 from medicine storage container 320. The process of discharging from medicine storage container 320 to medicine transfer unit 355, and from medicine transfer unit 355 to dispensed medicine container 365 continues until at least a dose of medicine is contained in dispensed medicine container 365. That is, dispensed medicine container 365 may include an exact or desired dose, or may include an amount of medicine that is in excess of an exact dose.

If an exact dose is present in dispensed medicine container 365 and medicine is still on the medicine transfer unit 355, then dispenser 102 operates to convey medicine storage container 320 to second discharge point 380 via medicine container transfer unit 330 and discharge any remaining medicine on medicine transfer unit 355 back into medicine storage container 320. The process 3100 may end after this step.

On the other hand, in one example dispensed medicine container 365 may include an amount of medicine that is in excess of an exact dose and medicine is still on the medicine transfer unit 355, then dispenser 102 operates to convey medicine storage container 320 to second discharge point 380 via medicine container transfer unit 330 and discharge any remaining medicine on medicine transfer unit 355 back into medicine storage container 320. In such an example, dispensed medicine container 365 is thereby conveyed to first medicine discharge point 350 and medicine container transfer unit 330 discharges medicine from dispensed medicine container 365 onto medicine transfer unit 355. Then medicine container transfer unit 330 may move medicine container 365 to second discharge point 380 and operations described above are repeated. That is, medicine discharged from dispensed medicine container 365 to medicine transfer unit 355 is thereby conveyed to dispensed medicine container 365 until at least the exact dose is present in dispensed medicine container 365. And, again, if dispensed medicine container 365 includes medicine equal to the dose, then any excess medicine on medicine transfer unit 355 is returned to medicine storage container 320. On the other hand, in one example dispensed medicine container 365 may include an amount of medicine that is in excess of an exact dose. In such an example, operations described above are repeated. That is, medicine container transfer unit 330 discharges medicine from dispensed medicine container 365 onto medicine transfer unit 355 and medicine transfer unit 355 discharges medicine into dispensed medicine container 365.

The aforementioned steps continue until a dose of medicine is contained within dispensed medicine container 365, and any additional medicine is returned to medicine storage container 320. In such fashion, dispenser 102 includes a feedback mechanism, ensuring a proper dose, and only a proper dose, is contained in dispensed medicine container 365. That is, feedback is provided in the form of a weight of pills or capsules, corresponding to a dose, measured via weight detecting device 395 and/or weight checking station 360. Dispenser 102 is caused to operate using such feedback to ensure that a correct dose is provided in dispensed medicine container 365. However, in the illustrated example, medicine, in this example, may be conveyed to and from dispensed medicine container 365 positioned at discharge position 1320 and 380 in both directions, allowing simultaneous or sequential iterations using two containers and two conveying methods in both directions, which may allow convergence to a final dose, and movement of any additional medicine from medicine transfer unit 355 via a second path (i.e., via vacuum head 1315, for containers positioned at position 1320 and 380). Additionally, vision system 1505 provides yet additional functionality, in that vision system 1505 may convey an image of pills or capsules passing along medicine transfer unit 355, providing a visual representation and error checking of the pills or capsules, and an additional method of identifying the movement thereof into dispensed medicine container 365. Processor 106 may compare these images with images stored in database 122 to make sure correct medicine is dispensed.

Figure 32:
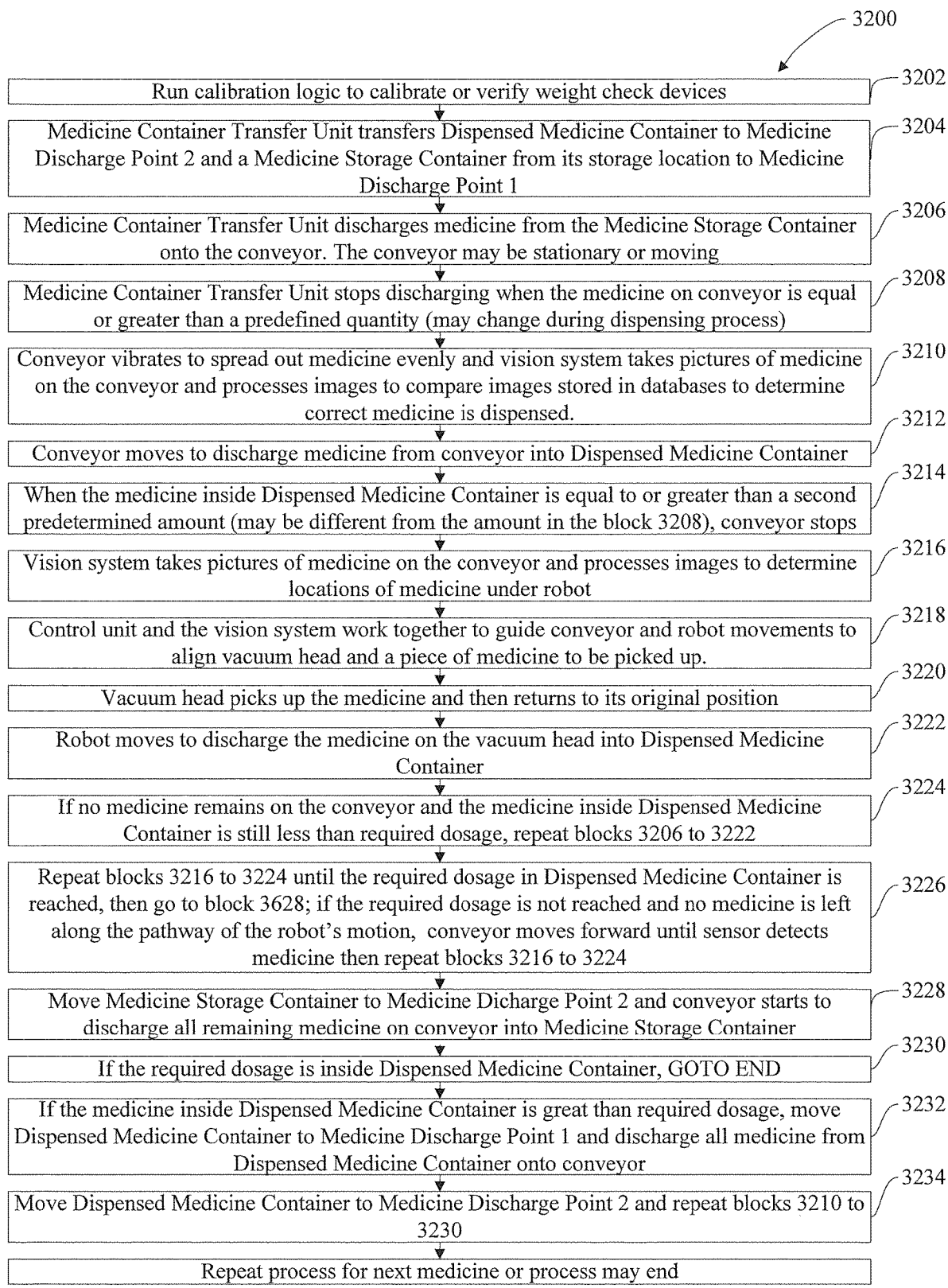
FIG. 32 is a flow diagram illustrating an exemplary process for dispensing a dose of medicine via the exemplary sub-assembly of FIG. 31A-31B.

Referring now to FIG. 32, a flow diagram of another exemplary process 3200 for operating the dispensing unit 102, which may incorporate the sub-assembly 3200, is illustrated. Process 3200 may include operations that may be part of program 110, stored on memory 108, and/or executed by processor 106. Process 3200 may take many different forms and include multiple and/or alternate steps. While an exemplary process is shown, the exemplary steps illustrated are not intended to be limiting. Indeed, additional or alternative steps and/or implementations may be used. In addition, for purposes of process 3200, the medicine container transfer unit 330 is referred to as CNC machine. However, it should be appreciated that any medicine container transfer unit 330 for performing the respective step(s) is contemplated, and that the use of the terms CNC machine and robot are not intended to be limiting.

Process 3200 generally may be the same as or similar to process 3000, but may differ in the incorporation of the vision system 1505.

Process 3200 may begin at block 3202 at which the processor 106 may run calibration and verification logic with calibration and verification device 382 to calibrate or verify weight detecting devices.

At block 3204, the medicine container transfer unit 330 may transfer a dispensed medicine container 365 to the second medicine discharge point 380 and a medicine storage container 320 to a first medicine discharge point 350.

At block 3206, medicine container transfer unit 330 may discharge medicine from the medicine storage container 320 onto the conveyor 1105, which may be stationary or moving.

At block 3208, medicine container transfer unit 330 may stop discharging medicine storage container 320 when medicine on the conveyor 1105 is equal to or greater than a predefined quantity. The predefined quantity may change during the dispensing process. This may be determined based on feedback from sensor 1110, 1115 or other devices.

At block 3210, the conveyor 1105 vibrates to spread out medicine evenly and vision system 1505 may take pictures of medicine on the conveyor 1105 and process images to compare images stored in databases to determine correct medicine is dispensed.

At block 3212, the conveyor 1105 may move to discharge medicine from conveyor 1105 into dispensed medicine container 365.

At block 3214, a sensor 1115 and/or scale 395 under the dispensed medicine container 365 and/or weight checking station 360 may detect a quantity of medicine discharged into the dispensed medicine container 365. The conveyor 1105 is stopped based on feedback from the sensor 1115 and/or scale 395 and/or weight checking station 360 that the quantity of medicine inside the dispensed medicine container 365 is equal to or greater than a predetermined amount. This predetermined amount may be different from the one in block 3208 and may change during the dispensing process. Conveyor 1105 may also stop when the vision system 1505 gives instructions.

At block 3216, the vision system 1505 may take pictures of medicine on the conveyor 1105 and process the images to determine locations of the medicine on the conveyor 1105 under robot 1345.

At block 3218, the processor 106 and the vision system 1505 may work together to guide conveyor 1105 and robot 1345 movements to align vacuum head 1315 and a piece of medicine to be picked up.

The remaining blocks 3220 through 3234 may correspond with blocks 3018 through 3032 of process 3000.

Process 3200 may be repeated for the next medicine when required or the process 3200 may end.

In embodiments, weight checking station 360 and/or scale(s) 395, for example, in each weighing station or storage nests associated with each container, may check quantity of medicine inside each container involved in process 3200.

In general, process 3200 may be a closed feedback loop process with stable and fast convergent iterations. In addition, the processor 106 may communicate with, i.e., send commands to, receive data from, and the like, to various components of the dispensing unit 102 and/or system 500 to perform process 3200.

Figure 33:
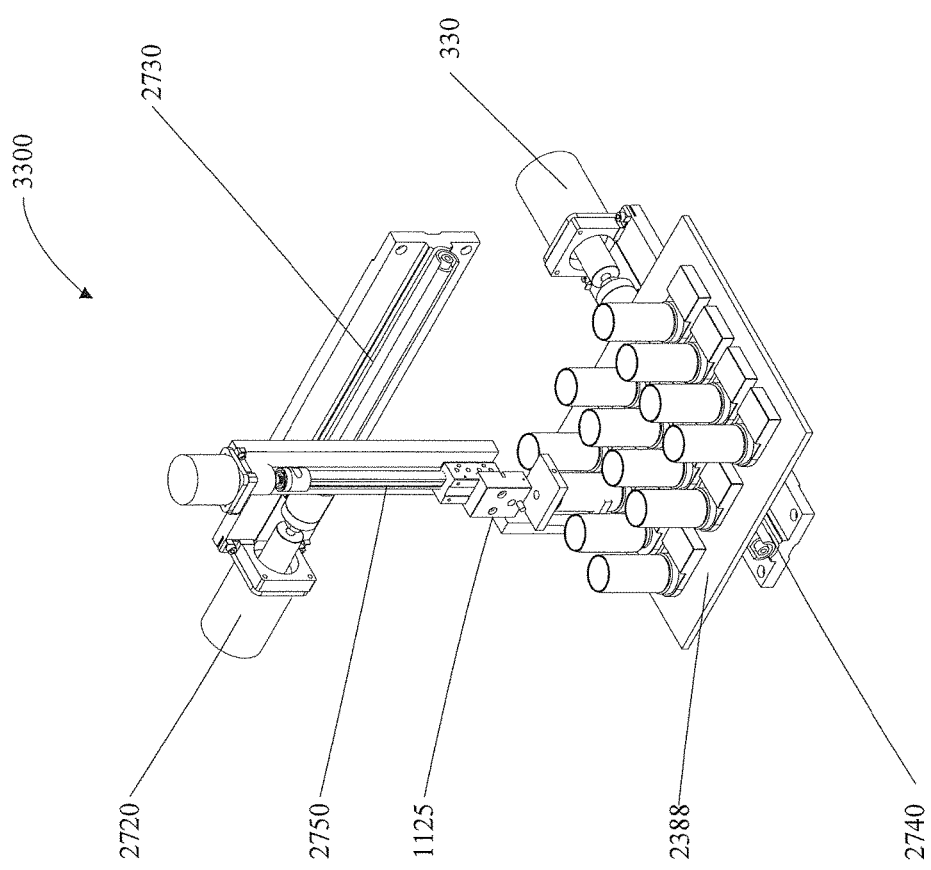
FIG. 33 illustrates a perspective view of an exemplary system including, for example, a container transfer unit 330 and a container storage device 2388.

FIG. 33 illustrates an exemplary sub-assembly 3300 including, e.g. the container transfer unit 330. The container transfer unit 330 may include CNC machine 2720, end of arm tool 1125, and container storage device 2388. In this example CNC machine 2720 may include X axis 2730, Y axis 2740, and Z axis 2750. The container storage device 2388 may be attached to Y axis 2740. Medicine container transfer unit 330 is illustrated as having a CNC machine 2720, but may instead include a conveyor, a robot, or any device that can move medicine storage container 320 from one position to another, and discharge medicine from medicine storage container 320. The Y axis 2740 is illustrated as a sub system of the CNC machine 2720, but may be a different machine working with the CNC machine 2720 and may have many different forms and designs, including a platform, a container of any shape, a shelf, a conveyor, a carousel, a robot, a walking beam, a dial table, a rotary table, a sub assembly, and any device that can move medicine storage container 320.

In operation, X axis 2730 may move the EOAT along the x direction. Y axis 2740 may move container storage device 2388 along y direction to change position of containers in y direction. X axis 2730 and Y axis 2740 may work together to move medicine container and EOAT 1125 to align the container and EOAT 1125. Y axis 2740 may move container storage device 2388 to a required y coordinate for an intended container to align the intended container with the X axis 2730. X axis 2730 may move EOAT 1125 to a required x coordinate to align EOAT 1125 with the intended container. Then Z axis may move to pick up or release or manipulate the intended container.

Figure 34:
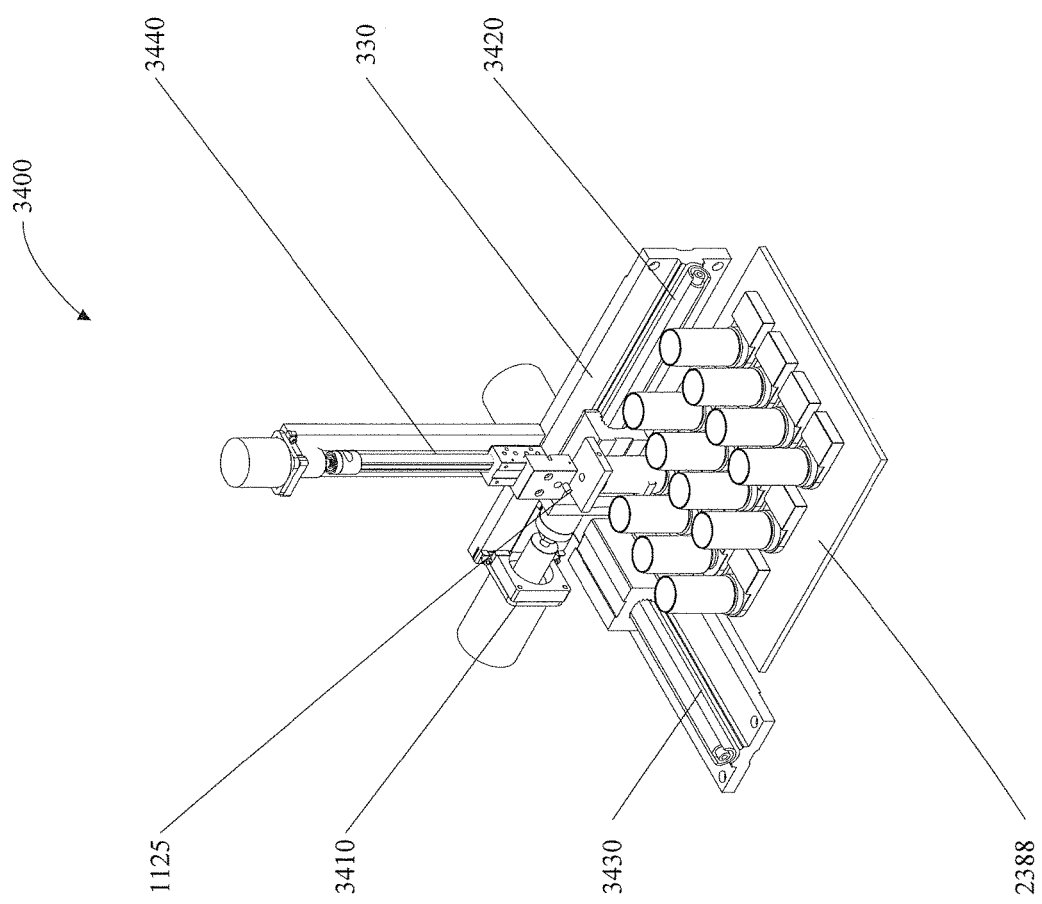
FIG. 34 is a perspective view of a sub-assembly according to another exemplary approach.

FIG. 34 illustrates an exemplary sub-assembly 3400 including, e.g. the container transfer unit 330 and container storage device 2388. The container transfer unit 330 may include CNC machine 3410 and EOAT 1125. In this example CNC machine 3410 may include X axis 3420, Y axis 3430, and Z axis 3440. The container storage device 2388 may be independent from CNC machine movement. The container storage device 2388 may be stationary or movable.

In operation, X axis 3420 and Y axis 3430 may work together to move EOAT 1125 to align EOAT 1125 with an intended container. X axis 3420 may move EOAT 1125 to a required x coordinate and Y axis 3430 may move EOAT 1125 to a required y coordinate to align EOAT 1125 with the intended container. Then Z axis moves to pick up or release or manipulate the intended container.

Figure 35:
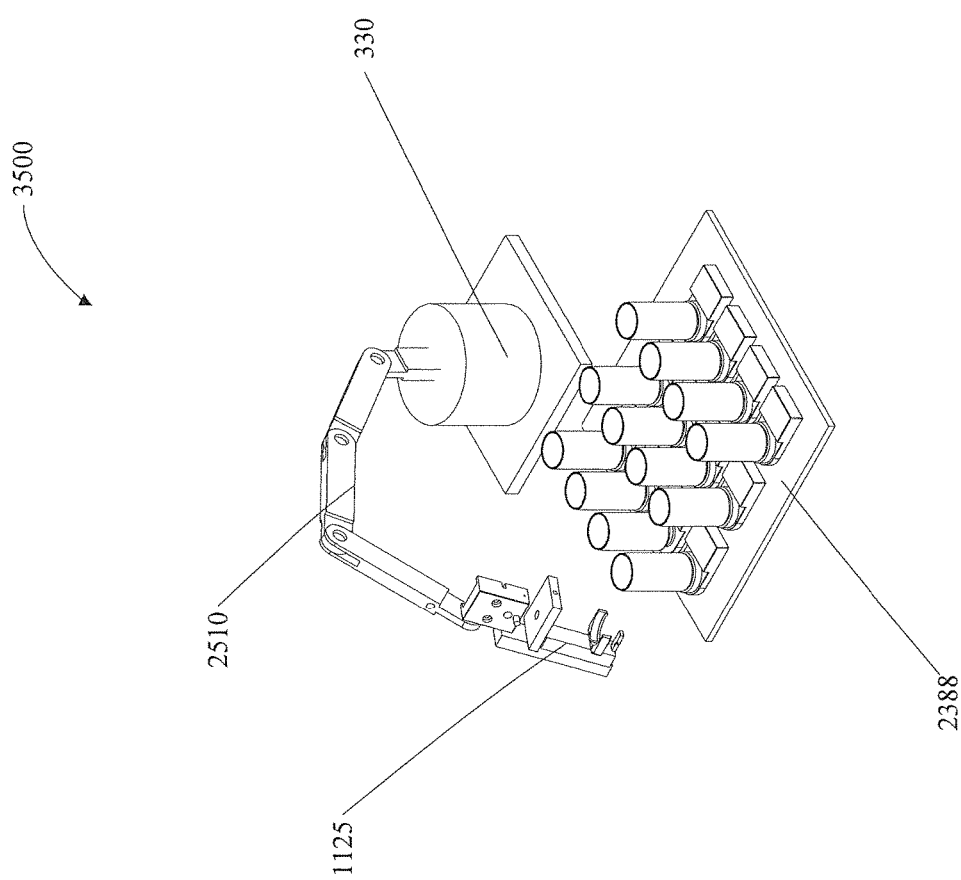
FIG. 35 is a perspective view of a sub-assembly according to another exemplary approach.

FIG. 35 illustrates an exemplary sub-assembly 3500 including, e.g. the container transfer unit 330 and container storage device 2388. The container transfer unit 330 may include multi DOF (degree of freedom) robot 3510 and EOAT 1125. In this example the robot may include a 6 DOF robot. The container storage device 2388 may be independent from robot movement. The container storage device 2388 may be stationary or movable.

In operation, robot 3510 may move EOAT 1125 to required X, Y, Z coordinates to align EOAT 1125 with an intended container and to pick up or release or manipulate the intended container.

Systems and methods are provided for dispensing medication in dosages that comply with a medicine regimen. An exemplary system and method may include operations and/or instructions comprising dispensing medicine from a first medicine container to a transfer device; dispensing medicine from the transfer device to a second medicine container, monitoring a medicine distribution relative to the first medicine container by way of a first sensor, the second medicine container by way of a second sensor, and the transfer device by way of a third sensor; and automatically adjusting the medicine distribution among the first medicine container, the second medicine container, and the transfer device.

A system for dispensing medication includes a medicine container storage device having a plurality of weight check station, a medicine container transfer unit positioned proximate the medicine container storage device, the medicine container transfer unit configured to engage a medicine storage container positioned on one of the weight check stations and move the medical storage container to a first discharge point, and a medicine transfer unit positioned proximate the medicine container transfer unit such that medicine discharged from the medicine storage container at the first discharge point is discharged onto the medicine transfer unit, and medicine on the medicine transfer unit is discharged from the medicine transfer unit at a second discharge point, the medicine transfer unit having a sensor to estimate how much medicine is on the medicine transfer unit. The system also includes a dispensed medicine container positioned on one of the weight check stations at the second discharge point to receive the medicine discharged from the medicine transfer unit and a controller. The controller is configured to cause the medicine storage container to discharge at least a first predetermined amount of medicine from the medicine storage container onto the medicine transfer unit, cause the medicine transfer unit to discharge at least a second predetermined amount of medicine to dispensed medicine container, determine whether the dispensed medicine container has an amount of medicine greater than a desired single dose, and if the amount of medicine in dispensed medicine container is greater than the desired single dose, then move the dispensed medicine container to the first discharge point via the medicine container transfer unit, and discharge medicine from dispensed medicine container, onto the medicine transfer unit, then move the dispensed medicine container to the second discharge point and discharge medicine from the medicine transfer unit into the dispensed medicine container.

The controller is further configured to move the dispensed medicine container to the first discharge position, and discharge medicine from the dispensed medicine container onto the medicine transfer unit and move the dispensed medicine container to the second discharge point and discharge from the medicine transfer unit into the dispensed medicine container until at least the desired single dose of medicine is present in the dispensed medicine container.

It will be appreciated by those skilled in the art that the present invention may be embodied in other specific forms without departing from the spirit or essential character thereof. The described embodiments are therefore considered in all respects to be illustrative not restrictive. The scope of the invention is indicated by the appended clauses, not the foregoing description, and all changes that come within the meaning and range of equivalents thereof are intended to be embraced therein.

What is claimed is:

1. A medication dispensing system comprising:
a medicine transfer device configured to transfer medicine between a first container and a second container, wherein the first container is configured to initially store medicine; and
a controller configured to
determine a first predetermined amount of medicine to be dispensed from the medicine dispensing system,
cause the medicine transfer device to (i) discharge at least a second predetermined amount of the medicine from the first container onto the medicine transfer device, and (ii) transfer at least a third predetermined amount of the medicine from the medicine transfer device to the second container,
subsequent to the transfer of the third predetermined amount of the medicine, determine whether the second container has greater than or equal to the first predetermined amount of the medicine,
if the second container has less than the first predetermined amount of the medicine, cause the medicine transfer device to at least one of (i) transfer at least a portion of the medicine on the medicine transfer device into the second container, or (ii) discharge at least a portion of the medicine in the first container onto the medicine transfer device, and
until the second container has the first predetermined amount of the medicine, iteratively perform a plurality of operations including at least one of
discharging medicine remaining on the medicine transfer device into the first container,
discharging at least a portion of the medicine in the second container onto the medicine transfer device, and
transferring at least a portion of the medicine on the medicine transfer device into the second container,
wherein each iteration of the plurality of operations includes discharging less medicine from the medicine transfer device into the second container than during the previous iteration.

2. The medication dispensing system of claim 1, wherein the controller is configured to, if the second container does not have the first predetermined amount of the medicine, discharge medicine remaining on the medicine transfer device into the first container prior to discharging the at least a portion of the medicine in the second container onto the medicine transfer device.

3. The medication dispensing system of claim 1, wherein:
the second predetermined amount of the medicine is greater than or equal to the first predetermined amount of the medicine; and
the third predetermined amount of the medicine is greater than or equal to the first predetermined amount of the medicine and less than or equal to the second predetermined amount of the medicine.

4. The medication dispensing system of claim 1, wherein the medicine transfer device comprises at least one of a conveyor or a rotating table.

5. The medication dispensing system of claim 1, further comprising a device configured to generate a signal, wherein:

the signal is indicative of an amount of medicine in at least one of the first container or the second container; and
the controller is configured to, based on the signal, at least one of (i) discharge the at least a portion of the medicine in the first container onto the medicine transfer device, (ii) transfer the at least a portion of the medicine on the medicine transfer device into the second container, (iii) transfer the medicine remaining on the medicine transfer device to the first container, or (iv) discharge the at least a portion of the medicine in the second container onto the medicine transfer device.

6. The medication dispensing system of claim 1 further comprising a plurality of devices configured to generate a plurality of signals, wherein:
the plurality of signals are indicative of amounts of medicine at least one of in the first container, in the second container, or on the medicine transfer device; and
the controller is configured to, based on the signals, at least one of (i) discharge the at least a portion of the medicine in the first container onto the medicine transfer device, (ii) transfer the at least a portion of the medicine on the medicine transfer device into the second container, (iii) transfer the medicine remaining on the medicine transfer device to the first container, or (iv) discharge the at least a portion of the medicine in the second container onto the medicine transfer device.

7. A medication dispensing system comprising:
a medicine transfer device configured to transfer medicine between a first container and a second container, wherein the first container is configured to initially store medicine;
a controller configured to
determine a first predetermined amount of medicine to be dispensed from the medicine dispensing system,
cause the medicine transfer device to (i) discharge at least a second predetermined amount of the medicine from the first container onto the medicine transfer device, and (ii) transfer at least a third predetermined amount of the medicine from the medicine transfer device to the second container,
subsequent to the transfer of the third predetermined amount of the medicine, determine whether the second container has greater than or equal to the first predetermined amount of the medicine, and
if the second container has less than the first predetermined amount of the medicine, cause the medicine transfer device to at least one of (i) transfer at least a portion of the medicine on the medicine transfer device into the second container, or (ii) discharge at least a portion of the medicine in the first container onto the medicine transfer device; and
a container transfer device configured to move the first container and the second container between a first station and a second station,
wherein
the first container is (i) at the first station while discharging medicine onto the medicine transfer device, and (ii) at the second station while the medicine transfer device is transferring medicine into the first container, and
the second container is (i) at the first station while discharging medicine onto the medicine transfer device, and (ii) at the second station while the medicine transfer device is transferring medicine into the second container.

8. The medication dispensing system of claim 7, wherein the container transfer device comprises at least one of a computer numerical control machine, a carousel or a robot.

9. A medication dispensing system comprising:
- a medicine transfer device configured to transfer medicine between a first container and a second container, wherein the first container is configured to initially store medicine; and
- a controller configured to
  - determine a first predetermined amount of medicine to be dispensed from the medication dispensing system,
  - cause the medicine transfer device to (i) discharge at least a second predetermined amount of the medicine from the first container onto the medicine transfer device, and (ii) transfer at least a third predetermined amount of the medicine from the medicine transfer device to the second container,
  - subsequent to the transfer of the third predetermined amount of the medicine, determine whether the second container has greater than or equal to the first predetermined amount of the medicine, and
  - if the second container has less than the first predetermined amount of the medicine, cause the medicine transfer device to at least one of (i) transfer at least a portion of the medicine on the medicine transfer device into the second container, or (ii), discharge at least a portion of the medicine in the first container onto the medicine transfer device;
- a container transfer device configured to move the first container and the second container between a first station and a second station; and
- a device configured to generate a signal, wherein
- the signal is indicative of at least one of (i) an amount of medicine on the medicine transfer device, or (ii) whether medicine remains on the medicine transfer device, and
- the controller is configured to, based on the signal, at least one of (i) discharge the at least a portion of the medicine in the first container onto the medicine transfer device, (ii) transfer the at least a portion of the medicine on the medicine transfer device into the second container, (iii) transfer the medicine remaining on the medicine transfer device to the first container, or (iv) discharge the at least a portion of the medicine in the second container onto the medicine transfer device.

* * * * *